United States Patent
Wong et al.

(10) Patent No.: US 9,034,402 B2
(45) Date of Patent: May 19, 2015

(54) PROTEIN HYDROLYSATE COMPOSITIONS HAVING IMPROVED SENSORY CHARACTERISTICS AND PHYSICAL PROPERTIES

(75) Inventors: Theodore M. Wong, Ballwin, MO (US); Phillip S. Kerr, Wildwood, MO (US); Parthasarathi Ghosh, Chesterfield, MO (US); Jason F. Lombardi, Edwardsville, IL (US); Yadilka Maldonado, Dardenne Prairie, MO (US); Gitte B. Lynglev, Frederiksberg (DK); Tine Hoff, Holte (DK); Lars L H Christensen, Alleroed (DK); Peter R. Oestergaard, Virum (DK)

(73) Assignee: Solae, LLC, St. Louis, MO (US)

( * ) Notice: Subject to any disclaimer, the term of this patent is extended or adjusted under 35 U.S.C. 154(b) by 739 days.

(21) Appl. No.: 12/103,514

(22) Filed: Apr. 15, 2008

(65) Prior Publication Data
US 2008/0305212 A1     Dec. 11, 2008

Related U.S. Application Data

(60) Provisional application No. 60/911,935, filed on Apr. 16, 2007.

(51) Int. Cl.
| | |
|---|---|
| A23C 17/00 | (2006.01) |
| A23J 1/00 | (2006.01) |
| A23J 3/34 | (2006.01) |
| A23C 9/152 | (2006.01) |
| A23C 11/10 | (2006.01) |
| A23L 1/305 | (2006.01) |
| A23L 2/66 | (2006.01) |
| C12P 21/06 | (2006.01) |

(52) U.S. Cl.
CPC ............ *A23J 3/34* (2013.01); *A23C 9/1526* (2013.01); *A23C 11/103* (2013.01); *A23J 3/343* (2013.01); *A23J 3/346* (2013.01); *A23L 1/3053* (2013.01); *A23L 1/3055* (2013.01); *A23L 1/3056* (2013.01); *A23L 2/66* (2013.01); *C12P 21/06* (2013.01); *C12Y 304/21004* (2013.01)

(58) Field of Classification Search
CPC ....... A23C 11/103; A23C 9/1526; A23J 3/34; A23J 3/343; A23L 1/3053; A23L 1/3055; A23L 1/3056; A23L 2/66; C12P 21/06; C12Y 304/21004
See application file for complete search history.

(56) References Cited

U.S. PATENT DOCUMENTS

| | | | | |
|---|---|---|---|---|
| 4,167,587 | A | * | 9/1979 | Danforth .................. 426/250 |
| 4,632,903 | A | * | 12/1986 | Boyce et al. .............. 435/68.1 |
| 5,024,849 | A | * | 6/1991 | Rasilewicz ................ 426/656 |
| 5,288,627 | A | * | 2/1994 | Nielsen et al. ............. 435/223 |
| 5,691,165 | A | * | 11/1997 | Nielsen et al. ............ 435/68.1 |
| 5,693,520 | A | * | 12/1997 | Branner et al. ............ 435/213 |
| 5,866,357 | A | * | 2/1999 | Dambmann et al. ....... 435/68.1 |
| 6,036,983 | A | | 3/2000 | Nielsen |
| 6,221,423 | B1 | | 4/2001 | Cho et al. |
| 7,332,192 | B2 | * | 2/2008 | Cho et al. ................. 426/656 |
| 2004/0034888 | A1 | * | 2/2004 | Liu et al. .................. 800/289 |

FOREIGN PATENT DOCUMENTS

| | | | | |
|---|---|---|---|---|
| WO | WO 89/06270 | * | 7/1989 | ........... C11D 3/386 |

OTHER PUBLICATIONS

Trypsin Cleaves Exclusively C-terminal to Arginine and Lysine Residues. Molecular and Cellular Proteomics. 2004. vol. 3, pp. 608-614.*
L'Hocine et al., J. Agric. Food Chem. 2007, vol. 55, No. 14: pp. 5819-5826.
Mooney, B.P., et al., "High-Throughput Peptide Mass Fingerprinting of Soybeanseed Proteins: Automated Workflow and Utility of UniGene Expressed Sequence Tag Databases for Protein Identification", Phytochemistry 65 (2004) pp. 1733-1744.
Agrawal, G. K., et al., In-Depth Investigation of the Soybean Seed-Filling Proteome and Comparison with a Parallel Study of Rapeseed1 [W] [OA], Plant Physiol vol. 148, 2008.
Krishnan, H. B., et al., "All Three Subunits of Soybean-Conglycinin Are Potential Food Allergens", J. Agric. Food Chem., vol. 57, No. 3, 2009.
Olsen, J. V., et al., "Trypsin Cleaves Exclusively C-Terminal to Arginine and Lysine Residues" Molecular & Cellular Proteomics, vol. 3, 2004, pp. 608-614, XP002499112: URL: http://www.mcponline.org/cgi/reprint/T400003-MCP200v1.

* cited by examiner

*Primary Examiner* — Marcela M Cordero Garcia

(57) ABSTRACT

The present invention provides protein hydrolysate compositions, processes for making protein hydrolysate compositions, and food products comprising protein hydrolysate compositions. The protein hydrolysate compositions generally comprise polypeptide fragments having primarily either an arginine residue or a lysine residue at each carboxyl terminus.

48 Claims, 24 Drawing Sheets

SEQUENCE LISTING

<160> NUMBER OF SEQ ID NOS: 274

<210> SEQ ID NO 1
<211> LENGTH: 248
<212> TYPE: PRT
<213> ORGANISM: Fusarium oxysporum

<400> SEQUENCE: 1

```
Met Val Lys Phe Ala Ser Val Val Ala Leu Val Ala Pro Leu Ala Ala
 1               5                  10                  15

Ala Ala Pro Gln Glu Ile Pro Asn Ile Val Gly Gly Thr Ser Ala Ser
            20                  25                  30

Ala Gly Asp Phe Pro Phe Ile Val Ser Ile Ser Arg Asn Gly Gly Pro
        35                  40                  45

Trp Cys Gly Gly Ser Leu Leu Asn Ala Asn Thr Val Leu Thr Ala Ala
    50                  55                  60

His Cys Val Ser Gly Tyr Ala Gln Ser Gly Phe Gln Ile Arg Ala Gly
65                  70                  75                  80

Ser Leu Ser Arg Thr Ser Gly Gly Ile Thr Ser Ser Leu Ser Ser Val
                85                  90                  95

Arg Val His Pro Ser Tyr Ser Gly Asn Asn Asn Asp Leu Ala Ile Leu
            100                 105                 110

Lys Leu Ser Thr Ser Ile Pro Ser Gly Gly Asn Ile Gly Tyr Ala Arg
        115                 120                 125

Leu Ala Ala Ser Gly Ser Asp Pro Val Ala Gly Ser Ser Ala Thr Val
    130                 135                 140

Ala Gly Trp Gly Ala Thr Ser Glu Gly Gly Ser Ser Thr Pro Val Asn
145                 150                 155                 160

Leu Leu Lys Val Thr Val Pro Ile Val Ser Arg Ala Thr Cys Arg Ala
                165                 170                 175
```

```
Gln Tyr Gly Thr Ser Ala Ile Thr Asn Gln Met Phe Cys Ala Gly Val
            180                 185                 190

Ser Ser Gly Gly Lys Asp Ser Cys Gln Gly Asp Ser Gly Gly Pro Ile
            195                 200                 205

Val Asp Ser Ser Asn Thr Leu Ile Gly Ala Val Ser Trp Gly Asn Gly
210                 215                 220

Cys Ala Arg Pro Asn Tyr Ser Gly Val Tyr Ala Ser Val Gly Ala Leu
225                 230                 235                 240

Arg Ser Phe Ile Asp Thr Tyr Ala
            245

<210> SEQ ID NO 2
<211> LENGTH: 251
<212> TYPE: PRT
<213> ORGANISM: Fusariun solani

<400> SEQUENCE: 2

Met Val Lys Phe Ala Ala Ile Leu Ala Leu Val Ala Pro Leu Val Ala
1               5                   10                  15

Ala Arg Pro Gln Asp Ser Ser Pro Met Ile Val Gly Gly Thr Ala Ala
            20                  25                  30

Ser Ala Gly Asp Phe Pro Phe Ile Val Ser Ile Ala Tyr Asn Gly Gly
            35                  40                  45

Pro Trp Cys Gly Gly Thr Leu Leu Asn Ala Asn Thr Val Met Thr Ala
        50                  55                  60

Ala His Cys Thr Gln Gly Arg Ser Ala Ser Ala Phe Gln Val Arg Ala
65                  70                  75                  80

Gly Ser Leu Asn Arg Asn Ser Gly Gly Val Thr Ser Ser Val Ser Ser
                85                  90                  95

Ile Arg Ile His Pro Ser Phe Ser Ser Thr Leu Asn Asn Asp Val
            100                 105                 110

Ser Ile Leu Lys Leu Ser Thr Pro Ile Ser Thr Ser Thr Ile Ser
            115                 120                 125

Tyr Gly Arg Leu Ala Ala Ser Gly Ser Asp Pro Val Ala Gly Ser Asp
130                 135                 140

Ala Thr Val Ala Gly Trp Gly Val Thr Ser Gln Gly Ser Ser Ser Ser
145                 150                 155                 160

Pro Val Ala Leu Arg Lys Val Thr Ile Pro Ile Val Ser Arg Thr Thr
                165                 170                 175

Cys Arg Ser Gln Tyr Gly Thr Ser Ala Ile Thr Thr Asn Met Phe Cys
            180                 185                 190

Ala Gly Leu Ala Glu Gly Gly Lys Asp Ser Cys Gln Gly Asp Ser Gly
            195                 200                 205

Gly Pro Ile Val Asp Thr Ser Asn Thr Val Ile Gly Ile Val Ser Trp
        210                 215                 220

Gly Glu Gly Cys Ala Gln Pro Asn Leu Ser Gly Val Tyr Ala Arg Val
225                 230                 235                 240

Gly Ser Leu Arg Thr Tyr Ile Asp Gly Gln Leu
                245                 250

<210> SEQ ID NO 3
<211> LENGTH: 250
<212> TYPE: PRT
<213> ORGANISM: Fusariun cf. solani

<400> SEQUENCE: 3
```

```
Met Val Lys Phe Ala Ala Ile Leu Ala Leu Val Ala Pro Leu Val Ala
1               5                   10                  15

Ala Arg Pro Gln Asp Arg Pro Met Ile Val Gly Gly Thr Ala Ala Ser
            20                  25                  30

Ala Gly Asp Phe Pro Phe Ile Val Ser Ile Ala Tyr Asn Gly Gly Pro
        35                  40                  45

Trp Cys Gly Gly Thr Leu Leu Asn Ala Ser Thr Val Leu Thr Ala Ala
    50                  55                  60

His Cys Thr Gln Gly Arg Ser Ala Ser Ala Phe Gln Val Arg Ala Gly
65                  70                  75                  80

Ser Leu Asn Arg Asn Ser Gly Gly Val Thr Ser Ala Val Ser Ser Ile
                85                  90                  95

Arg Ile His Pro Ser Phe Ser Gly Ser Thr Leu Asn Asn Asp Val Ser
            100                 105                 110

Ile Leu Lys Leu Ser Thr Pro Ile Ser Thr Ser Thr Ile Ser Tyr
        115                 120                 125

Gly Arg Leu Ala Ala Ser Gly Ser Asp Pro Ala Ala Gly Ser Asp Ala
    130                 135                 140

Thr Val Ala Gly Trp Gly Val Thr Ser Gln Gly Ser Ser Ser Ser Pro
145                 150                 155                 160

Val Ala Leu Arg Lys Val Thr Ile Pro Ile Val Ser Arg Thr Thr Cys
                165                 170                 175

Arg Ser Gln Tyr Gly Thr Ser Ala Ile Thr Thr Asn Met Phe Cys Ala
            180                 185                 190

Gly Leu Ala Glu Gly Gly Lys Asp Ser Cys Gln Gly Asp Ser Gly Gly
        195                 200                 205

Pro Ile Val Asp Thr Ser Asn Thr Val Ile Gly Ile Val Ser Trp Gly
    210                 215                 220

Glu Gly Cys Ala Gln Pro Asn Phe Ser Gly Val Tyr Ala Arg Val Gly
225                 230                 235                 240

Ser Leu Arg Ser Tyr Ile Asp Gly Gln Leu
                245                 250

<210> SEQ ID NO 4
<211> LENGTH: 653
<212> TYPE: PRT
<213> ORGANISM: Achromobacter lyticus

<400> SEQUENCE: 4

Met Lys Arg Ile Cys Gly Ser Leu Leu Leu Gly Leu Ser Ile Ser
1               5                   10                  15

Ala Ala Leu Ala Ala Pro Ala Ser Arg Pro Ala Ala Phe Asp Tyr Ala
            20                  25                  30

Asn Leu Ser Ser Val Asp Lys Val Ala Leu Arg Thr Met Pro Ala Val
        35                  40                  45

Asp Val Ala Lys Ala Lys Ala Glu Asp Leu Gln Arg Asp Lys Arg Gly
    50                  55                  60

Asp Ile Pro Arg Phe Ala Leu Ala Ile Asp Val Asp Met Thr Pro Gln
65                  70                  75                  80

Asn Ser Gly Ala Trp Glu Tyr Thr Ala Asp Gly Gln Phe Ala Val Trp
                85                  90                  95

Arg Gln Arg Val Arg Ser Glu Lys Ala Leu Ser Leu Asn Phe Gly Phe
            100                 105                 110

Thr Asp Tyr Tyr Met Pro Ala Gly Gly Arg Leu Leu Val Tyr Pro Ala
```

```
              115                 120                 125
Thr Gln Ala Pro Ala Gly Asp Arg Gly Leu Ile Ser Gln Tyr Asp Ala
        130                 135                 140

Ser Asn Asn Asn Ser Ala Arg Gln Leu Trp Thr Ala Val Val Pro Gly
145                 150                 155                 160

Ala Glu Ala Val Ile Glu Ala Val Ile Pro Arg Asp Lys Val Gly Glu
                165                 170                 175

Phe Lys Leu Arg Leu Thr Lys Val Asn His Asp Tyr Val Gly Phe Gly
                180                 185                 190

Pro Leu Ala Arg Arg Leu Ala Ala Ala Ser Gly Glu Lys Gly Val Ser
                195                 200                 205

Gly Ser Cys Asn Ile Asp Val Val Cys Pro Glu Gly Asp Gly Arg Arg
        210                 215                 220

Asp Ile Ile Arg Ala Val Gly Ala Tyr Ser Lys Ser Gly Thr Leu Ala
225                 230                 235                 240

Cys Thr Gly Ser Leu Val Asn Asn Thr Ala Asn Asp Arg Lys Met Tyr
                245                 250                 255

Phe Leu Thr Ala His His Cys Gly Met Gly Thr Ala Ser Thr Ala Ala
                260                 265                 270

Ser Ile Val Val Tyr Trp Asn Tyr Gln Asn Ser Thr Cys Arg Ala Pro
                275                 280                 285

Asn Thr Pro Ala Ser Gly Ala Asn Gly Asp Gly Ser Met Ser Gln Thr
        290                 295                 300

Gln Ser Gly Ser Thr Val Lys Ala Thr Tyr Ala Thr Ser Asp Phe Thr
305                 310                 315                 320

Leu Leu Glu Leu Asn Asn Ala Ala Asn Pro Ala Phe Asn Leu Phe Trp
                325                 330                 335

Ala Gly Trp Asp Arg Arg Asp Gln Asn Tyr Pro Gly Ala Ile Ala Ile
                340                 345                 350

His His Pro Asn Val Ala Glu Lys Arg Ile Ser Asn Ser Thr Ser Pro
                355                 360                 365

Thr Ser Phe Val Ala Trp Gly Gly Gly Ala Gly Thr Thr His Leu Asn
        370                 375                 380

Val Gln Trp Gln Pro Ser Gly Gly Val Thr Glu Pro Gly Ser Ser Gly
385                 390                 395                 400

Ser Pro Ile Tyr Ser Pro Glu Lys Arg Val Leu Gly Gln Leu His Gly
                405                 410                 415

Gly Pro Ser Ser Cys Ser Ala Thr Gly Thr Asn Arg Ser Asp Gln Tyr
                420                 425                 430

Gly Arg Val Phe Thr Ser Trp Thr Gly Gly Ala Ala Ala Ser Arg
                435                 440                 445

Leu Ser Asp Trp Leu Asp Pro Ala Ser Thr Gly Ala Gln Phe Ile Asp
        450                 455                 460

Gly Leu Asp Ser Gly Gly Gly Thr Pro Asn Thr Pro Val Ala Asn
465                 470                 475                 480

Phe Thr Ser Thr Thr Ser Gly Leu Thr Ala Thr Phe Thr Asp Ser Ser
                485                 490                 495

Thr Asp Ser Asp Gly Ser Ile Ala Ser Arg Ser Trp Asn Phe Gly Asp
                500                 505                 510

Gly Ser Thr Ser Thr Ala Thr Asn Pro Ser Lys Thr Tyr Ala Ala Ala
                515                 520                 525

Gly Thr Tyr Thr Val Thr Leu Thr Val Thr Asp Asn Gly Gly Ala Thr
        530                 535                 540
```

-continued

```
Asn Thr Lys Thr Gly Ser Val Thr Val Ser Gly Pro Gly Ala Gln
545                 550                 555                 560

Thr Tyr Thr Asn Asp Thr Val Ala Ile Pro Asp Asn Ala Thr Val
                565                 570                 575

Glu Ser Pro Ile Thr Val Ser Gly Arg Thr Gly Asn Gly Ser Ala Thr
            580                 585                 590

Thr Pro Ile Gln Val Thr Ile Tyr His Thr Tyr Lys Ser Asp Leu Lys
        595                 600                 605

Val Asp Leu Val Ala Pro Asp Gly Thr Val Tyr Asn Leu His Asn Arg
610                 615                 620

Thr Gly Gly Ser Ala His Asn Ile Ile Gln Thr Phe Thr Lys Asp Leu
625                 630                 635                 640

Ser Ser Glu Ala Ala Gln Arg Ala Pro Gly Ser Cys Gly
                645                 650
```

```
<210> SEQ ID NO 5
<211> LENGTH: 7
<212> TYPE: PRT
<213> ORGANISM: Glycine max

<400> SEQUENCE: 5

Tyr Ser Asn Lys Leu Gly Lys
1               5

<210> SEQ ID NO 6
<211> LENGTH: 7
<212> TYPE: PRT
<213> ORGANISM: Glycine max

<400> SEQUENCE: 6

Arg Phe Glu Thr Leu Phe Lys
1               5

<210> SEQ ID NO 7
<211> LENGTH: 8
<212> TYPE: PRT
<213> ORGANISM: Glycine max

<400> SEQUENCE: 7

Ser Pro Gln Leu Gln Leu Asn Arg
1               5

<210> SEQ ID NO 8
<211> LENGTH: 9
<212> TYPE: PRT
<213> ORGANISM: Glycine max

<400> SEQUENCE: 8

Ser Arg Asp Pro Ile Ser Tyr Asn Lys
1               5

<210> SEQ ID NO 9
<211> LENGTH: 10
<212> TYPE: PRT
<213> ORGANISM: Glycine max

<400> SEQUENCE: 9

Ser Ser Glu Asp Lys Pro Phe Asn Leu Arg
1               5                   10

<210> SEQ ID NO 10
```

```
<211> LENGTH: 10
<212> TYPE: PRT
<213> ORGANISM: Glycine max

<400> SEQUENCE: 10

Ser Ser Glu Asp Glu Pro Phe Asn Leu Arg
1               5                   10

<210> SEQ ID NO 11
<211> LENGTH: 12
<212> TYPE: PRT
<213> ORGANISM: Glycine max

<400> SEQUENCE: 11

Asn Phe Leu Ala Gly Glu Lys Asp Asn Val Val Arg
1               5                   10

<210> SEQ ID NO 12
<211> LENGTH: 6
<212> TYPE: PRT
<213> ORGANISM: Glycine max

<400> SEQUENCE: 12

Asn Asn Asn Pro Phe Lys
1               5

<210> SEQ ID NO 13
<211> LENGTH: 10
<212> TYPE: PRT
<213> ORGANISM: Glycine max

<400> SEQUENCE: 13

Leu Ser Ala Ala Glu Phe Gly Ser Leu Arg
1               5                   10

<210> SEQ ID NO 14
<211> LENGTH: 12
<212> TYPE: PRT
<213> ORGANISM: Glycine max

<400> SEQUENCE: 14

Ser Gln Ser Asp Asn Phe Glu Tyr Val Ser Phe Lys
1               5                   10

<210> SEQ ID NO 15
<211> LENGTH: 12
<212> TYPE: PRT
<213> ORGANISM: Glycine max

<400> SEQUENCE: 15

Pro Glu Glu Val Ile Gln His Thr Phe Asn Leu Lys
1               5                   10

<210> SEQ ID NO 16
<211> LENGTH: 13
<212> TYPE: PRT
<213> ORGANISM: Glycine max

<400> SEQUENCE: 16

Phe Tyr Leu Ala Gly Asn Gln Glu Gln Glu Phe Leu Lys
1               5                   10

<210> SEQ ID NO 17
<211> LENGTH: 14
<212> TYPE: PRT
```

<213> ORGANISM: Glycine max

<400> SEQUENCE: 17

Arg Phe Tyr Leu Ala Gly Asn Gln Glu Gln Glu Phe Leu Lys
1               5                   10

<210> SEQ ID NO 18
<211> LENGTH: 7
<212> TYPE: PRT
<213> ORGANISM: Glycine max

<400> SEQUENCE: 18

Pro Pro Lys Glu Ser Gln Arg
1               5

<210> SEQ ID NO 19
<211> LENGTH: 9
<212> TYPE: PRT
<213> ORGANISM: Glycine max

<400> SEQUENCE: 19

Leu Ser Ala Gln Phe Gly Ser Leu Arg
1               5

<210> SEQ ID NO 20
<211> LENGTH: 13
<212> TYPE: PRT
<213> ORGANISM: Glycine max

<400> SEQUENCE: 20

Phe Tyr Leu Ala Gly Asn Gln Glu Gln Glu Phe Leu Gln
1               5                   10

<210> SEQ ID NO 21
<211> LENGTH: 7
<212> TYPE: PRT
<213> ORGANISM: Glycine max

<400> SEQUENCE: 21

Ser Lys Lys Thr Gln Pro Arg
1               5

<210> SEQ ID NO 22
<211> LENGTH: 13
<212> TYPE: PRT
<213> ORGANISM: Glycine max

<400> SEQUENCE: 22

Pro Ser Glu Val Leu Ala His Ser Tyr Asn Leu Ala Arg
1               5                   10

<210> SEQ ID NO 23
<211> LENGTH: 6
<212> TYPE: PRT
<213> ORGANISM: Glycine max

<400> SEQUENCE: 23

Ser Gly Asp Ala Leu Arg
1               5

<210> SEQ ID NO 24
<211> LENGTH: 6
<212> TYPE: PRT
<213> ORGANISM: Glycine max

```
<400> SEQUENCE: 24

Phe Glu Thr Leu Phe Lys
1               5

<210> SEQ ID NO 25
<211> LENGTH: 13
<212> TYPE: PRT
<213> ORGANISM: Glycine max

<400> SEQUENCE: 25

Lys Thr Ile Ser Ser Glu Asp Lys Pro Phe Asn Leu Arg
1               5                   10

<210> SEQ ID NO 26
<211> LENGTH: 8
<212> TYPE: PRT
<213> ORGANISM: Glycine max

<400> SEQUENCE: 26

Ser Pro Gln Leu Glu Asn Leu Arg
1               5

<210> SEQ ID NO 27
<211> LENGTH: 10
<212> TYPE: PRT
<213> ORGANISM: Glycine max

<400> SEQUENCE: 27

Leu Ala Gly Glu Lys Asp Asn Val Val Arg
1               5                   10

<210> SEQ ID NO 28
<211> LENGTH: 13
<212> TYPE: PRT
<213> ORGANISM: Glycine max

<400> SEQUENCE: 28

Lys Thr Ile Ser Ser Glu Asp Glu Pro Phe Asn Leu Arg
1               5                   10

<210> SEQ ID NO 29
<211> LENGTH: 12
<212> TYPE: PRT
<213> ORGANISM: Glycine max

<400> SEQUENCE: 29

Val Arg Glu Asp Glu Asn Asn Pro Phe Tyr Leu Arg
1               5                   10

<210> SEQ ID NO 30
<211> LENGTH: 8
<212> TYPE: PRT
<213> ORGANISM: Glycine max

<400> SEQUENCE: 30

Pro Pro Gln Glu Ser Gln Lys Arg
1               5

<210> SEQ ID NO 31
<211> LENGTH: 9
<212> TYPE: PRT
<213> ORGANISM: Glycine max

<400> SEQUENCE: 31
```

```
Leu Asn Ala Leu Lys Pro Asp Asn Arg
1               5
```

<210> SEQ ID NO 32
<211> LENGTH: 10
<212> TYPE: PRT
<213> ORGANISM: Glycine max

<400> SEQUENCE: 32

```
Val Phe Asp Gly Glu Leu Gln Glu Gly Arg
1               5                   10
```

<210> SEQ ID NO 33
<211> LENGTH: 12
<212> TYPE: PRT
<213> ORGANISM: Glycine max

<400> SEQUENCE: 33

```
Pro Glu Glu Val Ile Gln Gln Thr Phe Asn Leu Arg
1               5                   10
```

<210> SEQ ID NO 34
<211> LENGTH: 13
<212> TYPE: PRT
<213> ORGANISM: Glycine max

<400> SEQUENCE: 34

```
Ile Ser Thr Leu Asn Ser Leu Thr Leu Pro Ala Leu Arg
1               5                   10
```

<210> SEQ ID NO 35
<211> LENGTH: 16
<212> TYPE: PRT
<213> ORGANISM: Glycine max

<400> SEQUENCE: 35

```
Lys Gln Ile Val Thr Val Glu Gly Gly Leu Ser Val Ile Ser Pro Lys
1               5                   10                  15
```

<210> SEQ ID NO 36
<211> LENGTH: 11
<212> TYPE: PRT
<213> ORGANISM: Glycine max

<400> SEQUENCE: 36

```
Glu Gln Gln Glu Glu Gln Pro Leu Glu Val Arg
1               5                   10
```

<210> SEQ ID NO 37
<211> LENGTH: 15
<212> TYPE: PRT
<213> ORGANISM: Glycine max

<400> SEQUENCE: 37

```
Leu Gln Glu Ser Val Ile Val Glu Ile Ser Lys Glu Gln Ile Arg
1               5                   10                  15
```

<210> SEQ ID NO 38
<211> LENGTH: 5
<212> TYPE: PRT
<213> ORGANISM: Glycine max

<400> SEQUENCE: 38

```
Ser Ser Ser Arg Lys
1               5
```

```
<210> SEQ ID NO 39
<211> LENGTH: 8
<212> TYPE: PRT
<213> ORGANISM: Glycine max

<400> SEQUENCE: 39

Phe Phe Glu Ile Thr Pro Glu Lys
1               5

<210> SEQ ID NO 40
<211> LENGTH: 15
<212> TYPE: PRT
<213> ORGANISM: Glycine max

<400> SEQUENCE: 40

Val Leu Phe Ser Arg Glu Glu Gly Gln Gln Gln Gly Glu Gln Arg
1               5                   10                  15

<210> SEQ ID NO 41
<211> LENGTH: 14
<212> TYPE: PRT
<213> ORGANISM: Glycine max

<400> SEQUENCE: 41

Leu Lys Val Arg Glu Asp Glu Asn Asn Pro Phe Tyr Leu Arg
1               5                   10

<210> SEQ ID NO 42
<211> LENGTH: 4
<212> TYPE: PRT
<213> ORGANISM: Glycine max

<400> SEQUENCE: 42

Leu Leu Gln Arg
1

<210> SEQ ID NO 43
<211> LENGTH: 4
<212> TYPE: PRT
<213> ORGANISM: Glycine max

<400> SEQUENCE: 43

Phe Asn Lys Arg
1

<210> SEQ ID NO 44
<211> LENGTH: 4
<212> TYPE: PRT
<213> ORGANISM: Glycine max

<400> SEQUENCE: 44

Pro Asp Asn Arg
1

<210> SEQ ID NO 45
<211> LENGTH: 4
<212> TYPE: PRT
<213> ORGANISM: Glycine max

<400> SEQUENCE: 45

Thr Leu Asn Arg
1
```

```
<210> SEQ ID NO 46
<211> LENGTH: 4
<212> TYPE: PRT
<213> ORGANISM: Glycine max

<400> SEQUENCE: 46

Pro Gln Gln Arg
1

<210> SEQ ID NO 47
<211> LENGTH: 4
<212> TYPE: PRT
<213> ORGANISM: Glycine max

<400> SEQUENCE: 47

Tyr Asn Phe Arg
1

<210> SEQ ID NO 48
<211> LENGTH: 9
<212> TYPE: PRT
<213> ORGANISM: Glycine max

<400> SEQUENCE: 48

Pro Gln Asn Phe Val Val Ala Ala Arg
1               5

<210> SEQ ID NO 49
<211> LENGTH: 11
<212> TYPE: PRT
<213> ORGANISM: Glycine max

<400> SEQUENCE: 49

Leu Ala Gly Asn Gln Glu Gln Glu Phe Leu Lys
1               5                   10

<210> SEQ ID NO 50
<211> LENGTH: 5
<212> TYPE: PRT
<213> ORGANISM: Glycine max

<400> SEQUENCE: 50

Ser Gln Gln Ala Arg
1               5

<210> SEQ ID NO 51
<211> LENGTH: 7
<212> TYPE: PRT
<213> ORGANISM: Glycine max

<400> SEQUENCE: 51

Ala Asp Phe Tyr Asn Pro Lys
1               5

<210> SEQ ID NO 52
<211> LENGTH: 8
<212> TYPE: PRT
<213> ORGANISM: Glycine max

<400> SEQUENCE: 52

Met Ile Ile Ile Ala Gln Gly Lys
1               5

<210> SEQ ID NO 53
<211> LENGTH: 11
```

-continued

<212> TYPE: PRT
<213> ORGANISM: Glycine max

<400> SEQUENCE: 53

Pro Glu Thr Met Gln Gln Gln Gln Gln Lys
1               5                   10

<210> SEQ ID NO 54
<211> LENGTH: 4
<212> TYPE: PRT
<213> ORGANISM: Glycine max

<400> SEQUENCE: 54

His Ser Glu Arg
1

<210> SEQ ID NO 55
<211> LENGTH: 11
<212> TYPE: PRT
<213> ORGANISM: Glycine max

<400> SEQUENCE: 55

Tyr Glu Ala Gly Val Val Pro Pro Gly Ala Arg
1               5                   10

<210> SEQ ID NO 56
<211> LENGTH: 13
<212> TYPE: PRT
<213> ORGANISM: Glycine max

<400> SEQUENCE: 56

His His Leu Ala Glu Ala Ala Glu Tyr Val Gly Gln Lys
1               5                   10

<210> SEQ ID NO 57
<211> LENGTH: 11
<212> TYPE: PRT
<213> ORGANISM: Glycine max

<400> SEQUENCE: 57

Thr Lys Glu Val Gly Gln Asp Ile Gln Ser Lys
1               5                   10

<210> SEQ ID NO 58
<211> LENGTH: 5
<212> TYPE: PRT
<213> ORGANISM: Glycine max

<400> SEQUENCE: 58

Leu Val Val Ser Lys
1               5

<210> SEQ ID NO 59
<211> LENGTH: 8
<212> TYPE: PRT
<213> ORGANISM: Glycine max

<400> SEQUENCE: 59

Asp Ala Met Asp Gly Trp Phe Arg
1               5

<210> SEQ ID NO 60
<211> LENGTH: 12
<212> TYPE: PRT
<213> ORGANISM: Glycine max

```
<400> SEQUENCE: 60

Thr Ile Ser Ser Glu Asp Glu Pro Phe Asn Leu Arg
1               5                   10

<210> SEQ ID NO 61
<211> LENGTH: 13
<212> TYPE: PRT
<213> ORGANISM: Glycine max

<400> SEQUENCE: 61

Phe Phe Glu Ile Thr Pro Glu Lys Asn Pro Gln Leu Arg
1               5                   10

<210> SEQ ID NO 62
<211> LENGTH: 15
<212> TYPE: PRT
<213> ORGANISM: Glycine max

<400> SEQUENCE: 62

Ser Ser Asn Ser Phe Gln Thr Leu Phe Glu Asn Gln Asn Gly Arg
1               5                   10                  15

<210> SEQ ID NO 63
<211> LENGTH: 16
<212> TYPE: PRT
<213> ORGANISM: Glycine max

<400> SEQUENCE: 63

Gln Val Gln Glu Leu Ala Phe Pro Gly Ser Ala Gln Asp Val Glu Arg
1               5                   10                  15

<210> SEQ ID NO 64
<211> LENGTH: 11
<212> TYPE: PRT
<213> ORGANISM: Glycine max

<400> SEQUENCE: 64

Gln Gln Gln Glu Glu Gln Pro Leu Glu Val Arg
1               5                   10

<210> SEQ ID NO 65
<211> LENGTH: 12
<212> TYPE: PRT
<213> ORGANISM: Glycine max

<400> SEQUENCE: 65

Thr Ile Ser Ser Glu Asp Lys Pro Phe Asn Leu Arg
1               5                   10

<210> SEQ ID NO 66
<211> LENGTH: 10
<212> TYPE: PRT
<213> ORGANISM: Glycine max

<400> SEQUENCE: 66

Phe Leu Val Pro Pro Gln Glu Ser Gln Lys
1               5                   10

<210> SEQ ID NO 67
<211> LENGTH: 11
<212> TYPE: PRT
<213> ORGANISM: Glycine max

<400> SEQUENCE: 67
```

```
Phe Leu Val Pro Pro Gln Glu Ser Gln Lys Arg
1               5                   10
```

<210> SEQ ID NO 68
<211> LENGTH: 13
<212> TYPE: PRT
<213> ORGANISM: Glycine max

<400> SEQUENCE: 68

```
Val Leu Ile Val Pro Gln Asn Phe Val Val Ala Ala Arg
1               5                   10
```

<210> SEQ ID NO 69
<211> LENGTH: 17
<212> TYPE: PRT
<213> ORGANISM: Glycine max

<400> SEQUENCE: 69

```
Arg Pro Ser Tyr Thr Asn Gly Pro Gln Glu Ile Tyr Ile Gln Gln Gly
1               5                   10                  15
Lys
```

<210> SEQ ID NO 70
<211> LENGTH: 23
<212> TYPE: PRT
<213> ORGANISM: Glycine max

<400> SEQUENCE: 70

```
Val Phe Tyr Leu Ala Gly Asn Pro Asp Ile Glu Tyr Pro Glu Thr Met
1               5                   10                  15
Gln Gln Gln Gln Gln Gln Lys
            20
```

<210> SEQ ID NO 71
<211> LENGTH: 11
<212> TYPE: PRT
<213> ORGANISM: Glycine max

<400> SEQUENCE: 71

```
Glu Ala Phe Gly Val Asn Met Gln Ile Val Arg
1               5                   10
```

<210> SEQ ID NO 72
<211> LENGTH: 16
<212> TYPE: PRT
<213> ORGANISM: Glycine max

<400> SEQUENCE: 72

```
Asn Asn Asn Pro Phe Ser Phe Leu Val Pro Pro Gln Glu Ser Gln Arg
1               5                   10                  15
```

<210> SEQ ID NO 73
<211> LENGTH: 21
<212> TYPE: PRT
<213> ORGANISM: Glycine max

<400> SEQUENCE: 73

```
Asn Leu Gln Gly Glu Asn Glu Gly Glu Asp Gly Glu Asp Lys Gly Ala
1               5                   10                  15
Ile Val Thr Val Lys
            20
```

```
<210> SEQ ID NO 74
<211> LENGTH: 23
<212> TYPE: PRT
<213> ORGANISM: Glycine max

<400> SEQUENCE: 74

Val Phe Asp Gly Glu Leu Gln Glu Gly Gly Val Leu Ile Val Pro Gln
1               5                   10                  15

Asn Phe Ala Val Ala Ala Lys
            20

<210> SEQ ID NO 75
<211> LENGTH: 23
<212> TYPE: PRT
<213> ORGANISM: Glycine max

<400> SEQUENCE: 75

Gly Lys Gln Gln Glu Glu Asn Glu Gly Ser Asn Ile Leu Ser Gly
1               5                   10                  15

Phe Ala Pro Glu Phe Leu Lys
            20

<210> SEQ ID NO 76
<211> LENGTH: 9
<212> TYPE: PRT
<213> ORGANISM: Glycine max

<400> SEQUENCE: 76

Pro Gln Asn Phe Ala Val Ala Ala Lys
1               5

<210> SEQ ID NO 77
<211> LENGTH: 13
<212> TYPE: PRT
<213> ORGANISM: Glycine max

<400> SEQUENCE: 77

Asn Gly Leu His Leu Pro Ser Tyr Ser Pro Tyr Pro Arg
1               5                   10

<210> SEQ ID NO 78
<211> LENGTH: 14
<212> TYPE: PRT
<213> ORGANISM: Glycine max

<400> SEQUENCE: 78

Ala Ile Pro Ser Glu Val Leu Ala His Ser Tyr Asn Leu Arg
1               5                   10

<210> SEQ ID NO 79
<211> LENGTH: 26
<212> TYPE: PRT
<213> ORGANISM: Glycine max

<400> SEQUENCE: 79

Trp Gln Glu Gln Gln Asp Glu Asp Glu Asp Glu Asp Glu Asp Glu
1               5                   10                  15

Asp Glu Gln Ile Pro Ser His Pro Pro Arg
            20                  25

<210> SEQ ID NO 80
<211> LENGTH: 22
<212> TYPE: PRT
<213> ORGANISM: Glycine max
```

-continued

```
<400> SEQUENCE: 80

Lys Gln Gly Gln His Gln Gln Glu Glu Glu Glu Gly Gly Ser Val
1               5                   10                  15

Leu Ser Gly Phe Ser Lys
            20

<210> SEQ ID NO 81
<211> LENGTH: 15
<212> TYPE: PRT
<213> ORGANISM: Glycine max

<400> SEQUENCE: 81

Leu Phe Asp Gln Gln Asn Glu Gly Ser Ile Phe Ala Ile Ser Arg
1               5                   10                  15

<210> SEQ ID NO 82
<211> LENGTH: 16
<212> TYPE: PRT
<213> ORGANISM: Glycine max

<400> SEQUENCE: 82

Leu Thr Glu Val Gly Pro Asp Asp Glu Lys Ser Trp Leu Gln Arg
1               5                   10                  15

<210> SEQ ID NO 83
<211> LENGTH: 16
<212> TYPE: PRT
<213> ORGANISM: Glycine max

<400> SEQUENCE: 83

Thr Asn Arg Gly Pro Gly Gly Thr Ala Thr Ala His Asn Thr Arg Ala
1               5                   10                  15

<210> SEQ ID NO 84
<211> LENGTH: 17
<212> TYPE: PRT
<213> ORGANISM: Glycine max

<400> SEQUENCE: 84

His Gln Thr Ser Ala Met Pro Gly His Gly Thr Gly Gln Pro Thr Gly
1               5                   10                  15

His

<210> SEQ ID NO 85
<211> LENGTH: 6
<212> TYPE: PRT
<213> ORGANISM: Glycine max

<400> SEQUENCE: 85

Gly Tyr Leu Ala Asp Lys
1               5

<210> SEQ ID NO 86
<211> LENGTH: 6
<212> TYPE: PRT
<213> ORGANISM: Glycine max

<400> SEQUENCE: 86

Phe Gln Thr Leu Phe Glu
1               5

<210> SEQ ID NO 87
```

```
<211> LENGTH: 7
<212> TYPE: PRT
<213> ORGANISM: Glycine max

<400> SEQUENCE: 87

Pro Pro Gln Glu Ser Gln Lys
1               5

<210> SEQ ID NO 88
<211> LENGTH: 7
<212> TYPE: PRT
<213> ORGANISM: Glycine max

<400> SEQUENCE: 88

Pro Gln Glu Ser Gln Lys Arg
1               5

<210> SEQ ID NO 89
<211> LENGTH: 7
<212> TYPE: PRT
<213> ORGANISM: Glycine max

<400> SEQUENCE: 89

Asn Gln Tyr Gly Arg Ile Arg
1               5

<210> SEQ ID NO 90
<211> LENGTH: 8
<212> TYPE: PRT
<213> ORGANISM: Glycine max

<400> SEQUENCE: 90

Pro Glu Lys Asn Pro Gln Leu Arg
1               5

<210> SEQ ID NO 91
<211> LENGTH: 9
<212> TYPE: PRT
<213> ORGANISM: Glycine max

<400> SEQUENCE: 91

Glu Val Gly Gln Asp Ile Gln Ser Lys
1               5

<210> SEQ ID NO 92
<211> LENGTH: 9
<212> TYPE: PRT
<213> ORGANISM: Glycine max

<400> SEQUENCE: 92

Asp Tyr Gly Ser Tyr Ala Gln Gly Arg
1               5

<210> SEQ ID NO 93
<211> LENGTH: 9
<212> TYPE: PRT
<213> ORGANISM: Glycine max

<400> SEQUENCE: 93

Pro Pro Arg Tyr Glu Ala Gly Val Lys
1               5

<210> SEQ ID NO 94
<211> LENGTH: 9
<212> TYPE: PRT
```

<213> ORGANISM: Glycine max

<400> SEQUENCE: 94

Ala Pro Ser Ile Tyr His Ser Glu Arg
1               5

<210> SEQ ID NO 95
<211> LENGTH: 9
<212> TYPE: PRT
<213> ORGANISM: Glycine max

<400> SEQUENCE: 95

Phe Gly Val Asn Met Gln Ile Val Arg
1               5

<210> SEQ ID NO 96
<211> LENGTH: 10
<212> TYPE: PRT
<213> ORGANISM: Glycine max

<400> SEQUENCE: 96

Ser Ser Asp Phe Leu Thr Tyr Gly Leu Lys
1               5                   10

<210> SEQ ID NO 97
<211> LENGTH: 10
<212> TYPE: PRT
<213> ORGANISM: Glycine max

<400> SEQUENCE: 97

Ala Phe Gly Val Asn Met Gln Ile Val Arg
1               5                   10

<210> SEQ ID NO 98
<211> LENGTH: 10
<212> TYPE: PRT
<213> ORGANISM: Glycine max

<400> SEQUENCE: 98

Asn Ile Leu Glu Ala Ser Tyr Asp Thr Lys
1               5                   10

<210> SEQ ID NO 99
<211> LENGTH: 10
<212> TYPE: PRT
<213> ORGANISM: Glycine max

<400> SEQUENCE: 99

Asn Pro Ile Tyr Ser Asn Asn Phe Gly Lys
1               5                   10

<210> SEQ ID NO 100
<211> LENGTH: 11
<212> TYPE: PRT
<213> ORGANISM: Glycine max

<400> SEQUENCE: 100

Gly Ile Gly Thr Ile Ile Ser Ser Pro Tyr Arg
1               5                   10

<210> SEQ ID NO 101
<211> LENGTH: 10
<212> TYPE: PRT
<213> ORGANISM: Glycine max

```
<400> SEQUENCE: 101

Glu Ser Tyr Phe Val Asp Ala Gln Pro Lys
1               5                   10

<210> SEQ ID NO 102
<211> LENGTH: 10
<212> TYPE: PRT
<213> ORGANISM: Glycine max

<400> SEQUENCE: 102

His Leu Ser Val Val His Pro Ile Tyr Lys
1               5                   10

<210> SEQ ID NO 103
<211> LENGTH: 10
<212> TYPE: PRT
<213> ORGANISM: Glycine max

<400> SEQUENCE: 103

Leu His Glu Asn Ile Ala Arg Pro Ser Arg
1               5                   10

<210> SEQ ID NO 104
<211> LENGTH: 10
<212> TYPE: PRT
<213> ORGANISM: Glycine max

<400> SEQUENCE: 104

Asn Lys Pro Leu Val Val Gln Phe Gln Lys
1               5                   10

<210> SEQ ID NO 105
<211> LENGTH: 11
<212> TYPE: PRT
<213> ORGANISM: Glycine max

<400> SEQUENCE: 105

Ala Lys Asp Tyr Gly Ser Tyr Ala Gln Gly Arg
1               5                   10

<210> SEQ ID NO 106
<211> LENGTH: 11
<212> TYPE: PRT
<213> ORGANISM: Glycine max

<400> SEQUENCE: 106

Thr His His Asn Ala Val Thr Ser Tyr Leu Lys
1               5                   10

<210> SEQ ID NO 107
<211> LENGTH: 11
<212> TYPE: PRT
<213> ORGANISM: Glycine max

<400> SEQUENCE: 107

Leu Ala Gly Asn Gln Glu Gln Glu Phe Leu Gln
1               5                   10

<210> SEQ ID NO 108
<211> LENGTH: 11
<212> TYPE: PRT
<213> ORGANISM: Glycine max

<400> SEQUENCE: 108
```

Asn Lys Asn Pro Phe Leu Phe Gly Ser Asn Arg
1               5                   10

<210> SEQ ID NO 109
<211> LENGTH: 12
<212> TYPE: PRT
<213> ORGANISM: Glycine max

<400> SEQUENCE: 109

Ser Arg Asp Pro Ile Tyr Ser Asn Lys Leu Gly Lys
1               5                   10

<210> SEQ ID NO 110
<211> LENGTH: 12
<212> TYPE: PRT
<213> ORGANISM: Glycine max

<400> SEQUENCE: 110

Ser Arg Asn Pro Ile Tyr Ser Asn Asn Phe Gly Lys
1               5                   10

<210> SEQ ID NO 111
<211> LENGTH: 12
<212> TYPE: PRT
<213> ORGANISM: Glycine max

<400> SEQUENCE: 111

Tyr Leu Ala Gly Asn Gln Glu Gln Glu Phe Leu Lys
1               5                   10

<210> SEQ ID NO 112
<211> LENGTH: 12
<212> TYPE: PRT
<213> ORGANISM: Glycine max

<400> SEQUENCE: 112

Pro Glu Phe Leu Glu His Ala Phe Val Val Asp Arg
1               5                   10

<210> SEQ ID NO 113
<211> LENGTH: 13
<212> TYPE: PRT
<213> ORGANISM: Glycine max

<400> SEQUENCE: 113

Pro Pro His Ser Val Gln Val His Thr Thr Thr His Arg
1               5                   10

<210> SEQ ID NO 114
<211> LENGTH: 15
<212> TYPE: PRT
<213> ORGANISM: Glycine max

<400> SEQUENCE: 114

Gln Ile Val Thr Val Glu Gly Gly Leu Ser Val Ile Ser Pro Lys
1               5                   10                  15

<210> SEQ ID NO 115
<211> LENGTH: 13
<212> TYPE: PRT
<213> ORGANISM: Glycine max

<400> SEQUENCE: 115

Leu Pro Glu Glu Val Ile Gln His Thr Phe Asn Leu Lys
1               5                   10

```
<210> SEQ ID NO 116
<211> LENGTH: 13
<212> TYPE: PRT
<213> ORGANISM: Glycine max

<400> SEQUENCE: 116

Phe Ser Arg Glu Glu Gly Gln Gln Gln Gly Glu Gln Arg
1               5                   10

<210> SEQ ID NO 117
<211> LENGTH: 13
<212> TYPE: PRT
<213> ORGANISM: Glycine max

<400> SEQUENCE: 117

Asn Gln Arg Glu Ser Tyr Phe Val Asp Ala Gln Pro Lys
1               5                   10

<210> SEQ ID NO 118
<211> LENGTH: 13
<212> TYPE: PRT
<213> ORGANISM: Glycine max

<400> SEQUENCE: 118

Leu Phe Glu Ile Thr Pro Glu Lys Asn Pro Gln Leu Arg
1               5                   10

<210> SEQ ID NO 119
<211> LENGTH: 14
<212> TYPE: PRT
<213> ORGANISM: Glycine max

<400> SEQUENCE: 119

Gln Glu Ser Val Ile Val Glu Ile Ser Lys Glu Gln Ile Arg
1               5                   10

<210> SEQ ID NO 120
<211> LENGTH: 14
<212> TYPE: PRT
<213> ORGANISM: Glycine max

<400> SEQUENCE: 120

His Leu Ala Glu Ala Ala Glu Tyr Val Gly Gln Lys Thr Lys
1               5                   10

<210> SEQ ID NO 121
<211> LENGTH: 16
<212> TYPE: PRT
<213> ORGANISM: Glycine max

<400> SEQUENCE: 121

Ala Gly Arg Ile Ser Thr Leu Asn Ser Leu Thr Leu Pro Ala Leu Arg
1               5                   10                  15

<210> SEQ ID NO 122
<211> LENGTH: 14
<212> TYPE: PRT
<213> ORGANISM: Glycine max

<400> SEQUENCE: 122

Phe Met Pro Glu Lys Gly Ser Ala Glu Tyr Glu Glu Leu Arg
1               5                   10
```

```
<210> SEQ ID NO 123
<211> LENGTH: 14
<212> TYPE: PRT
<213> ORGANISM: Glycine max

<400> SEQUENCE: 123

Pro Phe Ser Phe Leu Val Pro Pro Gln Glu Ser Gln Arg Arg
1               5                   10

<210> SEQ ID NO 124
<211> LENGTH: 14
<212> TYPE: PRT
<213> ORGANISM: Glycine max

<400> SEQUENCE: 124

Leu Glu Ala Ser Tyr Asp Thr Lys Phe Glu Glu Ile Asn Lys
1               5                   10

<210> SEQ ID NO 125
<211> LENGTH: 16
<212> TYPE: PRT
<213> ORGANISM: Glycine max

<400> SEQUENCE: 125

Leu Ala Arg Pro Val Leu Gly Gly Ser Ser Thr Phe Pro Tyr Pro Arg
1               5                   10                  15

<210> SEQ ID NO 126
<211> LENGTH: 16
<212> TYPE: PRT
<213> ORGANISM: Glycine max

<400> SEQUENCE: 126

Asn Glu Leu Asp Lys Gly Ile Gly Thr Ile Ile Ser Ser Pro Tyr Arg
1               5                   10                  15

<210> SEQ ID NO 127
<211> LENGTH: 15
<212> TYPE: PRT
<213> ORGANISM: Glycine max

<400> SEQUENCE: 127

Thr His His Asn Ala Val Ser Ser Tyr Ile Lys Asp Val Phe Arg
1               5                   10                  15

<210> SEQ ID NO 128
<211> LENGTH: 15
<212> TYPE: PRT
<213> ORGANISM: Glycine max

<400> SEQUENCE: 128

Thr His His Asn Ala Val Thr Ser Tyr Leu Lys Asp Val Phe Arg
1               5                   10                  15

<210> SEQ ID NO 129
<211> LENGTH: 15
<212> TYPE: PRT
<213> ORGANISM: Glycine max

<400> SEQUENCE: 129

Asn Pro Phe Leu Phe Gly Ser Asn Arg Phe Glu Thr Leu Phe Lys
1               5                   10                  15

<210> SEQ ID NO 130
<211> LENGTH: 16
```

```
<212> TYPE: PRT
<213> ORGANISM: Glycine max

<400> SEQUENCE: 130

His Phe Leu Ala Gln Ser Phe Asn Thr Asn Glu Asp Ile Ala Glu Lys
1               5                   10                  15

<210> SEQ ID NO 131
<211> LENGTH: 16
<212> TYPE: PRT
<213> ORGANISM: Glycine max

<400> SEQUENCE: 131

Asn Asn Asn Pro Phe Ser Phe Leu Val Pro Pro Lys Glu Ser Gln Arg
1               5                   10                  15

<210> SEQ ID NO 132
<211> LENGTH: 15
<212> TYPE: PRT
<213> ORGANISM: Glycine max

<400> SEQUENCE: 132

Leu Phe Leu Leu Asp His His Asp Pro Ile Met Pro Tyr Leu Arg
1               5                   10                  15

<210> SEQ ID NO 133
<211> LENGTH: 17
<212> TYPE: PRT
<213> ORGANISM: Glycine max

<400> SEQUENCE: 133

Ser Leu Ser Gln Ile Val Gln Pro Ala Phe Glu Ser Ala Phe Asp Leu
1               5                   10                  15
Lys

<210> SEQ ID NO 134
<211> LENGTH: 16
<212> TYPE: PRT
<213> ORGANISM: Glycine max

<400> SEQUENCE: 134

Asp Trp Val Phe Thr Asp Gln Ala Leu Pro Ala Asp Leu Ile Lys Arg
1               5                   10                  15

<210> SEQ ID NO 135
<211> LENGTH: 18
<212> TYPE: PRT
<213> ORGANISM: Glycine max

<400> SEQUENCE: 135

Asn Leu Gln Gly Glu Asn Glu Gly Glu Asp Lys Gly Ala Ile Val Thr
1               5                   10                  15
Val Lys

<210> SEQ ID NO 136
<211> LENGTH: 16
<212> TYPE: PRT
<213> ORGANISM: Glycine max

<400> SEQUENCE: 136

Asn Ile Leu Glu Ala Ser Tyr Asp Thr Lys Phe Glu Glu Ile Asn Lys
1               5                   10                  15
```

```
<210> SEQ ID NO 137
<211> LENGTH: 18
<212> TYPE: PRT
<213> ORGANISM: Glycine max

<400> SEQUENCE: 137

Asn Leu Gln Gly Glu Asn Glu Glu Asp Ser Gly Ala Ile Val Thr
1               5                   10                  15

Val Lys

<210> SEQ ID NO 138
<211> LENGTH: 15
<212> TYPE: PRT
<213> ORGANISM: Glycine max

<400> SEQUENCE: 138

Lys Glu Ser Phe Phe Phe Pro Phe Glu Leu Pro Arg Glu Glu Arg
1               5                   10                  15

<210> SEQ ID NO 139
<211> LENGTH: 17
<212> TYPE: PRT
<213> ORGANISM: Glycine max

<400> SEQUENCE: 139

Ser Ser Asn Ser Phe Gln Thr Leu Phe Glu Asn Gln Asn Gly Arg Ile
1               5                   10                  15

Arg

<210> SEQ ID NO 140
<211> LENGTH: 17
<212> TYPE: PRT
<213> ORGANISM: Glycine max

<400> SEQUENCE: 140

Asn Asn Asn Pro Phe Ser Phe Leu Val Pro Pro Gln Glu Ser Gln Arg
1               5                   10                  15

Arg

<210> SEQ ID NO 141
<211> LENGTH: 19
<212> TYPE: PRT
<213> ORGANISM: Glycine max

<400> SEQUENCE: 141

Ala Ile Pro Ser Glu Val Leu Ser Asn Ser Tyr Asn Leu Gly Gln Ser
1               5                   10                  15

Gln Val Arg

<210> SEQ ID NO 142
<211> LENGTH: 18
<212> TYPE: PRT
<213> ORGANISM: Glycine max

<400> SEQUENCE: 142

His Phe Leu Ala Gln Ser Phe Asn Thr Asn Glu Asp Thr Ala Glu Lys
1               5                   10                  15

Leu Arg

<210> SEQ ID NO 143
<211> LENGTH: 19
<212> TYPE: PRT
```

<213> ORGANISM: Glycine max

<400> SEQUENCE: 143

Gln Val Gln Glu Leu Ala Phe Pro Gly Ser Ala Gln Asp Val Glu Arg
1               5                   10                  15

Leu Leu Lys

<210> SEQ ID NO 144
<211> LENGTH: 19
<212> TYPE: PRT
<213> ORGANISM: Glycine max

<400> SEQUENCE: 144

Val Pro Ser Gly Thr Thr Tyr Tyr Val Val Asn Pro Asp Asn Asn Glu
1               5                   10                  15

Asn Leu Arg

<210> SEQ ID NO 145
<211> LENGTH: 19
<212> TYPE: PRT
<213> ORGANISM: Glycine max

<400> SEQUENCE: 145

Ile Pro Ala Gly Thr Thr Tyr Tyr Leu Val Asn Pro His Asp His Gln
1               5                   10                  15

Asn Leu Lys

<210> SEQ ID NO 146
<211> LENGTH: 20
<212> TYPE: PRT
<213> ORGANISM: Glycine max

<400> SEQUENCE: 146

Gln Glu Glu Glu Asn Glu Gly Ser Asn Ile Leu Ser Gly Phe Ala Pro
1               5                   10                  15

Glu Phe Leu Lys
            20

<210> SEQ ID NO 147
<211> LENGTH: 21
<212> TYPE: PRT
<213> ORGANISM: Glycine max

<400> SEQUENCE: 147

Lys Gln Gly Gln His Gln Gln Glu Glu Glu Gly Gly Ser Val Leu
1               5                   10                  15

Ser Gly Phe Ser Lys
            20

<210> SEQ ID NO 148
<211> LENGTH: 22
<212> TYPE: PRT
<213> ORGANISM: Glycine max

<400> SEQUENCE: 148

Asn Leu Gln Gly Glu Asn Glu Glu Glu Asp Ser Gly Ala Ile Val Thr
1               5                   10                  15

Val Lys Gly Gly Leu Arg
            20

<210> SEQ ID NO 149

```
<211> LENGTH: 21
<212> TYPE: PRT
<213> ORGANISM: Glycine max

<400> SEQUENCE: 149

Ser Val Ser Gln Asn Val Leu Pro Leu Leu Gln Ser Ala Phe Asp Leu
1               5                   10                  15

Asn Phe Thr Pro Arg
            20

<210> SEQ ID NO 150
<211> LENGTH: 20
<212> TYPE: PRT
<213> ORGANISM: Glycine max

<400> SEQUENCE: 150

Gln Val Lys Asn Asn Pro Phe Ser Phe Leu Val Pro Pro Gln Glu
1               5                   10                  15

Ser Gln Arg Arg
            20

<210> SEQ ID NO 151
<211> LENGTH: 21
<212> TYPE: PRT
<213> ORGANISM: Glycine max

<400> SEQUENCE: 151

Gln Val Lys Asn Asn Pro Phe Ser Phe Leu Val Pro Pro Gln Glu
1               5                   10                  15

Ser Gln Arg Arg Ala
            20

<210> SEQ ID NO 152
<211> LENGTH: 22
<212> TYPE: PRT
<213> ORGANISM: Glycine max

<400> SEQUENCE: 152

Asn Ala Met Phe Val Pro His Tyr Thr Leu Asn Ala Asn Ser Ile Ile
1               5                   10                  15

Tyr Ala Leu Asn Gly Arg
            20

<210> SEQ ID NO 153
<211> LENGTH: 23
<212> TYPE: PRT
<213> ORGANISM: Glycine max

<400> SEQUENCE: 153

Thr Pro Val Val Ala Val Ser Ile Ile Asp Thr Asn Ser Leu Glu Asn
1               5                   10                  15

Gln Leu Asp Gln Met Pro Arg
            20

<210> SEQ ID NO 154
<211> LENGTH: 23
<212> TYPE: PRT
<213> ORGANISM: Glycine max

<400> SEQUENCE: 154

Val Phe Asp Gly Glu Leu Gln Glu Gly Arg Val Leu Ile Val Pro Gln
1               5                   10                  15
```

Asn Phe Val Val Ala Ala Arg
            20

<210> SEQ ID NO 155
<211> LENGTH: 23
<212> TYPE: PRT
<213> ORGANISM: Glycine max

<400> SEQUENCE: 155

Glu Pro Val Val Ala Ile Ser Leu Leu Asp Thr Ser Asn Phe Asn Asn
1               5                   10                  15

Gln Leu Asp Gln Thr Pro Arg
            20

<210> SEQ ID NO 156
<211> LENGTH: 23
<212> TYPE: PRT
<213> ORGANISM: Glycine max

<400> SEQUENCE: 156

Lys Asn Ala Met Phe Val Pro His Tyr Thr Leu Asn Ala Asn Ser Ile
1               5                   10                  15

Ile Tyr Ala Leu Asn Gly Arg
            20

<210> SEQ ID NO 157
<211> LENGTH: 24
<212> TYPE: PRT
<213> ORGANISM: Glycine max

<400> SEQUENCE: 157

Asp Leu Asp Ile Phe Leu Ser Ile Val Asp Met Asn Glu Gly Ala Leu
1               5                   10                  15

Leu Leu Pro His Phe Asn Ser Lys
            20

<210> SEQ ID NO 158
<211> LENGTH: 23
<212> TYPE: PRT
<213> ORGANISM: Glycine max

<400> SEQUENCE: 158

Val Phe Tyr Leu Ala Gly Asn Pro Asp Ile Glu His Pro Glu Thr Met
1               5                   10                  15

Gln Gln Gln Gln Gln Gln Lys
            20

<210> SEQ ID NO 159
<211> LENGTH: 24
<212> TYPE: PRT
<213> ORGANISM: Glycine max

<400> SEQUENCE: 159

His Phe Leu Ala Gln Ser Phe Asn Thr Asn Glu Asp Ile Ala Glu Lys
1               5                   10                  15

Leu Gln Ser Pro Asp Asp Glu Arg
            20

<210> SEQ ID NO 160
<211> LENGTH: 27
<212> TYPE: PRT
<213> ORGANISM: Glycine max

```
<400> SEQUENCE: 160

Leu Val Phe Cys Pro Gln Gln Ala Glu Asp Asp Lys Cys Gly Asp Ile
1               5                   10                  15

Gly Ile Ser Ile Asp His Asp Asp Gly Thr Arg
            20                  25

<210> SEQ ID NO 161
<211> LENGTH: 25
<212> TYPE: PRT
<213> ORGANISM: Glycine max

<400> SEQUENCE: 161

Ser Gln Gln Ala Arg Gln Val Lys Asn Asn Asn Pro Phe Ser Phe Leu
1               5                   10                  15

Val Pro Pro Gln Glu Ser Gln Arg Arg
            20                  25

<210> SEQ ID NO 162
<211> LENGTH: 25
<212> TYPE: PRT
<213> ORGANISM: Glycine max

<400> SEQUENCE: 162

Val Leu Phe Gly Glu Glu Glu Gln Arg Gln Gln Glu Gly Val Ile
1               5                   10                  15

Val Glu Leu Ser Lys Glu Gln Ile Arg
            20                  25

<210> SEQ ID NO 163
<211> LENGTH: 29
<212> TYPE: PRT
<213> ORGANISM: Glycine max

<400> SEQUENCE: 163

Asn Leu Gln Gly Glu Asn Glu Glu Asp Ser Gly Ala Ile Val Thr
1               5                   10                  15

Val Lys Gly Gly Leu Arg Val Thr Ala Pro Ala Met Arg
            20                  25

<210> SEQ ID NO 164
<211> LENGTH: 28
<212> TYPE: PRT
<213> ORGANISM: Glycine max

<400> SEQUENCE: 164

Val Phe Tyr Leu Ala Gly Asn Pro Asp Ile Glu Tyr Pro Glu Thr Met
1               5                   10                  15

Gln Gln Gln Gln Gln Lys Ser His Gly Gly Arg
            20                  25

<210> SEQ ID NO 165
<211> LENGTH: 30
<212> TYPE: PRT
<213> ORGANISM: Glycine max

<400> SEQUENCE: 165

Asp Phe Val Leu Asp Asn Glu Gly Asn Pro Leu Glu Asn Gly Gly Thr
1               5                   10                  15

Tyr Tyr Ile Leu Ser Asp Ile Thr Ala Phe Gly Gly Ile Arg
            20                  25                  30
```

```
<210> SEQ ID NO 166
<211> LENGTH: 29
<212> TYPE: PRT
<213> ORGANISM: Glycine max

<400> SEQUENCE: 166

His Gln Gln Glu Glu Glu Asn Glu Gly Gly Ser Ile Leu Ser Gly Phe
 1               5                  10                  15

Thr Leu Glu Phe Leu Glu His Ala Phe Ser Val Asp Lys
            20                  25

<210> SEQ ID NO 167
<211> LENGTH: 29
<212> TYPE: PRT
<213> ORGANISM: Glycine max

<400> SEQUENCE: 167

Arg Gln Gln Glu Glu Glu Asn Glu Gly Gly Ser Ile Leu Ser Gly Phe
 1               5                  10                  15

Ala Pro Glu Phe Leu Glu His Ala Phe Val Val Asp Arg
            20                  25

<210> SEQ ID NO 168
<211> LENGTH: 32
<212> TYPE: PRT
<213> ORGANISM: Glycine max

<400> SEQUENCE: 168

Thr Asn Asp Thr Pro Met Ile Gly Thr Leu Ala Gly Ala Asn Ser Leu
 1               5                  10                  15

Leu Asn Ala Leu Pro Glu Glu Val Ile Gln His Thr Phe Asn Leu Lys
            20                  25                  30

<210> SEQ ID NO 169
<211> LENGTH: 34
<212> TYPE: PRT
<213> ORGANISM: Glycine max

<400> SEQUENCE: 169

His Asn Ile Gly Gln Thr Ser Ser Pro Asp Ile Tyr Asn Pro Gln Ala
 1               5                  10                  15

Gly Ser Val Thr Thr Ala Thr Ser Leu Asp Phe Pro Ala Leu Ser Trp
            20                  25                  30

Leu Arg

<210> SEQ ID NO 170
<211> LENGTH: 33
<212> TYPE: PRT
<213> ORGANISM: Glycine max

<400> SEQUENCE: 170

His Gln Gln Glu Glu Glu Asn Glu Gly Gly Ser Ile Leu Ser Gly Phe
 1               5                  10                  15

Thr Leu Glu Phe Leu Glu His Ala Phe Ser Val Asp Lys Gln Ile Ala
            20                  25                  30

Lys

<210> SEQ ID NO 171
<211> LENGTH: 35
<212> TYPE: PRT
<213> ORGANISM: Glycine max
```

-continued

<400> SEQUENCE: 171

Asn Phe Leu Ala Gly Ser Gln Asp Asn Val Ile Ser Gln Ile Pro Ser
1               5                   10                  15

Gln Val Gln Glu Leu Ala Phe Pro Gly Ser Ala Gln Ala Val Glu Lys
            20                  25                  30

Leu Leu Lys
        35

<210> SEQ ID NO 172
<211> LENGTH: 34
<212> TYPE: PRT
<213> ORGANISM: Glycine max

<400> SEQUENCE: 172

Met Ile Thr Leu Ala Ile Pro Val Asn Lys Pro Gly Arg Phe Glu Ser
1               5                   10                  15

Phe Phe Leu Ser Ser Thr Gln Ala Gln Gln Ser Tyr Leu Gln Gly Phe
            20                  25                  30

Ser Lys

<210> SEQ ID NO 173
<211> LENGTH: 45
<212> TYPE: PRT
<213> ORGANISM: Glycine max

<400> SEQUENCE: 173

Phe Arg Glu Gly Asp Leu Ile Ala Val Pro Thr Gly Val Ala Trp Trp
1               5                   10                  15

Met Tyr Asn Asn Glu Asp Thr Pro Val Val Ala Val Ser Ile Ile Asp
            20                  25                  30

Thr Asn Ser Leu Glu Asn Gln Leu Asp Gln Met Pro Arg
        35                  40                  45

<210> SEQ ID NO 174
<211> LENGTH: 11
<212> TYPE: PRT
<213> ORGANISM: Glycine max

<400> SEQUENCE: 174

Glu Ala Phe Gly Val Asn Met Gln Ile Val Arg
1               5                   10

<210> SEQ ID NO 175
<211> LENGTH: 12
<212> TYPE: PRT
<213> ORGANISM: Glycine max

<400> SEQUENCE: 175

Ile Ser Pro Leu Pro Val Leu Lys Glu Ile Phe Arg
1               5                   10

<210> SEQ ID NO 176
<211> LENGTH: 15
<212> TYPE: PRT
<213> ORGANISM: Glycine max

<400> SEQUENCE: 176

Tyr Glu Ala Gly Val Val Pro Pro Ala Arg Phe Glu Ala Pro Arg
1               5                   10                  15

<210> SEQ ID NO 177

```
<211> LENGTH: 22
<212> TYPE: PRT
<213> ORGANISM: Glycine max

<400> SEQUENCE: 177

Asn Ala Met Phe Val Pro His Tyr Asn Leu Asn Ala Asn Ser Ile Ile
1               5                   10                  15

Tyr Ala Leu Asn Gly Arg
            20

<210> SEQ ID NO 178
<211> LENGTH: 10
<212> TYPE: PRT
<213> ORGANISM: Bos taurus

<400> SEQUENCE: 178

Tyr Ile Pro Ile Gln Tyr Val Leu Ser Arg
1               5                   10

<210> SEQ ID NO 179
<211> LENGTH: 10
<212> TYPE: PRT
<213> ORGANISM: Bos taurus

<400> SEQUENCE: 179

Tyr Leu Gly Tyr Leu Glu Gln Leu Leu Arg
1               5                   10

<210> SEQ ID NO 180
<211> LENGTH: 11
<212> TYPE: PRT
<213> ORGANISM: Bos taurus

<400> SEQUENCE: 180

His Ile Gln Lys Glu Asp Val Pro Ser Glu Arg
1               5                   10

<210> SEQ ID NO 181
<211> LENGTH: 12
<212> TYPE: PRT
<213> ORGANISM: Bos taurus

<400> SEQUENCE: 181

Phe Phe Val Ala Pro Phe Pro Glu Val Phe Gly Lys
1               5                   10

<210> SEQ ID NO 182
<211> LENGTH: 13
<212> TYPE: PRT
<213> ORGANISM: Bos taurus

<400> SEQUENCE: 182

Phe Val Ala Pro Phe Pro Glu Val Phe Gly Lys Glu Lys
1               5                   10

<210> SEQ ID NO 183
<211> LENGTH: 13
<212> TYPE: PRT
<213> ORGANISM: Bos taurus

<400> SEQUENCE: 183

His Pro His Leu Ser Phe Met Ala Ile Pro Pro Lys Lys
1               5                   10
```

```
<210> SEQ ID NO 184
<211> LENGTH: 12
<212> TYPE: PRT
<213> ORGANISM: Bos taurus

<400> SEQUENCE: 184

Tyr Leu Gly Tyr Leu Glu Gln Leu Leu Arg Leu Lys
1               5                   10

<210> SEQ ID NO 185
<211> LENGTH: 13
<212> TYPE: PRT
<213> ORGANISM: Bos taurus

<400> SEQUENCE: 185

Ile Ala Lys Tyr Ile Pro Ile Gln Tyr Val Leu Ser Arg
1               5                   10

<210> SEQ ID NO 186
<211> LENGTH: 14
<212> TYPE: PRT
<213> ORGANISM: Bos taurus

<400> SEQUENCE: 186

His Pro His Pro His Leu Ser Phe Met Ala Ile Pro Pro Lys
1               5                   10

<210> SEQ ID NO 187
<211> LENGTH: 14
<212> TYPE: PRT
<213> ORGANISM: Bos taurus

<400> SEQUENCE: 187

Phe Phe Val Ala Pro Phe Pro Glu Val Phe Gly Lys Glu Lys
1               5                   10

<210> SEQ ID NO 188
<211> LENGTH: 15
<212> TYPE: PRT
<213> ORGANISM: Bos taurus

<400> SEQUENCE: 188

His Pro His Pro His Leu Ser Phe Met Ala Ile Pro Pro Lys Lys
1               5                   10                  15

<210> SEQ ID NO 189
<211> LENGTH: 15
<212> TYPE: PRT
<213> ORGANISM: Bos taurus

<400> SEQUENCE: 189

His Gln Gly Leu Pro Gln Glu Val Leu Asn Glu Asn Leu Leu Arg
1               5                   10                  15

<210> SEQ ID NO 190
<211> LENGTH: 18
<212> TYPE: PRT
<213> ORGANISM: Bos taurus

<400> SEQUENCE: 190

Ser Pro Ala Gln Ile Leu Gln Trp Gln Val Leu Ser Asn Thr Val Pro
1               5                   10                  15

Ala Lys
```

```
<210> SEQ ID NO 191
<211> LENGTH: 19
<212> TYPE: PRT
<213> ORGANISM: Bos taurus

<400> SEQUENCE: 191

His Pro His Pro His Leu Ser Phe Met Ala Ile Pro Pro Lys Lys Asn
1               5                   10                  15

Gln Asp Lys

<210> SEQ ID NO 192
<211> LENGTH: 19
<212> TYPE: PRT
<213> ORGANISM: Bos taurus

<400> SEQUENCE: 192

His Pro Ile Lys His Gln Gly Leu Pro Gln Glu Val Leu Asn Glu Asn
1               5                   10                  15

Leu Leu Arg

<210> SEQ ID NO 193
<211> LENGTH: 22
<212> TYPE: PRT
<213> ORGANISM: Bos taurus

<400> SEQUENCE: 193

Arg Pro Lys His Pro Ile Lys His Gln Gly Leu Pro Gln Glu Val Leu
1               5                   10                  15

Asn Glu Asn Leu Leu Arg
            20

<210> SEQ ID NO 194
<211> LENGTH: 27
<212> TYPE: PRT
<213> ORGANISM: Bos taurus

<400> SEQUENCE: 194

Tyr Tyr Gln Gln Lys Pro Val Ala Leu Ile Asn Asn Gln Phe Leu Pro
1               5                   10                  15

Tyr Pro Tyr Tyr Ala Lys Pro Ala Ala Val Arg
            20                  25

<210> SEQ ID NO 195
<211> LENGTH: 32
<212> TYPE: PRT
<213> ORGANISM: Bos taurus

<400> SEQUENCE: 195

Leu His Ser Met Lys Glu Gly Ile His Ala Gln Gln Lys Glu Pro Met
1               5                   10                  15

Ile Gly Val Asn Gln Glu Leu Ala Tyr Phe Tyr Pro Glu Leu Phe Arg
            20                  25                  30

<210> SEQ ID NO 196
<211> LENGTH: 34
<212> TYPE: PRT
<213> ORGANISM: Bos taurus

<400> SEQUENCE: 196

Leu Ile Thr Leu Ala Ile Pro Val Asn Lys Pro Gly Arg Phe Glu Ser
1               5                   10                  15

Phe Phe Leu Ser Ser Thr Glu Ala Gln Gln Ser Tyr Leu Gln Gly Phe
```

-continued

```
                    20                  25                  30

Ser Arg

<210> SEQ ID NO 197
<211> LENGTH: 34
<212> TYPE: PRT
<213> ORGANISM: Bos taurus

<400> SEQUENCE: 197

Tyr Pro Ser Tyr Gly Leu Asn Tyr Tyr Gln Gln Lys Pro Val Ala Leu
1               5                   10                  15

Ile Asn Asn Gln Phe Leu Pro Tyr Pro Tyr Ala Lys Pro Ala Ala
            20                  25                  30

Val Arg

<210> SEQ ID NO 198
<211> LENGTH: 8
<212> TYPE: PRT
<213> ORGANISM: Brassica juncea

<400> SEQUENCE: 198

Gln Thr Ala Thr His Leu Pro Arg
1               5

<210> SEQ ID NO 199
<211> LENGTH: 8
<212> TYPE: PRT
<213> ORGANISM: Brassica juncea

<400> SEQUENCE: 199

Leu Gln Asn Gln Gln Val Asn Arg
1               5

<210> SEQ ID NO 200
<211> LENGTH: 9
<212> TYPE: PRT
<213> ORGANISM: Brassica juncea

<400> SEQUENCE: 200

Tyr Gln Thr Ala Thr His Leu Pro Arg
1               5

<210> SEQ ID NO 201
<211> LENGTH: 10
<212> TYPE: PRT
<213> ORGANISM: Brassica juncea

<400> SEQUENCE: 201

Gly Pro Phe Gln Val Val Arg Pro Pro Leu
1               5                   10

<210> SEQ ID NO 202
<211> LENGTH: 11
<212> TYPE: PRT
<213> ORGANISM: Brassica juncea

<400> SEQUENCE: 202

Met Ala Asp Ala Val Gly Tyr Ala Gly Gln Lys
1               5                   10

<210> SEQ ID NO 203
<211> LENGTH: 9
<212> TYPE: PRT
```

<213> ORGANISM: Brassica juncea

<400> SEQUENCE: 203

Glu Phe Gln Gln Ala Gln His Leu Arg
1               5

<210> SEQ ID NO 204
<211> LENGTH: 9
<212> TYPE: PRT
<213> ORGANISM: Brassica juncea

<400> SEQUENCE: 204

Asn Asn Phe Glu Trp Ile Ser Phe Lys
1               5

<210> SEQ ID NO 205
<211> LENGTH: 11
<212> TYPE: PRT
<213> ORGANISM: Brassica juncea

<400> SEQUENCE: 205

Gly Ala Ser Lys Ala Val Lys Gln Gln Ile Arg
1               5                   10

<210> SEQ ID NO 206
<211> LENGTH: 11
<212> TYPE: PRT
<213> ORGANISM: Brassica juncea

<400> SEQUENCE: 206

Val Gln Gly Gln Phe Gly Val Ile Arg Pro Pro
1               5                   10

<210> SEQ ID NO 207
<211> LENGTH: 10
<212> TYPE: PRT
<213> ORGANISM: Brassica juncea

<400> SEQUENCE: 207

Ile Tyr Gln Thr Ala Thr His Leu Pro Arg
1               5                   10

<210> SEQ ID NO 208
<211> LENGTH: 13
<212> TYPE: PRT
<213> ORGANISM: Brassica juncea

<400> SEQUENCE: 208

Met Ala Asp Ala Val Gly Tyr Ala Gly Gln Lys Gly Lys
1               5                   10

<210> SEQ ID NO 209
<211> LENGTH: 12
<212> TYPE: PRT
<213> ORGANISM: Brassica juncea

<400> SEQUENCE: 209

Val Gln Gly Pro Phe Ser Val Ile Arg Pro Pro Leu
1               5                   10

<210> SEQ ID NO 210
<211> LENGTH: 12
<212> TYPE: PRT
<213> ORGANISM: Brassica juncea

```
<400> SEQUENCE: 210

Val Gln Gly Gln Phe Gly Val Ile Arg Pro Pro Leu
1               5                   10

<210> SEQ ID NO 211
<211> LENGTH: 12
<212> TYPE: PRT
<213> ORGANISM: Brassica juncea

<400> SEQUENCE: 211

Gly Leu Tyr Leu Pro Ser Phe Phe Ser Thr Ala Lys
1               5                   10

<210> SEQ ID NO 212
<211> LENGTH: 13
<212> TYPE: PRT
<213> ORGANISM: Brassica juncea

<400> SEQUENCE: 212

Thr Asn Ala Asn Ala Gln Ile Asn Thr Leu Ala Gly Arg
1               5                   10

<210> SEQ ID NO 213
<211> LENGTH: 13
<212> TYPE: PRT
<213> ORGANISM: Brassica juncea

<400> SEQUENCE: 213

Ile Ser Tyr Val Val Gln Gly Met Gly Ile Ser Gly Arg
1               5                   10

<210> SEQ ID NO 214
<211> LENGTH: 13
<212> TYPE: PRT
<213> ORGANISM: Brassica juncea

<400> SEQUENCE: 214

Asn Ile Leu Asn Gly Phe Thr Pro Glu Val Leu Ala Lys
1               5                   10

<210> SEQ ID NO 215
<211> LENGTH: 12
<212> TYPE: PRT
<213> ORGANISM: Brassica juncea

<400> SEQUENCE: 215

Thr Ala Gln Gln Leu Gln Asn Gln Gln Asp Asn Arg
1               5                   10

<210> SEQ ID NO 216
<211> LENGTH: 14
<212> TYPE: PRT
<213> ORGANISM: Brassica juncea

<400> SEQUENCE: 216

Arg Met Ala Asp Ala Val Gly Tyr Ala Gly Gln Lys Gly Lys
1               5                   10

<210> SEQ ID NO 217
<211> LENGTH: 12
<212> TYPE: PRT
<213> ORGANISM: Brassica juncea

<400> SEQUENCE: 217
```

-continued

Ala Thr Ser Gln Gln Phe Gln Trp Ile Glu Phe Lys
1               5                   10

<210> SEQ ID NO 218
<211> LENGTH: 14
<212> TYPE: PRT
<213> ORGANISM: Brassica juncea

<400> SEQUENCE: 218

Ala Gly Asn Asn Pro Gln Gly Gln Gln Trp Leu Gln Gly Arg
1               5                   10

<210> SEQ ID NO 219
<211> LENGTH: 15
<212> TYPE: PRT
<213> ORGANISM: Brassica juncea

<400> SEQUENCE: 219

Gly Gln Leu Leu Val Val Pro Gln Gly Phe Ala Val Val Lys Arg
1               5                   10                  15

<210> SEQ ID NO 220
<211> LENGTH: 15
<212> TYPE: PRT
<213> ORGANISM: Brassica juncea

<400> SEQUENCE: 220

Thr Leu Leu Phe Gly Glu Lys Pro Val Thr Val Phe Gly Ile Arg
1               5                   10                  15

<210> SEQ ID NO 221
<211> LENGTH: 16
<212> TYPE: PRT
<213> ORGANISM: Brassica juncea

<400> SEQUENCE: 221

Leu Leu Ala Gly Asn Asn Pro Gln Gly Gln Gln Trp Leu Gln Gly Arg
1               5                   10                  15

<210> SEQ ID NO 222
<211> LENGTH: 16
<212> TYPE: PRT
<213> ORGANISM: Brassica juncea

<400> SEQUENCE: 222

Val Thr Ser Val Asn Ser Tyr Thr Leu Pro Ile Leu Gln Tyr Ile Arg
1               5                   10                  15

<210> SEQ ID NO 223
<211> LENGTH: 15
<212> TYPE: PRT
<213> ORGANISM: Brassica juncea

<400> SEQUENCE: 223

Met Asn Gln Phe Phe His Gly Trp Tyr Met Glu Pro Leu Thr Lys
1               5                   10                  15

<210> SEQ ID NO 224
<211> LENGTH: 17
<212> TYPE: PRT
<213> ORGANISM: Brassica juncea

<400> SEQUENCE: 224

Thr Ala Gln Gln Leu Gln Asn Gln Gln Asp Asn Arg Gly Asn Ile Val
1               5                   10                  15

Arg

<210> SEQ ID NO 225
<211> LENGTH: 18
<212> TYPE: PRT
<213> ORGANISM: Brassica juncea

<400> SEQUENCE: 225

Pro Phe Leu Leu Ala Gly Asn Asn Pro Gln Gly Gln Gln Trp Leu Gln
1               5                   10                  15

Gly Arg

<210> SEQ ID NO 226
<211> LENGTH: 19
<212> TYPE: PRT
<213> ORGANISM: Brassica juncea

<400> SEQUENCE: 226

Phe Gly Ile Val Glu Gly Leu Met Thr Thr Val His Ser Ile Thr Ala
1               5                   10                  15

Thr Gln Lys

<210> SEQ ID NO 227
<211> LENGTH: 19
<212> TYPE: PRT
<213> ORGANISM: Brassica juncea

<400> SEQUENCE: 227

Gly Leu Pro Leu Glu Val Ile Ser Asn Gly Tyr Gln Ile Ser Pro Gln
1               5                   10                  15

Glu Ala Arg

<210> SEQ ID NO 228
<211> LENGTH: 18
<212> TYPE: PRT
<213> ORGANISM: Brassica juncea

<400> SEQUENCE: 228

Trp Phe Leu Pro Phe Asp Glu Ser Asp Pro Ala Ser Ile Glu Ala Ala
1               5                   10                  15

Glu Arg

<210> SEQ ID NO 229
<211> LENGTH: 19
<212> TYPE: PRT
<213> ORGANISM: Brassica juncea

<400> SEQUENCE: 229

Gly Leu Pro Leu Glu Val Ile Ser Asn Gly Tyr Gln Ile Ser Leu Glu
1               5                   10                  15

Glu Ala Arg

<210> SEQ ID NO 230
<211> LENGTH: 19
<212> TYPE: PRT
<213> ORGANISM: Brassica juncea

<400> SEQUENCE: 230

Ala Leu Pro Leu Glu Val Ile Thr Asn Ala Phe Gln Ile Ser Leu Glu
1               5                   10                  15

Glu Ala Arg

<210> SEQ ID NO 231
<211> LENGTH: 19
<212> TYPE: PRT
<213> ORGANISM: Brassica juncea

<400> SEQUENCE: 231

Gln Gln Gly Gln Gln Gln Gly Gln Gln Gly Gln Gln Leu Gln His Glu
1               5                   10                  15

Ile Ser Arg

<210> SEQ ID NO 232
<211> LENGTH: 21
<212> TYPE: PRT
<213> ORGANISM: Brassica juncea

<400> SEQUENCE: 232

Asn Phe Gly Lys Asp Phe Ile Phe Gly Val Ala Ser Ser Ala Tyr Gln
1               5                   10                  15

Ile Glu Gly Gly Arg
            20

<210> SEQ ID NO 233
<211> LENGTH: 20
<212> TYPE: PRT
<213> ORGANISM: Brassica juncea

<400> SEQUENCE: 233

Ala Leu Pro Leu Glu Val Ile Thr Asn Ala Phe Gln Ile Ser Leu Glu
1               5                   10                  15

Glu Ala Arg Arg
            20

<210> SEQ ID NO 234
<211> LENGTH: 20
<212> TYPE: PRT
<213> ORGANISM: Brassica juncea

<400> SEQUENCE: 234

Thr His Glu Asn Ile Asp Asp Pro Ala Arg Ala Asp Val Tyr Lys Pro
1               5                   10                  15

Asn Leu Gly Arg
            20

<210> SEQ ID NO 235
<211> LENGTH: 21
<212> TYPE: PRT
<213> ORGANISM: Brassica juncea

<400> SEQUENCE: 235

Phe Asn Thr Ile Glu Thr Thr Leu Thr His Ser Ser Gly Pro Ala Ser
1               5                   10                  15

Tyr Gly Arg Pro Arg
            20

<210> SEQ ID NO 236
<211> LENGTH: 21
<212> TYPE: PRT
<213> ORGANISM: Brassica juncea

<400> SEQUENCE: 236

```
Asn Leu Arg Pro Phe Leu Leu Ala Gly Asn Asn Pro Gln Gly Gln Gln
1               5                   10                  15

Trp Leu Gln Gly Arg
            20

<210> SEQ ID NO 237
<211> LENGTH: 23
<212> TYPE: PRT
<213> ORGANISM: Brassica juncea

<400> SEQUENCE: 237

Val Phe Asp Gln Glu Ile Ser Lys Gly Gln Leu Leu Val Val Pro Gln
1               5                   10                  15

Gly Phe Ala Val Val Lys Arg
            20

<210> SEQ ID NO 238
<211> LENGTH: 9
<212> TYPE: PRT
<213> ORGANISM: Zea mays

<400> SEQUENCE: 238

Val Ala Val Leu Glu Ala Asn Pro Arg
1               5

<210> SEQ ID NO 239
<211> LENGTH: 8
<212> TYPE: PRT
<213> ORGANISM: Zea mays

<400> SEQUENCE: 239

Arg Pro Tyr Val Phe Asp Arg Arg
1               5

<210> SEQ ID NO 240
<211> LENGTH: 10
<212> TYPE: PRT
<213> ORGANISM: Zea mays

<400> SEQUENCE: 240

His Gly Gln Asp Lys Gly Ile Ile Val Arg
1               5                   10

<210> SEQ ID NO 241
<211> LENGTH: 12
<212> TYPE: PRT
<213> ORGANISM: Zea mays

<400> SEQUENCE: 241

Ala Ile Gly Phe Asp Gly Leu Gly Asp Pro Gly Arg
1               5                   10

<210> SEQ ID NO 242
<211> LENGTH: 10
<212> TYPE: PRT
<213> ORGANISM: Zea mays

<400> SEQUENCE: 242

Val Leu Arg Pro Phe Asp Glu Val Ser Arg
1               5                   10

<210> SEQ ID NO 243
<211> LENGTH: 11
<212> TYPE: PRT
```

<213> ORGANISM: Zea mays

<400> SEQUENCE: 243

Asn Pro Glu Ser Phe Leu Ser Ser Phe Ser Lys
1               5                   10

<210> SEQ ID NO 244
<211> LENGTH: 12
<212> TYPE: PRT
<213> ORGANISM: Zea mays

<400> SEQUENCE: 244

Val Phe Leu Ala Gly Ala Asp Asn Val Leu Gln Lys
1               5                   10

<210> SEQ ID NO 245
<211> LENGTH: 12
<212> TYPE: PRT
<213> ORGANISM: Zea mays

<400> SEQUENCE: 245

Asp Ile Gly Phe Asn Gly Leu Ala Asp Pro Asn Arg
1               5                   10

<210> SEQ ID NO 246
<211> LENGTH: 11
<212> TYPE: PRT
<213> ORGANISM: Zea mays

<400> SEQUENCE: 246

Asn Ala Leu Glu Asn Tyr Ala Tyr Asn Met Arg
1               5                   10

<210> SEQ ID NO 247
<211> LENGTH: 14
<212> TYPE: PRT
<213> ORGANISM: Zea mays

<400> SEQUENCE: 247

Val Pro Thr Val Asp Val Ser Val Val Asp Leu Thr Val Arg
1               5                   10

<210> SEQ ID NO 248
<211> LENGTH: 13
<212> TYPE: PRT
<213> ORGANISM: Zea mays

<400> SEQUENCE: 248

Gln Ile Ser Trp Asn Tyr Asn Tyr Gly Pro Ala Gly Arg
1               5                   10

<210> SEQ ID NO 249
<211> LENGTH: 12
<212> TYPE: PRT
<213> ORGANISM: Zea mays

<400> SEQUENCE: 249

Ala Arg Phe Glu Glu Leu Asn Met Asp Leu Phe Arg
1               5                   10

<210> SEQ ID NO 250
<211> LENGTH: 14
<212> TYPE: PRT
<213> ORGANISM: Zea mays

```
<400> SEQUENCE: 250

Arg Glu Gln Leu Gly Gln Gln Gly Tyr Ser Glu Met Gly Lys
1               5                   10

<210> SEQ ID NO 251
<211> LENGTH: 15
<212> TYPE: PRT
<213> ORGANISM: Zea mays

<400> SEQUENCE: 251

Thr Leu Leu Phe Gly Asp Lys Pro Val Thr Val Phe Gly Ile Arg
1               5                   10                  15

<210> SEQ ID NO 252
<211> LENGTH: 15
<212> TYPE: PRT
<213> ORGANISM: Zea mays

<400> SEQUENCE: 252

Arg Glu Gln Leu Gly Gln Gln Gly Tyr Ser Glu Met Gly Lys Lys
1               5                   10                  15

<210> SEQ ID NO 253
<211> LENGTH: 16
<212> TYPE: PRT
<213> ORGANISM: Zea mays

<400> SEQUENCE: 253

Gly Pro Leu Gln Ile Ser Trp Asn Tyr Asn Tyr Gly Pro Ala Gly Arg
1               5                   10                  15

<210> SEQ ID NO 254
<211> LENGTH: 18
<212> TYPE: PRT
<213> ORGANISM: Zea mays

<400> SEQUENCE: 254

Ala Leu Ser Phe Ala Ser Lys Ala Glu Glu Val Asp Glu Val Leu Gly
1               5                   10                  15

Ser Arg

<210> SEQ ID NO 255
<211> LENGTH: 19
<212> TYPE: PRT
<213> ORGANISM: Zea mays

<400> SEQUENCE: 255

Ala Val Gly Lys Val Leu Pro Asp Leu Asn Gly Lys Leu Thr Gly Met
1               5                   10                  15

Ser Phe Arg

<210> SEQ ID NO 256
<211> LENGTH: 19
<212> TYPE: PRT
<213> ORGANISM: Zea mays

<400> SEQUENCE: 256

Ala Leu Ser Phe Ala Ser Lys Ala Glu Glu Val Asp Glu Val Leu Gly
1               5                   10                  15

Ser Arg Arg

<210> SEQ ID NO 257
```

```
<211> LENGTH: 21
<212> TYPE: PRT
<213> ORGANISM: Zea mays

<400> SEQUENCE: 257

Leu Ser Pro Gly Thr Ala Phe Val Val Pro Ala Gly His Pro Phe Val
1               5                   10                  15

Ala Val Ala Ser Arg
            20

<210> SEQ ID NO 258
<211> LENGTH: 19
<212> TYPE: PRT
<213> ORGANISM: Zea mays

<400> SEQUENCE: 258

Asp Gln Arg Pro Ser Ile Ala Asn Gln His Gly Gln Leu Tyr Glu Ala
1               5                   10                  15

Asp Ala Arg

<210> SEQ ID NO 259
<211> LENGTH: 23
<212> TYPE: PRT
<213> ORGANISM: Zea mays

<400> SEQUENCE: 259

Ala Arg Leu Ser Pro Gly Thr Ala Phe Val Val Pro Ala Gly His Pro
1               5                   10                  15

Phe Val Ala Val Ala Ser Arg
            20

<210> SEQ ID NO 260
<211> LENGTH: 21
<212> TYPE: PRT
<213> ORGANISM: Zea mays

<400> SEQUENCE: 260

Arg His Ala Ser Glu Gly Gly His Gly Pro His Trp Pro Leu Pro Pro
1               5                   10                  15

Phe Gly Glu Ser Arg
            20

<210> SEQ ID NO 261
<211> LENGTH: 20
<212> TYPE: PRT
<213> ORGANISM: Zea mays

<400> SEQUENCE: 261

Tyr Tyr Gly Arg Gly Pro Leu Gln Ile Ser Trp Asn Tyr Asn Tyr Gly
1               5                   10                  15

Pro Ala Gly Arg
            20

<210> SEQ ID NO 262
<211> LENGTH: 8
<212> TYPE: PRT
<213> ORGANISM: Triticum Spp

<400> SEQUENCE: 262

Trp Ser Thr Gly Leu Gln Met Arg
1               5
```

```
<210> SEQ ID NO 263
<211> LENGTH: 10
<212> TYPE: PRT
<213> ORGANISM: Triticum Spp

<400> SEQUENCE: 263

Gln Val Val Asp Gln Gln Leu Ala Gly Arg
1               5                   10

<210> SEQ ID NO 264
<211> LENGTH: 10
<212> TYPE: PRT
<213> ORGANISM: Triticum Spp

<400> SEQUENCE: 264

Gln Tyr Glu Gln Thr Val Val Pro Pro Lys
1               5                   10

<210> SEQ ID NO 265
<211> LENGTH: 17
<212> TYPE: PRT
<213> ORGANISM: Triticum Spp

<400> SEQUENCE: 265

Gln Gly Gln Gln Gly Tyr Tyr Pro Thr Ser Pro Gln His Thr Gly Gln
1               5                   10                  15

Arg

<210> SEQ ID NO 266
<211> LENGTH: 20
<212> TYPE: PRT
<213> ORGANISM: Triticum Spp

<400> SEQUENCE: 266

Gln Val Val Asp Gln Gln Leu Ala Gly Arg Leu Pro Trp Ser Thr Gly
1               5                   10                  15

Leu Gln Met Arg
            20

<210> SEQ ID NO 267
<211> LENGTH: 22
<212> TYPE: PRT
<213> ORGANISM: Triticum Spp

<400> SEQUENCE: 267

Gln Gly Tyr Asp Ser Pro Tyr His Val Ser Ala Glu Gln Gln Ala Ala
1               5                   10                  15

Ser Pro Met Val Ala Lys
            20

<210> SEQ ID NO 268
<211> LENGTH: 29
<212> TYPE: PRT
<213> ORGANISM: Triticum Spp

<400> SEQUENCE: 268

Ser Leu Gln Gln Pro Gly Gln Gly Gln Gln Ile Gly Gln Gly Gln Gln
1               5                   10                  15

Gly Tyr Tyr Pro Thr Ser Pro Gln His Thr Gly Gln Arg
            20                  25

<210> SEQ ID NO 269
<211> LENGTH: 35
```

<212> TYPE: PRT
<213> ORGANISM: Triticum Spp

<400> SEQUENCE: 269

Gln Gly Tyr Tyr Pro Thr Ser Leu Gln Gln Pro Gly Gln Gly Gln Gln
1               5                   10                  15

Ile Gly Gln Gly Gln Gln Gly Tyr Tyr Pro Thr Ser Pro Gln His Thr
            20                  25                  30

Gly Gln Arg
        35

<210> SEQ ID NO 270
<211> LENGTH: 10
<212> TYPE: PRT
<213> ORGANISM: Glycine max

<400> SEQUENCE: 270

Leu Ser Ala Glu Phe Gly Ser Leu Arg Lys
1               5                   10

<210> SEQ ID NO 271
<211> LENGTH: 13
<212> TYPE: PRT
<213> ORGANISM: Glycine max

<400> SEQUENCE: 271

Ile Gly Glu Asn Lys Asp Ala Met Asp Gly Trp Phe Arg
1               5                   10

<210> SEQ ID NO 272
<211> LENGTH: 23
<212> TYPE: PRT
<213> ORGANISM: Glycine max

<400> SEQUENCE: 272

Lys Asn Ala Met Phe Val Pro His Tyr Asn Leu Asn Ala Asn Ser Ile
1               5                   10                  15

Ile Tyr Ala Leu Asn Gly Arg
            20

<210> SEQ ID NO 273
<211> LENGTH: 32
<212> TYPE: PRT
<213> ORGANISM: Glycine max

<400> SEQUENCE: 273

Thr Asn Asp Arg Pro Ser Ile Gly Asn Leu Ala Gly Ala Asn Ser Leu
1               5                   10                  15

Leu Asn Ala Leu Pro Glu Glu Val Ile Gln His Thr Phe Asn Leu Lys
            20                  25                  30

<210> SEQ ID NO 274
<211> LENGTH: 32
<212> TYPE: PRT
<213> ORGANISM: Glycine max

<400> SEQUENCE: 274

Thr Asn Asp Arg Pro Ser Ile Gly Asn Leu Ala Gly Ala Asn Ser Leu
1               5                   10                  15

Leu Asn Ala Leu Pro Glu Glu Val Ile Gln Gln Thr Phe Asn Leu Arg
            20                  25                  30

US 9,034,402 B2

PROTEIN HYDROLYSATE COMPOSITIONS HAVING IMPROVED SENSORY CHARACTERISTICS AND PHYSICAL PROPERTIES

CROSS REFERENCE TO RELATED APPLICATIONS

This application claims the priority of U.S. provisional application No. 60/911,935 filed Apr. 16, 2007, which is hereby incorporated by reference in its entirety.

FIELD OF THE INVENTION

The present invention relates to protein hydrolysate compositions having improved sensory characteristics and physical properties, processes for making protein hydrolysate compositions, and food products comprising protein hydrolysate compositions.

BACKGROUND OF THE INVENTION

The rates of obesity and the diseases associated with obesity are rising in the Unites States and throughout the world. While there is no single underlying cause, a contributing factor may be the fast-paced, harried life styles of many individuals and the concomitant consumption of fast food. Most fast food tends to be high in fat and/or sugar. There is a need, therefore, for a nutritious, readily accessible food product that can be eaten or drunk "on the go." This food product should not only taste good, but it should also be nutritionally sound; that is, the product should be low in fat, high in protein, and high in vitamins and antioxidants.

One type of food product that could be nutritionally sound and easily consumed is a liquid protein-containing beverage. The protein could be derived from soy or a variety of other protein sources. Although soy is an excellent source of protein, it tends to have "grassy" or "beany" flavors that some individuals find objectionable or unpalatable. What is needed, therefore, is an isolated soy protein product with reduced "soy" flavors. Furthermore, the isolated soy protein product to be added to the liquid beverage ideally should be substantially soluble and, at times, substantially translucent. Additionally, the isolated soy protein product should be stable at the pH of the desired liquid beverage.

SUMMARY OF THE INVENTION

Of the many aspects of the invention, therefore, is the provision of a protein hydrolysate composition. The protein hydrolysate composition comprises a mixture of polypeptide fragments having primarily either an arginine residue or a lysine residue at each carboxyl terminus. Additionally, the protein hydrolysate composition has a degree of hydrolysis of at least about 0.2% DH and a soluble solids index (SSI) of at least about 80% at a pH of greater than about 6.0.

Another aspect of the invention provides a process for preparing a protein hydrolysate composition. The process comprises contacting a protein material with an endopeptidase that specifically cleaves peptide bonds of the protein material on the carboxyl terminal side of an arginine residue or a lysine residue to produce a protein hydrolysate composition. The protein hydrolysate composition has a degree of hydrolysis of at least about 0.2% DH and a soluble solids index of at least about 80% at a pH of greater than about 6.0.

Yet another aspect of the invention encompasses a food product comprising an edible material and a protein hydrolysate composition. The protein hydrolysate composition comprises a mixture of polypeptide fragments having primarily either an arginine residue or a lysine residue at each carboxyl terminus. Furthermore, the composition has a degree of hydrolysis of at least about 0.2% DH and a soluble solids index of at least about 80% at a pH of greater than about 6.0.

Other aspects and features of the invention are described in more detail below.

REFERENCE TO COLOR FIGURES

The application contains at least one photograph executed in color. Copies of this patent application publication with color photographs will be provided by the Office upon request and payment of the necessary fee.

DETAILED DESCRIPTION OF THE INVENTION

Figure 1:
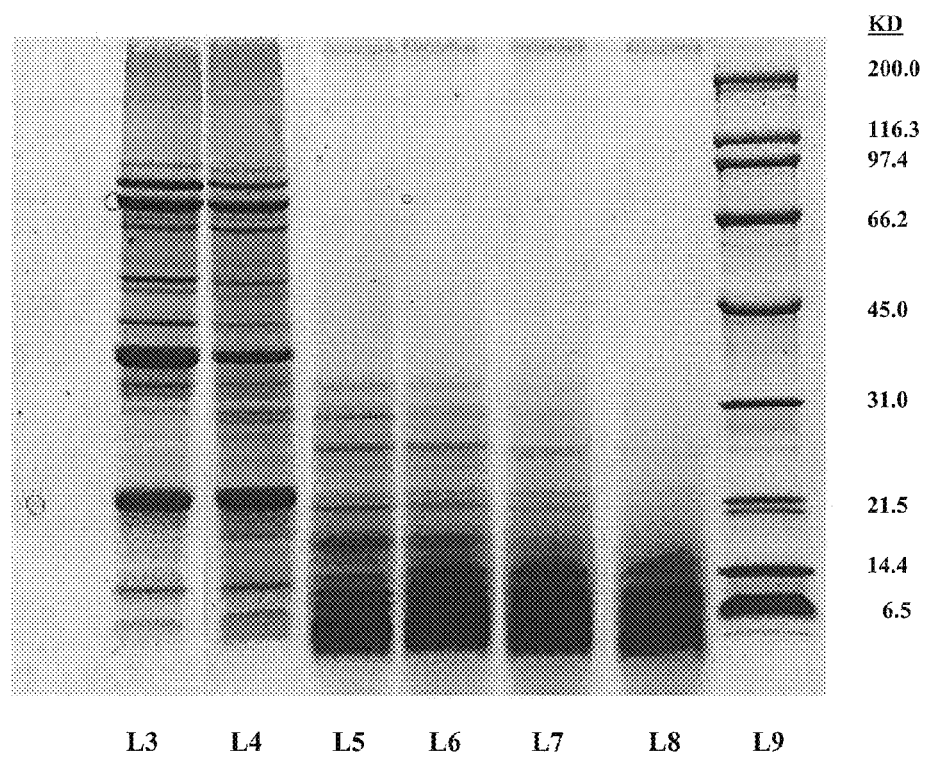
FIG. 1 illustrates hydrolysis of isolated soy protein by *Fusarium* trypsin-like endopeptidase (TL1). Shown is an image of a Coomassie-stained SDS-polyacrylamide gel. Lane 3 (L3) contains non-hydrolyzed isolated soy protein (SUPRO® 500E). Lane 4 (L4), lane 5 (L5), lane 6 (L6), lane 7 (L7), and lane 8 (L8) contain TL1 hydrolysates with 0.3% DH, 2.2% DH, 3.1% DH, 4.0% DH, and 5.0% DH degrees of hydrolysis (DH), respectively. Lane 9 (L9) contains a protein MW standard, with the sizes in kiloDaltons (kDa) indicated at the right of the gel.

The present invention provides protein hydrolysate compositions, processes for making protein hydrolysate compositions, and food products comprising protein hydrolysate compositions. It has been discovered, as illustrated in the examples, that digestion of a protein material with an endopeptidase that specifically cleaves the protein material on the carboxyl terminal side of an arginine residue or a lysine residue results in compositions comprising polypeptide fragments having improved physical properties, flavor, and sensory characteristics. Because of the improved physical properties, flavor, and sensory characteristics, the protein hydrolysate compositions of the invention may advantageously be utilized in a variety of food products.

(I) Process for Preparing a Protein Hydrolysate

One aspect of the present invention provides a process for preparing a protein hydrolysate comprising a mixture of polypeptide fragments that have primarily either an arginine residue or a lysine residue at each carboxyl terminus. The process comprises contacting a protein material with an endopeptidase that specifically cleaves the peptide bonds of the protein material on the carboxyl terminal side of an arginine residue or a lysine residue to produce a protein hydrolysate. The protein material or combination of protein materials used to prepare a protein hydrolysate can and will vary. Examples of suitable protein material are detailed below.

(a) Soy Protein Material

In some embodiments, the protein material may be a soy protein material. A variety of soy protein materials may be used in the process of the invention to generate a protein hydrolysate. In general, the soy protein material may be derived from whole soybeans in accordance with methods known in the art. The whole soybeans may be standard soybeans (i.e., non genetically modified soybeans), genetically modified soybeans (such as, e.g., soybeans with modified oils, soybeans with modified carbohydrates, soybeans with modified protein subunits, and so forth) or combinations thereof. Suitable examples of soy protein material include soy extract, soymilk, soymilk powder, soy curd, soy flour, isolated soy protein, soy protein concentrate, and mixtures thereof.

In one embodiment, the soy protein material used in the process may be a soy protein isolate (also called isolated soy protein, or ISP). In general, soy protein isolates have a protein content of at least about 90% soy protein on a moisture-free basis. The soy protein isolate may comprise intact soy proteins or it may comprise partially hydrolyzed soy proteins. The soy protein isolate may have a high content of storage protein subunits such as 7S, 11S, 2S, etc. Non-limiting examples of soy protein isolates that may be used as starting material in the present invention are commercially available, for example, from Solae, LLC (St. Louis, Mo.), and among them include SUPRO® 500E, SUPRO® EX 45, SUPRO® 620, SUPRO® 670, SUPRO® EX 33, SUPRO® PLUS 2600F, SUPRO® PLUS 2640 DS, SUPRO® PLUS 2800, SUPRO® PLUS 3000, and combinations thereof.

In another embodiment, the soy protein material may be a soy protein concentrate, which has a protein content of about 65% to less than about 90% on a moisture-free basis. Examples of suitable soy protein concentrates useful in the invention include the PROCON™ product line, ALPHA™ 12 and ALPHA™ 5800, all of which are commercially available from Solae, LLC. Alternatively, soy protein concentrate may be blended with the soy protein isolate to substitute for a portion of the soy protein isolate as a source of soy protein material. Typically, if a soy protein concentrate is substituted for a portion of the soy protein isolate, the soy protein concentrate is substituted for up to about 40% of the soy protein isolate by weight, at most, and more preferably is substituted for up to about 30% of the soy protein isolate by weight.

In yet another embodiment, the soy protein material may be soy flour, which has a protein content of about 49% to about 65% on a moisture-free basis. The soy flour may be defatted soy flour, partially defatted soy flour, or full fat soy flour. The soy flour may be blended with soy protein isolate or soy protein concentrate.

In an alternate embodiment, the soy protein material may be material that has been separated into four major storage protein fractions or subunits (15S, 11S, 7S, and 2S) on the basis of sedimentation in a centrifuge. In general, the 11S fraction is highly enriched in glycinins, and the 7S fraction is highly enriched in beta-conglycinins. In yet another embodiment, the soy protein material may be protein from high oleic soybeans.

(b) Other Protein Materials

In another embodiment, the protein material may be derived from a plant other than soy. By way of non-limiting example, suitable plants include amaranth, arrowroot, barley, buckwheat, canola, cassava, channa (garbanzo), legumes, lentils, lupin, maize, millet, oat, pea, potato, rice, rye, sorghum, sunflower, tapioca, triticale, wheat, and mixtures thereof. Especially preferred plant proteins include barley, canola, lupin, maize, oat, pea, potato, rice, wheat, and combinations thereof. In one embodiment, the plant protein material may be canola meal, canola protein isolate, canola protein concentrate, and combinations thereof. In another embodiment, the plant protein material may be maize or corn protein powder, maize or corn protein concentrate, maize or corn protein isolate, maize or corn germ, maize or corn gluten, maize or corn gluten meal, maize or corn flour, zein protein, and combinations thereof. In still another embodiment, the plant protein material may be barley powder, barley protein concentrate, barley protein isolate, barley meal, barley flour, and combinations thereof. In an alternate embodiment, the plant protein material may be lupin flour, lupin protein isolate, lupin protein concentrate, and combinations thereof. In another alternate embodiment, the plant protein material may be oatmeal, oat flour, oat protein flour, oat protein isolate, oat protein concentrate, and combinations thereof. In yet another embodiment, the plant protein material may be pea flour, pea protein isolate, pea protein concentrate, and combinations thereof. In still another embodiment, the plant protein material may be potato protein powder, potato protein isolate, potato protein concentrate, potato flour, and combinations thereof. In a further embodiment, the plant protein material may be rice flour, rice meal, rice protein powder, rice protein isolate, rice protein concentrate, and combinations thereof. In another alternate embodiment, the plant protein material may be wheat protein powder, wheat gluten, wheat germ, wheat flour, wheat protein isolate, wheat protein concentrate, solubilized wheat proteins, and combinations thereof.

In other embodiments, the protein material may be derived from an animal source. In one embodiment, the animal protein material may be derived from eggs. Non-limiting examples of suitable egg proteins include powdered egg, dried egg solids, dried egg white protein, liquid egg white protein, egg white protein powder, isolated ovalbumin protein, and combinations thereof. Egg proteins may be derived from the eggs of chicken, duck, goose, quail, or other birds. In an alternate embodiment, the protein material may be derived from a dairy source. Suitable dairy proteins include non-fat dry milk powder, milk protein isolate, milk protein concentrate, acid casein, caseinate (e.g., sodium caseinate, calcium caseinate, and the like), whey protein isolate, whey protein concentrate, and combinations thereof. The milk protein material may be derived from cows, goats, sheep, donkeys, camels, camelids, yaks, water buffalos, etc. In a further embodiment, the protein may be derived from the muscles, organs, connective tissues, or skeletons of land-based or aquatic animals. As an example, the animal protein may be gelatin, which is produced by partial hydrolysis of collagen extracted from the bones, connective tissues, organs, etc, from cattle or other animals.

It is also envisioned that combinations of a soy protein material and at least one other protein material also may be used in the process of the invention. That is, a protein hydrolysate composition may be prepared from a combination of a soy protein material and at least one other protein material. In one embodiment, a protein hydrolysate composition may be prepared from a combination of a soy protein material and one other protein material selected from the group consisting of barley, canola, lupin, maize, oat, pea, potato, rice, wheat, animal material, dairy, and egg. In another embodiment, a protein hydrolysate composition may be prepared from a combination of a soy protein material and two other protein materials selected from the group consisting of barley, canola, lupin, maize, oat, pea, potato, rice, wheat, animal material, dairy, and egg. In further embodiments, a protein hydrolysate composition may be prepared from a combination of a soy protein material and three or more other protein materials selected from the group consisting of barley, canola, lupin, maize, oat, pea, potato, rice, wheat, animal material, dairy, and egg.

The concentrations of the soy protein material and the other protein material used in combination can and will vary. The amount of soy protein material may range from about 1% to about 99% of the total protein used in the combination. In one embodiment, the amount of soy protein material may range from about 1% to about 20% of the total protein used in combination. In another embodiment, the amount of soy protein material may range from about 20% to about 40% of the total protein used in combination. In still another embodiment, the amount of soy protein material may range from about 40% to about 80% of the total protein used in combination. In a further embodiment, the amount of soy protein material may range from about 80% to about 99% of the total protein used in combination. Likewise, the amount of the (at least one) other protein material may range from about 1% to about 99% of the total protein used in combination. In one embodiment, the amount of other protein material may range from about 1% to about 20% of the total protein used in combination. In another embodiment, the amount of other protein material may range from about 20% to about 40% of the total protein used in combination. In still another embodiment, the amount of other protein material may range from about 40% to about 80% of the total protein used in combination. In a further embodiment, the amount of other protein material may range from about 80% to about 99% of the total protein used in combination.

(c) Protein Slurry

In the process of the invention, the protein material is typically mixed or dispersed in water to form a slurry comprising about 1% to about 20% protein by weight (on an "as is" basis). In one embodiment, the slurry may comprise about 1% to about 5% protein (as is) by weight. In another embodiment, the slurry may comprise about 6% to about 10% protein (as is) by weight. In a further embodiment, the slurry may comprise about 11% to about 15% protein (as is) by weight. In still another embodiment, the slurry may comprise about 16% to about 20% protein (as is) by weight.

After the protein material is dispersed in water, the slurry of protein material may be heated from about 70° C. to about 90° C. for about 2 minutes to about 20 minutes to inactivate putative endogenous protease inhibitors. Typically, the pH and the temperature of the protein slurry are adjusted so as to optimize the hydrolysis reaction, and in particular, to ensure that the endopeptidase used in the hydrolysis reaction functions near its optimal activity level. The pH of the protein slurry may be adjusted and monitored according to methods generally known in the art. The pH of the protein slurry may be adjusted and maintained at from about pH 5.0 to about pH 10.0. In one embodiment, the pH of the protein slurry may be adjusted and maintained at from about pH 7.0 to about pH 8.0. In another embodiment, the pH of the protein slurry may be adjusted and maintained at from about pH 8.0 to about pH 9.0. In a preferred embodiment, the pH of the protein slurry may be adjusted and maintained at about pH 8.0. The temperature of the protein slurry is preferably adjusted and maintained at from about 40° C. to about 70° C. during the hydrolysis reaction in accordance with methods known in the art. In a preferred embodiment, the temperature of the protein slurry may be adjusted and maintained at from about 50° C. to about 60° C. during the hydrolysis reaction. In general, temperatures above this range may eventually inactivate the endopeptidase, while temperatures below or above this range tend to slow the activity of the endopeptidase.

(d) endopeptidase

The hydrolysis reaction is generally initiated by adding an endopeptidase to the slurry of protein material. Several endopeptidases are suitable for use in the process of the invention. Preferably, the endopeptidase will be a food-grade enzyme. The endopeptidase may have optimal activity under the conditions of hydrolysis from about pH 6.0 to about pH 11.0, and more preferably, from about pH 7.0 to about pH 9.0, and at a temperature from about 40° C. to about 70° C., and more preferably from about 45° C. to about 60° C.

In general, the endopeptidase will be a member of the S1 serine protease family (MEROPS Peptidase Database, release 8.00A; //merops.sanger.ac.uk). Preferably, the endopeptidase will cleave peptide bonds on the carboxyl terminal side of arginine, lysine, or both residues. Thus, endopeptidase may be a trypsin-like endopeptidase, which cleaves peptide bonds on the carboxyl terminal side of arginine, lysine, or both. A trypsin-like endopeptidase in the context of the present invention may be defined as an endopeptidase having a Trypsin ratio of more than 100 (see Example 16). The trypsin-like endopeptidase may be a lysyl endopeptidase, which cleaves peptide bonds on the carboxyl terminal side of lysine residues. In preferred embodiments, the endopeptidase may be of microbial origin, and more preferably of fungal origin. Although trypsin and trypsin-like endopeptidases are available from other sources (e.g., animal sources), trypsins from animal sources may not be able to cleave the starting protein material, as shown in Example 14.

In one embodiment, the endopeptidase may be trypsin-like protease from *Fusarium oxysporum* (U.S. Pat. No. 5,288,627; U.S. Pat. No. 5,693,520, each of which is hereby incorporated by reference in its entirety). This endopeptidase is termed "TL1" and its protein sequence (SEQ ID NO:1) is presented in Table A. The accession number for TL1 is SWISSPROT No. P35049 and its MEROPS ID is S01.103. In another embodiment, the endopeptidase may be trypsin-like protease from *Fusarium solani* (International Patent Application WO2005/040372-A1, which is incorporated herein in its entirety). This endopeptidase is termed "TL5," and its protein sequence (SEQ ID NO:2) is presented in Table A. The accession number for TL5 is GENESEQP: ADZ80577. In still another embodiment, the endopeptidase may be trypsin-like protease from *Fusarium* cf. *solani*. This endopeptidase is termed "TL6," and its protein sequence (SEQ ID NO:3) is presented in Table A. In a further embodiment, the endopeptidase may be lysyl endopeptidase from *Achromobacter lyticus*. This endopeptidase is termed "SP3," and its protein sequence (SEQ ID NO:4) is presented in Table A. The accession number for SP3 is SWISSPROT No. 15636 and the MEROPS ID of SP3 is S01.280. In an exemplary embodiment, the endopeptidase may be TL1.

TABLE A

Exemplary Trypsin-like Proteases.

| SEQ ID NO: | Identity | Sequence |
|---|---|---|
| 1 | Trypsin-like protease (TL1) from *Fusarium oxysporum* | MVKFASVVALVAPLAAAAPQEIPNIVGGTS ASAGDFPFIVSISRNGGPWCGGSLLNANTV LTAAHCVSGYAQSGFQIRAGSLSRTSGGIT SSLSSVRVHPSYSGNNNDLAILKLSTSIPS GGNIGYARLAASGSDPVAGSSATVAGWGAT SEGGSSTPVNLLKVTVPIVSRATCRAQYGT SAITNQMFCAGVSSGGKDSCQGDSGGPIVD SSNTLIGAVSWGNGCARPNYSGVYASVGAL RSFIDTYA |
| 2 | Trypsin-like protease (TL5) from *Fusarium solani* | MVKFAAILALVAPLVAARPQDSSPMIVGGT AASAGDFPFIVSIAYNGGPWCGGTLLNANT VMTAAHCTQGRSASAFQVRAGSLNRNSGGV TSSVSSIRIHPSFSSSTLNNDVSILKLSTP ISTSSTISYGRLAASGSDPVAGSDATVAGW GVTSQGSSSSPVALRKVTIPIVSRTTCRSQ YGTSAITTNMFCAGLAEGGKDSCQGDSGGP IVDTSNTVIGIVSWGEGCAQPNLSGVYARV GSLRTYIDGQL |
| 3 | Trypsin-like protease (TL6) from *Fusarium* cf. *solani* | MVKFAAILALVAPLVAARPQDRPMIVGGTA ASAGDFPFIVSIAYNGGPWCGGTLLNASTV LTAAHCTQGRSASAFQVRAGSLNRNSGGVT SAVSSIRIHPSFSGSTLNNDVSILKLSTPI STSSTISYGRLAASGSDPAAGSDATVAGWG VTSQGSSSSPVALRKVTIPIVSRTTCRSQY GTSAITTNMFCAGLAEGGKDSCQGDSGGPI VDTSNTVIGIVSWGEGCAQPNFSGVYARVG SLRSYIDGQL |
| 4 | Lysyl endopeptidase (SP3) from *Achromobacter lyticus* | MKRICGSLLLLGLSISAALAAPASRPAAFD YANLSSVDKVALRTMPAVDVAKAKAEDLQR DKRGDIPRFALAIDVDMTPQNSGAWEYTAD GQFAVWRQRVRSEKALSLNFGFTDYYMPAG GRLLVYPATQAPAGDRGLISQYDASNNNSA RQLWTAVVPGAEAVIEAVIPRDKVGEFKLR LTKVNHDYVGFGPLARRLAAASGEKGVSGS CNIDVVCPEGDGRRDIIRAVGAYSKSGTLA CTGSLVNNTANDRKMYFLTAHHCGMGTAST AASIVVYWNYQNSTCRAPNTPASGANGDGS MSQTQSGSTVKATYATSDFTLLELNNAANP AFNLFWAGWDRRDQNYPGAIAIHHPNVAEK RISNSTSPTSFVAWGGGAGTTHLNVQWQPS GGVTEPGSSGSPIYSPEKRVLGQLHGGPSS CSATGTNRSDQYGRVFTSWTGGGAAASRLS DWLDPASTGAQFIDGLDSGGGTPNTPPVAN FTSTTSGLTATFTDSSTDSDGSIASRSWNF GDGSTSTATNPSKTYAAAGTYTVTLTVTDN GGATNTKTGSVTVSGGPGAQTYTNDTDVAI PDNATVESPITVSGRTGNGSATTPIQVTIY HTYKSDLKVDLVAPDGTVYNLHNRTGGSAH NIIQTFTKDLSSEAAQRAPGSCG |

In another embodiment, the endopeptidase may comprise an amino acid sequence that is at least 80%, 81%, 82%, 83%, 84%, or 85% identical to SEQ ID NOs: 1, 2, 3, 4, or a fragment thereof. In a further embodiment, the endopeptidase may comprise an amino acid sequence that is at least 86%, 87%, 88%, 89%, 90%, 91%, or 92% identical to SEQ ID NOs: 1, 2, 3, 4, or a fragment thereof. In yet another embodiment, the endopeptidase may comprise an amino acid sequence that is at least 93%, 94%, 95%, 96%, 97%, 98% or 99% identical to SEQ ID NOs: 1, 2, 3, 4, or a fragment thereof. The fragment of any of these sequences having protease activity may be the amino acid sequence of the active enzyme, e.g. after processing, such as after any signal peptide and/or propeptide has been cleaved off. Preferred fragments include amino acids 25-248 of SEQ ID NO:1, amino acids 26-251 of SEQ ID NO:2, amino acids 18-250 of SEQ ID NO:3, or amino acids 21-653 of SEQ ID NO:4.

For purposes of the present invention, the alignment of two amino acid sequences may be determined by using the Needle program from the EMBOSS package (Rice, P., Longden, I. and Bleasby, A. (2000) EMBOSS: The European Molecular Biology Open Software Suite. *Trends in Genetics* 16, (6) pp 276-277; http://emboss.org) version 2.8.0. The Needle program implements the global alignment algorithm described in Needleman, S. B. and Wunsch, C. D. (1970) J. Mol. Biol. 48, 443-453. The substitution matrix used is BLOSUM62, gap opening penalty is 10, and gap extension penalty is 0.5. In general, the percentage of sequence identity is determined by comparing two optimally aligned sequences over a comparison window, wherein the portion of the amino acid sequence in the comparison window may comprise additions or deletions (i.e., gaps) as compared to the reference sequence (which does not comprise additions or deletions) for optimal alignment of the two sequences. The percentage is calculated by determining the number of positions at which an identical amino acid occurs in both sequences to yield the number of matched positions, dividing the number of matched positions by the total number of positions in the shortest of the two sequences in the window of comparison, and multiplying the result by 100 to yield the percentage of sequence identity.

A skilled practitioner will understand that an amino acid residue may be substituted with another amino acid residue having a similar side chain without affecting the function of the polypeptide. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acid substitution groups include: valine-leucine-isoleucine, phenylalanine-tyrosine, lysine-arginine, alanine-valine, and asparagine-glutamine. Thus, the endopeptidase may have at least one conservative amino acid substitution with respect to SEQ ID NOs:1, 2, 3, or 4. In one embodiment, the endopeptidase may have about 50 conservative amino acid substitutions with respect to SEQ ID NOs: 1, 2, 3, or 4. In another embodiment, the endopeptidase may have about 40 conservative amino acid substitutions with respect to SEQ ID NOs:1, 2, 3, or 4. In yet another embodiment, the endopeptidase may have about 30 conservative amino acid substitutions with respect to SEQ ID NOs:1, 2, 3, or 4. In another alternate embodiment, the endopeptidase may have about 20 conservative amino acid substitutions with respect to SEQ ID NOs:1, 2, 3, or 4. In still another embodiment, the endopeptidase may have about 10 conservative amino acid substitutions with respect to SEQ ID NOs:1, 2, 3, or 4. In yet another embodiment, the endopeptidase may have about 5 conservative amino acid substitutions with respect to SEQ ID NOs:1, 2, 3, or 4. In a further embodiment, the endopeptidase may have about one conservative amino acid substitution with respect to SEQ ID NOs:1, 2, 3, or 4.

Various combinations of protein material and endopeptidase are presented in Table B.

TABLE B

Preferred Combinations.

| Protein Material | Endopeptidase |
| --- | --- |
| Soy | Trypsin-like protease |
| Soy | TL1 |
| Soy | TL5 |
| Soy | TL6 |
| Soy | SP3 |
| Barley | Trypsin-like protease |
| Barley | TL1 |
| Barley | TL5 |
| Barley | TL6 |
| Barley | SP3 |
| Canola | Trypsin-like protease |
| Canola | TL1 |
| Canola | TL5 |
| Canola | TL6 |
| Canola | SP3 |
| Lupin | Trypsin-like protease |
| Lupin | TL1 |
| Lupin | TL5 |
| Lupin | TL6 |
| Lupin | SP3 |
| Maize | Trypsin-like protease |
| Maize | TL1 |
| Maize | TL5 |
| Maize | TL6 |
| Maize | SP3 |
| Oat | Trypsin-like protease |
| Oat | TL1 |
| Oat | TL5 |
| Oat | TL6 |
| Oat | SP3 |
| Pea | Trypsin-like protease |
| Pea | TL1 |
| Pea | TL5 |
| Pea | TL6 |
| Pea | SP3 |
| Potato | Trypsin-like protease |
| Potato | TL1 |
| Potato | TL5 |
| Potato | TL6 |
| Potato | SP3 |
| Rice | Trypsin-like protease |
| Rice | TL1 |
| Rice | TL5 |
| Rice | TL6 |
| Rice | SP3 |
| Wheat | Trypsin-like protease |
| Wheat | TL1 |
| Wheat | TL5 |
| Wheat | TL6 |
| Wheat | SP3 |
| Egg | Trypsin-like protease |
| Egg | TL1 |
| Egg | TL5 |
| Egg | TL6 |
| Egg | SP3 |
| Dairy | Trypsin-like protease |
| Dairy | TL1 |
| Dairy | TL5 |
| Dairy | TL6 |
| Dairy | SP3 |
| Animal (e.g., gelatin) | Trypsin-like protease |
| Animal (e.g., gelatin) | TL1 |
| Animal (e.g., gelatin) | TL5 |
| Animal (e.g., gelatin) | TL6 |
| Animal (e.g., gelatin) | SP3 |

TABLE B-continued

Preferred Combinations.

| Protein Material | Endopeptidase |
| --- | --- |
| Soy and Barley | Trypsin-like protease |
| Soy and Barley | TL1 |
| Soy and Barley | TL5 |
| Soy and Barley | TL6 |
| Soy and Barley | SP3 |
| Soy and Canola | Trypsin-like protease |
| Soy and Canola | TL1 |
| Soy and Canola | TL5 |
| Soy and Canola | TL6 |
| Soy and Canola | SP3 |
| Soy and Lupin | Trypsin-like protease |
| Soy and Lupin | TL1 |
| Soy and Lupin | TL5 |
| Soy and Lupin | TL6 |
| Soy and Lupin | SP3 |
| Soy and Maize | Trypsin-like protease |
| Soy and Maize | TL1 |
| Soy and Maize | TL5 |
| Soy and Maize | TL6 |
| Soy and Maize | SP3 |
| Soy and Oat | Trypsin-like protease |
| Soy and Oat | TL1 |
| Soy and Oat | TL5 |
| Soy and Oat | TL6 |
| Soy and Oat | SP3 |
| Soy and Pea | Trypsin-like protease |
| Soy and Pea | TL1 |
| Soy and Pea | TL5 |
| Soy and Pea | TL6 |
| Soy and Pea | SP3 |
| Soy and Potato | Trypsin-like protease |
| Soy and Potato | TL1 |
| Soy and Potato | TL5 |
| Soy and Potato | TL6 |
| Soy and Potato | SP3 |
| Soy and Rice | Trypsin-like protease |
| Soy and Rice | TL1 |
| Soy and Rice | TL5 |
| Soy and Rice | TL6 |
| Soy and Rice | SP3 |
| Soy and Wheat | Trypsin-like protease |
| Soy and Wheat | TL1 |
| Soy and Wheat | TL5 |
| Soy and Wheat | TL6 |
| Soy and Wheat | SP3 |
| Soy and Egg | Trypsin-like protease |
| Soy and Egg | TL1 |
| Soy and Egg | TL5 |
| Soy and Egg | TL6 |
| Soy and Egg | SP3 |
| Soy and Dairy | Trypsin-like protease |
| Soy and Dairy | TL1 |
| Soy and Dairy | TL5 |
| Soy and Dairy | TL6 |
| Soy and Dairy | SP3 |
| Soy and Animal (e.g., gelatin) | Trypsin-like protease |
| Soy and Animal (e.g., gelatin) | TL1 |
| Soy and Animal (e.g., gelatin) | TL5 |
| Soy and Animal (e.g., gelatin) | TL6 |
| Soy and Animal (e.g., gelatin) | SP3 |

The amount of endopeptidase added to the protein material can and will vary depending upon the source of the protein material, the desired degree of hydrolysis, and the duration of the hydrolysis reaction. The amount of endopeptidase may range from about 1 mg of enzyme protein to about 5000 mg of enzyme protein per kilogram of protein material. In another embodiment, the amount may range from 10 mg of enzyme protein to about 2000 mg of enzyme protein per kilogram of protein material. In yet another embodiment, the amount may range from about 50 mg of enzyme protein to about 1000 mg of enzyme protein per kilogram of protein material. As will be appreciated by a skilled artisan, the duration of the hydrolysis reaction can and will vary. Generally speaking, the duration of the hydrolysis reaction may range from a few minutes to many hours, such as, from about 30 minutes to about 48 hours. To end the hydrolysis reaction, the composition may be heated to a temperature that is high enough to inactivate the endopeptidase. For example, heating the composition to a temperature of approximately 90° C. will substantially heat-inactivate the endopeptidase.

(II) Protein Hydrolysate Compositions

The protein hydrolysate compositions, compared with the protein starting material will, comprise a mixture of polypeptide fragments of varying length and molecular weights. Each of the peptide fragments typically will have either an arginine or lysine residue at its carboxyl terminus (as demonstrated in Examples 3, 4, 13, and 18). The polypeptide fragments may range in size from about 75 Daltons (Da) to about 50,000 Da, or more preferably from about 150 Da to about 20,000 Da. In some embodiments, the average molecular size of the polypeptide fragments may be less than about 20,000 Da. In other embodiments, the average molecular size of the polypeptide fragments may be less than about 15,000 Da. In still other embodiment, the average molecular size of the polypeptide fragments may be less than about 10,000 Da. In additional embodiments, the average molecular size of the polypeptide fragments may be less than about 5000 Da.

The degree of hydrolysis of the protein hydrolysate compositions of the invention can and will vary depending upon the source of the protein material, the endopeptidase used, and the degree of completion of the hydrolysis reaction. The degree of hydrolysis (DH) refers to the percentage of peptide bonds cleaved versus the starting number of peptide bonds. For example, if a starting protein containing five hundred peptide bonds is hydrolyzed until fifty of the peptide bonds are cleaved, then the DH of the resulting hydrolysate is 10% DH. The degree of hydrolysis may be determined using the trinitrobenzene sulfonic (TNBS) calorimetric method or the ortho-phthaldialdehye (OPA) method, as detailed in the examples. The higher the degree of hydrolysis the greater the extent of protein hydrolysis. Typically, as the protein is further hydrolyzed (i.e., the higher the DH), the molecular weight of the peptide fragments decreases, the peptide profile changes accordingly, and the viscosity of the mixture decreases. The DH may be measured in the entire hydrolysate (i.e., whole fraction) or the DH may be measured in the soluble fraction of the hydrolysate (i.e., the supernatant fraction after centrifugation of the hydrolysate at about 500-1000×g for about 5-10 min).

In general, the degree of hydrolysis of the protein hydrolysate will be at least about 0.2% DH. In one embodiment, the degree of hydrolysis of the protein hydrolysate may range from about 0.2% DH to about 2% DH. In another embodiment, the degree of hydrolysis of the protein hydrolysate may range from about 2% DH to about 8% DH. In yet another embodiment, the degree of hydrolysis of the protein hydrolysate may range from about 8% DH to about 14% DH. In an alternate embodiment, the degree of hydrolysis of the protein hydrolysate may range from about 14% DH to about 20% DH. In additional embodiments, the degree of hydrolysis of the protein hydrolysate may be greater than about 20% DH.

The solubility of the protein hydrolysate compositions can and will vary depending upon the source of the starting protein material, the endopeptidase used, and the pH of the composition. The soluble solids index (SSI) is a measure of the solubility of the solids (i.e., polypeptide fragments) comprising a protein hydrolysate composition. The amount of soluble solids may be estimated by measuring the amount of solids in solution before and after centrifugation (e.g., about 500-1000×g for about 5-10 min). Alternatively, the amount of soluble solids may be determined by estimating the amount of protein in the composition before and after centrifugation using a technique well known in the art (such as, e.g., a bicinchoninic acid (BCA) protein determination colorimetric assay).

In general, the protein hydrolysate composition of the invention, regardless of its degree of hydrolysis, has a soluble solids index of at least about 80% at a pH greater than about pH 6.0. In one embodiment, the protein hydrolysate composition may have a soluble solids index ranging from about 80% to about 85% at a pH greater than about pH 6.0. In another embodiment, the protein hydrolysate composition may have a soluble solids index ranging from about 85% to about 90% at a pH greater than about pH 6.0. In a further embodiment, the protein hydrolysate composition may have a soluble solids index ranging from about 90% to about 95% at a pH greater than about 6.0. In another alternate embodiment, the protein hydrolysate composition may have a soluble solids index ranging from about 95% to about 99% at a pH greater than about 6.0.

Furthermore, the solubility of the protein hydrolysate compositions of the invention may vary at about pH 4.0 to about pH 5.0 as a function of the degree of hydrolysis. For example, soy protein hydrolysate compositions having degrees of hydrolysis greater than about 3% DH tend to be more soluble at about pH 4.0 to about pH 5.0 than those having degrees of hydrolysis less than about 3% DH.

Generally speaking, soy protein hydrolysate compositions having degrees of hydrolysis of about 1% DH to about 6% DH are stable at a pH from about pH 7.0 to about pH 8.0. Stability refers to the lack of sediment formation over time. The protein hydrolysate compositions may be stored at room temperature (i.e., ~23° C.) or a refrigerated temperature (i.e., ~4° C.). In one embodiment, the protein hydrolysate composition may be stable for about one week to about four weeks. In another embodiment, the protein hydrolysate composition may be stable for about one month to about six months. In a further embodiment, the protein hydrolysate composition may be stable for more than about six months.

The protein hydrolysate composition may be dried. For example the protein hydrolysate composition may be spray dried. The temperature of the spray dryer inlet may range from about 260° C. (500° F.) to about 315° C. (600° F.) and the exhaust temperature may range from about 82° C. (180° F.) to about 38° C. (100° F.). Alternatively, the protein hydrolysate composition may be vacuum dried, freeze dried, or dried using other procedures known in the art.

In embodiments in which the protein hydrolysate is derived from soy protein, the degree of hydrolysis may range from about 0.2% DH to about 14% DH, and more preferably from about 1% DH to about 6% DH. In addition to the number of polypeptide fragments formed, as illustrated in the examples, the degree of hydrolysis typically impacts other physical properties and sensory properties of the resulting soy protein hydrolysate composition. Typically, as the degree of hydrolysis increases from about 1% DH to about 6% DH, the soy protein hydrolysate composition has increased transparency or translucency and decreased grain and soy/legume sensory attributes. Furthermore, the soy protein hydrolysate composition has substantially less bitter sensory attributes when the degree of hydrolysis is less than about 2% DH compared to when the degree of hydrolysis is greater than about 2% DH. Stated another way, higher degrees of hydrolysis reduce grain and soy/legume sensory attributes, whereas lower degrees of hydrolysis reduce bitter sensory attributes. The sensory attributes and methods for determining them are detailed in the Examples.

Furthermore, in embodiments in which the protein hydrolysate is derived from soy, the soy protein hydrolysate composition may comprise polypeptides selected from the group consisting of SEQ ID NOs:5-177 and 270-274. In one embodiment, the soy protein hydrolysate may comprise at least one polypeptide having an amino acid sequence that corresponds to or is derived from the group consisting of SEQ ID NOs:5-177 and 270-274. In an alternate embodiment, the soy protein hydrolysate may comprise at least about ten polypeptides or fragments thereof selected from the group consisting of SEQ ID NOs:5-177 and 270-274. In another embodiment, the soy protein hydrolysate may comprise at least about 20 polypeptides or fragments thereof selected from the group consisting of SEQ ID NOs:5-177 and 270-274. In a further embodiment, the soy protein hydrolysate may comprise at least about 40 polypeptides or fragments thereof selected from the group consisting of SEQ ID NOs: 5-177 and 270-274. In yet another embodiment, the soy protein hydrolysate may comprise at least about 80 polypeptides or fragments thereof selected from the group consisting of SEQ ID NOs:5-177 and 270-274. In yet another embodiment, the soy protein hydrolysate may comprise at least about 120 polypeptides or fragments thereof selected from the group consisting of SEQ ID NOs:5-177 and 270-274. In a further embodiment, the soy protein hydrolysate may comprise at least about 178 polypeptides or fragments thereof selected from the group consisting of SEQ ID NOs:5-177 and 270-274.

In other embodiments in which the protein hydrolysate is derived from a combination of soy protein and dairy, the combined soy/dairy protein hydrolysate composition may comprise polypeptides selected from the group consisting of SEQ ID NOs:5-197 and 270-274. In one embodiment, the combined soy/dairy hydrolysate may comprise at least one polypeptide having an amino acid sequence that corresponds to or is derived from the group consisting of SEQ ID NOs:5-197 and 270-274. In an alternate embodiment, the combined soy/dairy hydrolysate may comprise at least about ten polypeptides or fragments thereof selected from the group consisting of SEQ ID NOs:5-197 and 270-274. In another embodiment, the combined soy/dairy hydrolysate may comprise at least about 50 polypeptides or fragments thereof selected from the group consisting of SEQ ID NOs:5-197 and 270-274. In another alternate embodiment, the combined soy/dairy hydrolysate may comprise at least about 100 polypeptides or fragments thereof selected from the group consisting of SEQ ID NOs:5-197 and 270-274. In another embodiment, the soy/dairy hydrolysate may comprise at least about 150 polypeptides or fragments thereof selected from the group consisting of SEQ ID NOs:5-197 and 270-274. In still another alternate embodiment, the combined soy/dairy hydrolysate may comprise at least about 198 polypeptides or fragments thereof selected from the group consisting of SEQ ID NOs: 5-197 and 270-274.

In additional embodiments in which the protein hydrolysate is derived from canola, the protein hydrolysate composition may comprise polypeptides selected from the group consisting of SEQ ID NOs:198-237. In one embodiment, the canola hydrolysate may comprise at least one polypeptide having an amino acid sequence that corresponds to or is derived from the group consisting of SEQ ID NOs:198-237. In an alternate embodiment, the canola hydrolysate may comprise at least about ten polypeptides or fragments thereof selected from the group consisting of SEQ ID NOs:198-237.

In another embodiment, the canola hydrolysate may comprise at least about 20 polypeptides or fragments thereof selected from the group consisting of SEQ ID NOs:198-237. In yet another alternate embodiment, the canola hydrolysate may comprise at least thirty-nine polypeptides having an amino acid sequence that corresponds to or is derived from the group consisting of SEQ ID NOs:198-237.

In other additional embodiments in which the protein hydrolysate is derived from maize, the protein hydrolysate composition may comprise polypeptides selected from the group consisting of SEQ ID NOs:238-261. In one embodiment, the maize hydrolysate may comprise at least one polypeptide having an amino acid sequence that corresponds to or is derived from the group consisting of SEQ ID NOs: 238-261. In another embodiment, the maize hydrolysate may comprise at least ten polypeptides having an amino acid sequence that corresponds to or is derived from the group consisting of SEQ ID NOs:238-261. In a further embodiment, the maize hydrolysate may comprise at least 24 polypeptides having an amino acid sequence that corresponds to or is derived from the group consisting of SEQ ID NOs:238-261.

Furthermore, in embodiments in which the protein hydrolysate is derived from wheat, the protein hydrolysate composition may comprise polypeptides selected from the group consisting of SEQ ID NOs:262-269. In one embodiment, the wheat hydrolysate may comprise at least one polypeptide having an amino acid sequence that corresponds to or is derived from the group consisting of SEQ ID NOs: 262-269. In a further embodiment, the wheat hydrolysate may comprise at least eight polypeptides having an amino acid sequence that corresponds to or is derived from the group consisting of SEQ ID NOs: 262-269.

The invention may also encompass any of the polypeptides or fragments thereof that may be purified from the soy protein hydrolysate compositions, soy/dairy protein hydrolysate compositions, canola protein hydrolysate compositions, maize protein hydrolysate compositions or wheat protein hydrolysate compositions of the invention. Typically, a pure polypeptide fragment constitutes at least about 80%, preferably, 90% and even more preferably, at least about 95% by weight of the total polypeptide in a given purified sample. A polypeptide fragment may be purified by a chromatographic method, such as size exclusion chromatography, ion exchange chromatography, affinity chromatography, hydrophobic interaction chromatography, reverse phase chromatography, and the like. For example, the polypeptide fragment may be selected from the group consisting of SEQ ID NOs: 5-274. Additionally, the invention also encompasses polypeptide fragments that are substantially similar in sequence to those selected from the group consisting of SEQ ID NOs:5-274. In one embodiment, polypeptide fragment may have at least 80, 81, 82, 83, 84, 85, 86, 87, 88, or 89% sequence identity to a polypeptide fragment selected from the group consisting of SEQ ID NOs:5-274. In another embodiment, the polypeptide fragment may have at least 90, 91, 92, 93, 94, 95, 96, 97, 98, or 99% sequence identity to a polypeptide fragment selected from the group consisting of SEQ ID NOs: 5-274. Methods for determining whether a polypeptide fragment shares a certain percentage of sequence identity with a sequence of the invention are presented above.

It is also envisioned that the protein hydrolysate compositions of the invention may further comprise a non-hydrolyzed (i.e., intact) protein. The non-hydrolyzed protein may be present in an essentially intact preparation (such as, e.g., soy curd, corn meal, milk, etc.) Furthermore, the non-hydrolyzed protein may be isolated from a plant-derived protein source (e.g., sources such as amaranth, arrowroot, barley, buckwheat, canola, cassava, channa (garbanzo), legumes, lentils, lupin, maize, millet, oat, pea, potato, rice, rye, sorghum, sunflower, tapioca, triticale, wheat, and so forth) or isolated from an animal protein material (examples of suitable isolated animal proteins include acid casein, caseinate, whey, albumin, gelatin, and the like). In preferred embodiments, the protein hydrolysate composition further comprises a non-hydrolyzed protein selected from the group consisting of barley, canola, lupin, maize, oat, pea, potato, rice, soy, wheat, animal, dairy, egg, and combinations thereof. The relative proportions of the protein hydrolysate and the non-hydrolyzed protein can and will vary depending upon the proteins involved and the desired use of the composition.

(III) Food Products Comprising a Protein Hydrolysate

A further aspect of the present invention is the provision of a food product comprising an edible material and any of the protein hydrolysate compositions described herein. Alternatively, the food product may comprise an edible material and any of the isolated polypeptide fragments described herein.

The selection of a particular protein hydrolysate composition to combine with an edible material can and will vary depending upon the desired food product. In some embodiments, the protein hydrolysate composition may be derived from soy protein. In other embodiments, the protein hydrolysate composition may be derived from barley, canola, lupin, maize, oat, pea, potato, rice, wheat, animal, egg, and combinations thereof. In still other embodiments, the protein hydrolysate composition may be derived from a combination of soy and at least one other protein source selected from the group consisting of barley, canola, lupin, maize, oat, pea, potato, rice, wheat, animal, dairy, and egg. In alternate embodiments, the protein hydrolysate composition may comprise a combination of different protein hydrolysates. In additional embodiments, the protein hydrolysate composition may comprise isolated or synthetic polypeptides selected from the group of amino acid sequences consisting of SEQ ID NO:5-274.

The selection of the appropriate edible material also will vary depending on the desired food product. The edible material may be a plant-derived material, an animal-derived material, or a biomaterial (i.e., a protein, a carbohydrate, a lipid, etc.) isolated from a plant-derived material, an animal-derived material, and so forth.

In one embodiment, the food product may be a beverage. Preferred beverages include ready-to-drink (RTD) beverages or dry-blended beverages (DBB). The beverage may be a substantially cloudy beverage or a substantially clear beverage. Non-limiting examples of suitable beverages include milk-based beverages, milk analog beverages (e.g., soymilk, rice milk, etc), weight management beverages, protein shakes, meal replacement drinks, coffee-based beverages, nutritional drinks, energy drinks, infant formulas, fruit juice-based drinks, fruit drinks, fruit-flavored drinks, vegetable-based drinks, sports drinks, and the like. The pH of the beverage will generally range from about pH 2.8 to about pH 7.5, preferably from about pH 6.5 to about pH 7.5, and more preferably, about pH 7.0.

In another embodiment, the food product may be a food bar, such as a granola bar, a cereal bar, a nutrition bar, or an energy bar. In still another embodiment, the food product may be a cereal-based product. Non-limiting examples of cereal-based food products include breakfast cereals, pasta, breads, baked products (i.e., cakes, pies, rolls, cookies, crackers), and snack products (e.g., chips, pretzels, etc.). The edible material of a cereal-based food product may be derived from wheat (e.g., bleached flour, whole wheat flour, wheat germ, wheat bran, etc.), corn (e.g., corn flour, cornmeal, cornstarch, etc.), oats (e.g., puffed oats, oatmeal, oat flour, etc), rice (e.g., puffed rice, rice flour, rice starch), and so forth. In yet another embodiment, the food product may be a "solid" dairy-based product. Non-limiting examples of suitable "solid" dairy-based food products include hard cheese products, soft cheese products, ice cream products, yoghurt products, frozen yoghurt products, whipped dairy-like products, sherbets, and the like. In an alternate embodiment, the food product may be a nutritional supplement. The nutritional supplement may be liquid or solid. In another alternate embodiment, the food product may be a meat product or a meat analog product. Examples of meat food products include, but are not limited to, processed meats, comminuted meats, and whole muscle meat products. The meat material may be animal meat or seafood meat. The meat analog may be a textured vegetable or dairy protein that mimics animal or seafood meat in texture. The meat analog may be part or all of the meat material in a meat food product.

The degree of hydrolysis of the protein hydrolysate composition will also vary depending upon the starting material used to make the hydrolysate and the desired food product. For example, with beverages comprising a soy-containing protein hydrolysate composition, it may be desirable to utilize a substantially more soluble and, at times, a substantially more translucent soy protein hydrolysate composition, such as a composition having a degree of hydrolysis closer to 6% DH than 1% DH. Likewise, in food products where it may be desirable to minimize the bitter sensory attribute, a soy protein hydrolysate composition having a degree of hydrolysis closer to 1% DH than to 6% DH may be selected. Additionally, in food products where it may be desirable to minimize the grain and soy/legume sensory attributes, a soy protein hydrolysate composition having a degree of hydrolysis closer to 6% DH than to 1% DH may be selected.

In a preferred embodiment, the food product may be a beverage, as detailed above. And suitable examples of protein hydrolysate compositions were detailed above. Non-limiting examples of suitable edible materials include skim milk, reduced fat milk, 2% milk, whole milk, cream, evaporated milk, yoghurt, buttermilk, dry milk powder, non-fat dry milk powder, milk proteins, acid casein, caseinate (e.g., sodium caseinate, calcium caseinate, etc.), whey protein concetrate, whey protein isolate, soy protein isolate, soy protein hydrolysate, whey hydrolysate, chocolate, cocoa powder, coffee, tea, fruit juices, vegetable juices, and so forth. The beverage food product may further comprise sweetening agents (such as glucose, sucrose, fructose, maltodextrin, sucralose, corn syrup, honey, maple syrup, etc.), flavoring agents (e.g., chocolate, cocoa, chocolate flavor, vanilla extract, vanilla flavor, fruit flavors, etc), emulsifying or thickening agents (e.g., lecithin, carrageenan, cellulose gum, cellulose gel, starch, gum, arabic, xanthan gum, and the like); stabilizing agents, lipid materials (e.g., canola oil, sunflower oil, high oleic sunflower oil, fat powder, etc.), preservatives (e.g., potassium sorbate, sorbic acid, and so forth), antioxidants (e.g., ascorbic acid, sodium ascorbate, etc.), coloring agents, vitamins, minerals, and combinations thereof.

DEFINITIONS

To facilitate understanding of the invention, several terms are defined below.

The term "degree of hydrolysis" refers to the percentage of the total peptide bonds that are cleaved which is measured by determining moles $NH^2$ present per 100 kilograms (kg) protein.

The term "endopeptidase" refers to an enzyme that hydrolyzes internal peptide bonds in oligopeptide or polypeptide chains. The group of endopeptidases comprises enzyme subclasses EC 3.4.21-25 (International Union of Biochemistry and Molecular Biology enzyme classification system).

A "food grade enzyme" is an enzyme that is generally recognized as safe (GRAS) approved and is safe when consumed by an organism, such as a human. Typically, the enzyme and the product from which the enzyme may be derived are produced in accordance with applicable legal and regulatory guidelines.

A "hydrolysate" is a reaction product obtained when a compound is cleaved through the effect of water. Protein hydrolysates occur subsequent to thermal, chemical, or enzymatic degradation. During the reaction, large molecules are broken into smaller proteins, soluble proteins, peptide fragments, and free amino acids.

The term "sensory attribute," such as used to describe terms like "grain," "soy/legume," or "bitter" is determined in accordance with the SQS Scoring System as specifically delineated in Example 6.

The term "soluble solids index" refers to the percentage of soluble proteins or soluble solids.

The terms "isolated soy protein" or "soy protein isolate," as used herein, refer to a soy material having a protein content of at least about 90% soy protein on a moisture free basis. An isolated soy protein is formed from soybeans by removing the hull and germ of the soybean from the cotyledon, flaking or grinding the cotyledon and removing oil from the flaked or ground cotyledon, separating the soy protein and carbohydrates of the cotyledon from the cotyledon fiber, and subsequently separating the soy protein from the carbohydrates.

The term "soy protein concentrate" as used herein is a soy material having a protein content of from about 65% to less than about 90% soy protein on a moisture-free basis. Soy protein concentrate also contains soy cotyledon fiber, typically from about 3.5% up to about 20% soy cotyledon fiber by weight on a moisture-free basis. A soy protein concentrate is formed from soybeans by removing the hull and germ of the soybean, flaking or grinding the cotyledon and removing oil from the flaked or ground cotyledon, and separating the soy protein and soy cotyledon fiber from the soluble carbohydrates of the cotyledon.

The term "soy flour" as used herein, refers to a comminuted form of defatted, partially defatted, or full fat soybean material having a size such that the particles can pass through a No. 100 mesh (U.S. Standard) screen. The soy cake, chips, flakes, meal, or mixture of the materials are comminuted into soy flour using conventional soy grinding processes. Soy flour has a soy protein content of about 49% to about 65% on a moisture free basis. Preferably the flour is very finely ground, most preferably so that less than about 1% of the flour is retained on a 300 mesh (U.S. Standard) screen.

The term "soy cotyledon fiber" as used herein refers to the polysaccharide portion of soy cotyledons containing at least about 70% dietary fiber. Soy cotyledon fiber typically contains some minor amounts of soy protein, but may also be 100% fiber. Soy cotyledon fiber, as used herein, does not refer to, or include, soy hull fiber. Generally, soy cotyledon fiber is formed from soybeans by removing the hull and germ of the soybean, flaking or grinding the cotyledon and removing oil from the flaked or ground cotyledon, and separating the soy cotyledon fiber from the soy material and carbohydrates of the cotyledon.

A "trypsin-like serine protease" is an enzyme that preferentially cleaves a peptide bond on the carboxyl terminal side of an arginine residue or a lysine residue.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compounds, products and methods without departing from the scope of the invention, it is intended that all matter contained in the above description and in the examples given below, shall be interpreted as illustrative and not in a limiting sense.

EXAMPLES

The following examples illustrate embodiments of the invention.

Example 1

Hydrolysis of Isolated Soy Proteins with the Trypsin Like Endopeptidase, TL1

Isolated soy protein was hydrolyzed into smaller peptide fragments in an attempt to increase its solubility and improve its sensory characteristics. The fungal trypsin-like peptidase from *Fusarium oxysporum*, TL1, the sequence of which is shown as SEQ ID NO:1 of the present application, was chosen because it cleaves peptide bonds at the C-terminal side of arginine or lysine residues, whereas other peptidases have been shown to cleave random peptide bonds in soy proteins.

An 8% slurry of isolated soy protein (ISP) was made by dispersing 320 g of SUPRO® 500E, Solae, St. Louis, Mo.) in 3680 g of water using moderate mixing to reduce foaming. Two drops of a defoamer were added, if necessary. The solution was heated to 80° C. for 5 min to inactivate any serine protease inhibitors that may have been present. The mixture was cooled to 50° C. and the pH was adjusted to 8.0 with food-grade KOH (a 50% w/w solution). Aliquots (800 mL) of the 8% soy protein slurry were incubated at 50° C. for 60 min in the presence of 0, 75 mg, 350 mg, 650 mg, or 950 mg of TL1/kg of soy protein. The samples were heated to 85° C. for 5 min to inactivate the enzyme. The samples were chilled on ice and stored at 4° C.

The degree of hydrolysis (% DH) refers to the percent of specific peptide bonds that were hydrolyzed (that is, the number of cleaved out of the total number of peptide bonds present in the starting protein). The % DH was estimated using the trinitrobenzene sulfonic acid (TNBS) method. This procedure is an accurate, reproducible and generally applicable procedure for determining the degree of hydrolysis of food protein hydrolysates. For this, 0.1 g of the soy protein hydrolysate was dissolved in 100 mL of 0.025 N NaOH. An aliquot (2.0 mL) of the hydrolysate solution was mixed with 8 mL of 0.05 M sodium borate buffer (pH 9.5). Two mL of the buffered hydrolysate solution was treated with 0.20 mL of 10% trinitrobenzene sulfonic acid, followed by incubation in the dark for 15 minutes at room temperature. The reaction was quenched by adding 4 mL of a 0.1 M sodium sulfite-0.1 M sodium phosphate solution (1:99 ratio), and the absorbance was read at 420 nm. A 0.1 mM glycine solution was used as the standard. The following calculation was used to determine the percent recovery for the glycine standard solution: [(absorbance of glycine at 420 nm-absorbance of blank at 420 nm)×(100/0.710)]. Values of 94% or higher were considered acceptable.

Table 1 presents the mean TNBS values and the % DH for each sample. It appears that hydrolysis began to plateau around 6% DH, which could reflect the number of arginine and lysine sites readily available to be cleaved. This experiment suggests that digestion with 350 mg/kg of TL1 for one hour produced sufficient hydrolysis products.

TABLE 1

Degree of Hydrolysis of Soy Protein Hydrolysates

| Sample # | Description | TNBS Value (moles $NH_2$ per 100 kg protein) | % DH |
| --- | --- | --- | --- |
| 0 | 0 TL1 mg/kg | 24 | 0 |
| 23-1 | 75 TL1 mg/kg | 51 | 3.0 |
| 23-2 | 350 TL1 mg/kg | 70 | 5.2 |
| 23-3 | 650 TL1 mg/kg | 75 | 5.8 |
| 24-4 | 950 TL1 mg/kg | 78 | 6.1 |

Example 2

SDS-PAGE Analysis of TL1 Hydrolysates

TL1 hydrolysates with 0.3% DH, 2.2% DH, 3.1% DH, 4.0% DH, and 5.0% DH were prepared essentially as described in Example 1. Aliquots of each, and non-hydrolyzed isolated soy protein, were resolved by SDS-PAGE using standard procedures. This analysis permitted comparison of molecular sizes of the polypeptides in the soy hydrolysates with those of the starting soy proteins. FIG. 1 presents an image of a Coomassie stained gel. The non-hydrolyzed isolated soy protein comprises polypeptides ranging in size from about 5 kDa to about 100 kDa. Although the size range of the polypeptides in the 0.3% DH hydrolysate was similar to that of the starting material, this hydrolysate contained additional small polypeptide fragments. The hydrolysates with higher % DH essentially lacked polypeptides larger than about 20-30 kDa, and all had additional small (<5 kDa) polypeptides. The polypeptide patterns of the 2.2% DH, 3.1% DH, and 4.0% DH hydrolysates were quite similar. The 5.0% DH hydrolysate, however, had a narrower range of polypeptide sizes (~0.1-20 kDa) than the other hydrolysates. In particular, the 7S and 11S subunit bands were not present in the 5.0% DH hydrolysate (see FIG. 1, lane 8).

Example 3

Analysis of Peptide Fragments in TL1 Hydrolysates by LC-MS

Peptide fragments in the TL1 hydrolysates prepared in Example 1 were identified by liquid chromatography mass spectrometry (LC-MS). Samples were prepared for LC-MS analysis by mixing an aliquot containing 2 mg of each TL1 hydrolysate with 0.1% formic acid (1 mL) in a glass vial and vortexing for 1-2 min. The mixture was centrifuged at 13,000 rpm for 5 min. An aliquot (25 µL) of the supernatant was injected into C18 analytical HPLC column (15 cm×2.1 mm id, 5 µm; Discovery Bio Wide Pore, Supelco®), Sigma-Aldrich, St. Louis, Mo.) on a HP®-1100 (Hewlett Packard; Palo Alto, Calif.) HPLC instrument. The elution profile is presented in Table 2; Solvent A was 0.1% formic acid; Solvent B was 0.1% formic acid in acetonitrile, the flow rate was 0.19 mL/min, and the column thermostat temperature was 25° C.

TABLE 2

HPLC Solvent Elution Profile

| Time (min) | Solvent A (%) | Solvent B (%) |
|---|---|---|
| 0 | 95 | 5 |
| 35 | 55 | 45 |
| 37 | 55 | 45 |
| 39 | 10 | 90 |
| 42 | 10 | 90 |
| 44 | 95 | 5 |
| 45 | 95 | 5 |

An aliquot (10 µL) of the LC eluent was delivered to the ESI-MS source using a splitter system for MS analysis. A Thermo Finnigan™ LCQ™ (Thermo Scientific, Waltham, Mass.) Deca ion trap mass spectrometer was used to analyze the peptides with data dependent MS/MS and data dependent MS/MS with dynamic exclusion scan events. ESI-MS was conducted at positive ion mode with capillary temperature 225° C., electrospray needle was set at a voltage 5.0 kV, and scan range from m/z 400-2000. The raw MS/MS data was deconvoluted by Sequest search engine (BIOWORKS software, Thermo Fisher Scientific, Waltham, Mass.) with no enzyme search parameters. Peptides were identified by searching a standard database such as the National Center for Biotechnology Information (NCBI) at the National Institutes of Health or Swiss-Prot from the Swiss Institute of Bioinformatics.

The peptides are presented in Table 3. Nearly every peptide fragment had an arginine or a lysine at the carboxyl terminus (three fragments had glutamine at the carboxyl terminus). Approximately twice as many fragments terminated with an arginine residue than with a lysine residue.

Identification of the peptide fragments revealed that hydrolysis products of the alpha-subunit of beta-conglycinin, beta-subunit of beta-conglycinin, glycinin subunit G1, glycinin subunit G3, and glycinin Gy4 were present in each TL1 hydrolysate. Many of the same peptide fragments were detected in each hydrolysate. The 5.8% and 6.1% DH hydrolysates also contained fragments from P 24 oleosin isoform A. The 6.1% DH hydrolysate revealed the presence of fragments from additional protein, trypsin inhibitor Kti3.

TABLE 3

Peptide Fragments in Hydrolysates with Different Degree of Hydrolysis (DH)

| Protein | 3.0% DH SEQ ID NO | Sequence | 5.2% DH SEQ ID NO | Sequence | 5.8% DH SEQ ID NO | Sequence | 6.1% DH SEQ ID NO | Sequence |
|---|---|---|---|---|---|---|---|---|
| Alpha-subunit of beta-conglycinin | 5 | YSNLKGK | 23 | SGDALR | 24 | FETLFK | 38 | SSSRK |
| | 6 | RFETLFK | 24 | FETLFK | 8 | SRDPIYSNK | 23 | SGDALR |
| | 7 | SPQLQNLR | 7 | SPQLQNLR | 9 | SSEDKPFNLR | 24 | FETLFK |
| | 8 | SRDPIYSNK | 8 | SRDPIYSNK | 7 | SPQLQNLR | 7 | SPQLQNLR |
| | 9 | SSEDKPFNLR | 25 | KTISSEDKPFNLR | 36 | EQQEEQPLEVR | 39 | FFEITPEK |
| | | | | | 25 | KTISSEDKPFNLR | 8 | SRDPIYSNK |
| | | | | | 37 | LQESVIVEISKEQIR | 37 | LQESVIVEISKEQIR |
| | | | | | | | 40 | VLFSREEGQQQGEQR |
| Beta-subunit of beta-conglycinin | 10 | SSEDEPFNLR | 26 | SPQLENLR | 26 | SPQLENLR | 42 | LLQR |
| | 11 | NFLAGEKDNVVR | 27 | LAGEKDNVVR | 27 | LAGEKDNVVR | 43 | FNKR |
| | | | 11 | NFLAGEKDNVVR | 11 | NFLAGEKDNVVR | 26 | SPQLENLR |
| | | | 28 | KTISSEDEPFNLR | 41 | LKVREDENNPFYLR | 11 | NFLAGEKDNVVR |
| | | | 29 | VREDENNPFYLR | | | | |
| Glycinin subunit G1 (proglycinin A1aB1b) | 12 | NNNPFK | 30 | PPQESQKR | 44 | PDNR | 45 | TLNR |
| | 13 | LSAEFGSLR | 13 | LSAEFGSLR | 45 | TLNR | 50 | SQQAR |
| | 14 | SQSDNFEYVSFK | 31 | LNALKPDNR | 46 | PQQR | 47 | YNFR |
| | 15 | PEEVIQHTFNLK | 32 | VFDGELQEGR | 47 | YNFR | 12 | NNNPFK |
| | 16 | FYLAGNQEQEFLK | 14 | SQSDNFEYVSFK | 12 | NNNPFK | 13 | LSAEFGSLR |
| | 17 | RFYLAGNQEQEFLK | 15 | PEEVIQHTFNLK | 13 | LSAEFGSLR | 48 | PQNFVVAAR |
| | | | 16 | FYLAGNQEQEFLK | 48 | PQNFVVAAR | 31 | LNALKPDNR |
| | | | | | 32 | VFDGELQEGR | 32 | VFDGELQEGR |
| | | | | | 49 | LAGNQEQEFLK | 14 | SQSDNFEYVSFK |
| | | | | | 14 | SQSDNFEYVSFK | 15 | PEEVIQHTFNLK |
| | | | | | 15 | PEEVIQHTFNLK | 16 | FYLAGNQEQEFLK |
| | | | | | 16 | FYLAGNQEQEFLK | | |
| Glycinin subunit G3 (glycinin A1bB2) | 18 | PPKESQR | 18 | PPKESQR | 19 | LSAQFGSLR | 18 | PPKESQR |
| | 19 | LSAQFGSLR | 19 | LSAQFGSLR | 120 | LAGNQEQEFLQ | 19 | LSAQFGSLR |
| | 20 | FYLAGNQEQEFLQ | 33 | PEEVIQQTFNLR | 18 | PPKESQR | | |
| | | | 20 | FYLAGNQEQEFLQ | | | | |
| Glycinin Gy4 A5A4B3 | 21 | SKKTQPR | 22 | PSEVLAHSYNLR | 51 | ADFYNPK | 51 | ADFYNPK |
| | 22 | PSEVLAHSYNLR | 34 | ISTLNSLTLPALR | 52 | MIIIAQGK | 52 | MIIIAQGK |
| | | | 35 | KQIVTVEGGLSVISPK | 53 | PETMQQQQQQK | 53 | PETMQQQQQQK |
| | | | | | 22 | PSEVLAHSYNLR | 22 | PSEVLAHSYNLR |
| | | | | | 35 | KQIVTVEGGLSVISPK | 34 | ISTLNSLTLPALR |
| | | | | | | | 35 | KQIVTVEGGLSVISPK |
| P 24 oleosin isoform A | | | | | 54 | HSER | 57 | TKEVGQDIQSK |
| | | | | | 55 | YEAGVVPPGAR | 56 | HHLAEAAEYVGQK |
| | | | | | 56 | HHLAEAAEYVGQK | | |

TABLE 3-continued

Peptide Fragments in Hydrolysates with Different Degree of Hydrolysis (DH)

| Protein | 3.0% DH SEQ ID NO | Sequence | 5.2% DH SEQ ID NO | Sequence | 5.8% DH SEQ ID NO | Sequence | 6.1% DH SEQ ID NO | Sequence |
|---|---|---|---|---|---|---|---|---|
| Trypsin inhibitor Kti3 | | | | | | | 58 59 | ILVVSK DAMDGWFR |

Example 4

Analysis of Peptide Fragments in TL1 Hydrolysate with a High Degree of Hydrolysis via MALDI-MS Peptide fragments in the 6.1% DH soy hydrolysate prepared in Example 1 were also analyzed by matrix-assisted laser desorption ionization time of flight mass spectrometry (MALDI-TOF/TOF-MS). The sample was prepared for and analyzed by HPLC as described in Example 3, except that the final elution step was extended to about 50 minutes and fractions were collected on a Bio-Rad® (Bio-Rad Laboratories, Hercules, Calif.) fraction collector at 1 minute intervals. Fractions #4-48 were evaporated completely on a Genevac® (Genevac, Ltd, UK) evaporator at <30° C.

For this, the dried samples were dissolved in 200 µL of a solution of 1% trifluoracetic acid (TFA) in 50% acetonitrile. An aliquot (1.5 µL) of each sample was mixed with 1.5 µL of MALDI matrix solution (6.2 mg of alpha-cyano-4-hydroxy cinnamic acid/ml of 36% methanol (v/v), 56% acetonitrile (v/v), and 8% water). The sample was vortexed, centrifuged, and 1 µL was spotted on a MALDI stainless steel target plate. The thirteen samples with high quality MS spectra were selected for further purification and MS/MS analysis. Each fraction was dried and resuspended in 10 µL of a solution of 0.1% formic acid in 1% acetonitrile in a PCR tube, vortexed for 30 sec, and centrifuged at 2000 rpm for 10 seconds. The vortexing and spinning was repeated 5 times. Peptide mixtures were purified by using a NuTip (10 µL porous graphite carbon SPE tip). A pre wetted (0.1% formic acid in 60% acetonitrile followed by equilibration with 0.1% formic acid) tip was used to extract peptides from the PCR tube containing the sample. The entire sample solution was drawn up into the tip and expelled back to the tube for a total of 50 times. The sample loaded tip was then washed (drawn and expelled) with 0.1% formic acid (10 µL) five times. Finally, the peptides were eluted from the tip with 10 µL of 0.1% formic acid in 60% acetonitrile. The elution process was repeated ten times using the same solvent mixture (10 µL). The pooled eluted sample solution was dried in a speed vacuum and resuspended in 1.5 µL of a solution of 1% TFA in 50% acetonitrile and 1.5 µL of the MALDI matrix solution. The mixture was vortexed for 30 seconds, centrifuged for 5 seconds at 2000 rpm, and 1 µL was spotted on a MALDI target plate. MS analysis was performed on MALDI-TOF/TOF instrument (ABI-4700). The instrument was equipped with ND:YAG (335 nm) and operated at a repetition rate of 200 Hz in both MS and MS/MS mode. The data were recorded with 20 KeV acceleration energy in the first TOF and the voltage m Einzel lens was set at 6 KeV. The MS/MS data were deconvoluted by MASCOT search engine (MATRIX SCIENCE) with no enzyme search parameters. Peptides were identified by searching a standard database such as NCBI or Swiss-Prot.

The peptides identified by MALDI-MS are presented in Table 4. Some of the same peptide fragments were identified in this analysis that were identified with LC-MS (ESI). For example, fragments of alpha-subunit of beta-conglycinin, beta-subunit of beta-conglycinin, glycinin subunit G1, and glycinin Gy4 were found in both analyses. The MALDI-MS analysis detected fragments of additional polypeptides, such as the alpha prime subunit of beta-conglycinin, glycinin subunit G2, and 62 K sucrose-binding protein precursor and seed maturation protein, LEA4.

TABLE 4

Peptide Fragments in 6.1% DH Hydrolysate-MALDI-MS

| Protein | SEQ ID NO: | Sequence |
|---|---|---|
| Alpha-subunit of beta-conglycinin | 7 | SPQLQNLR |
| | 25 | KTISSEDKPFNLR |
| | 40 | VLFSREEGQQQGEQR |
| Beta-subunit of beta-conglycinin | 60 | TISSEDEPFNLR |
| | 28 | KTISSEDEPFNLR |
| | 29 | VREDENNPFYLR |
| | 61 | FFEITPEKNPQLR |
| | 62 | SSNSFQTLFENQNGR |
| | 63 | QVQELAFPGSAQDVER |
| Alpha prime-subunit of beta-conglycinin | 64 | QQQEEQPLEVR |
| | 65 | TISSEDKPFNLR |
| Glycinin subunitG1 (proglycinin A1aB1b) | 66 | FLVPPQESQK |
| | 67 | FLVPPQESQKR |
| | 68 | VLIVPQNFVVAAR |
| | 16 | FYLAGNQEQEFLK |
| | 69 | RPSYTNGPQEIYIQQGK |
| | 70 | VFYLAGNPDIEYPETMQQQQQQK |
| Glycinin subunit G2 A2B1a | 71 | EAFGVNMQIVR |
| | 14 | SQSDNFEYVSFK |
| | 72 | NNNPFSFLVPPQESQR |
| | 73 | NLQGENEGEDGEDKGAIVTVK |
| | 74 | VFDGELQEGGVLIVPQNFAVAAK |
| | 75 | GKQQEEENEGSNILSGFAPEFLK |
| | 76 | PQNFAVAAK |
| Glycinin Gy4 A5A4B3 | 77 | NGLHLPSYSPYPR |
| | 78 | AIPSEVLAHSYNLR |
| | 70 | VFYLAGNPDIEYPETMQQQQQQK |
| | 79 | WQEQQDEDEDEDEDDEDEQIPSHPPR |
| | 80 | IKQGQHQQEEEEEGGSVLSGFSK |
| 62 K sucrose-binding protein precursor | 81 | LFDQQNEGSIFAISR |
| | 82 | LTEVGPDDDEKSWLQR |
| Seed maturation Protein; LEA4 | 83 | TNRGPGGTATAHNTRA |
| | 84 | HQTSAMPGHGTGQPTGH |

Example 5

Hydrolysis of Isolated Soy Proteins with TL1 or ALCALASE®

Isolated soy proteins were hydrolyzed with either TL1 or ALCALASE® 2.4 L, a microbial subtilisin protease available from Novozymes (Bagsvaerd, Denmark), so that the sensory attributes and functionality of the different hydrolysates could be compared. A slurry of 8% isolated soy protein was prepared by blending 72 g of SUPRO® 500E in 828 g of tap water using moderate mixing for 5 min. Two drops of defoamer were added. The pH of the slurry was adjusted to 8.0 with 2 N KOH. Aliquots (800 g) of the slurry were heated to 50° C. with mixing. Varying amounts of TL1 peptidase or ALCALASE® (ALC) protease were added to achieve targeted degrees of hydrolysis of 0, 1% DH, 2% DH, 4% DH, and 6% DH. An autotitrator was used to keep the pH of the reaction constant at pH 8.0. After incubating at 50° C. for a period of time to produce the desired degree of hydrolysis, the samples were heated to 85° C. for 5 min to inactivate the enzymes, and the solutions were adjusted to pH 7.0. The samples were chilled on ice and stored at 4° C. The degree of hydrolysis (% DH) was determined using the TNBS method (as described in Example 1). Table 5 presents the amounts of enzymes added, the reaction times, the volumes of KOH added to titrate the pH during the reaction, the mean TNBS values, and the % DH.

TABLE 5

TL1 and ALCALASE ® Hydrolysates

| Sample # | Enzyme | Time (min) | KOH (mL) | TNBS Value (moles $NH_2$ per 100 kg protein) | % DH |
|---|---|---|---|---|---|
| 0 | 0 | 30 | 0 | 23.7 | 0 |
| 46-1 | 0.0182% ALCALASE ® | 30 | 3.2 | 34.8 | 1.3 |
| 46-2 | 0.0394% ALCALASE ® | 30 | 5.6 | 45.8 | 2.5 |
| 46-5 | 0.1018% ALCALASE ® | 30 | 8.7 | 52.1 | 3.2 |
| 46-9 | 0.3462% ALCALASE ® | 30 | 19.2 | 75.9 | 5.9 |
| 46-4 | 30 mg/kg TL1 | 28 | 3.1 | 32.1 | 1.0 |
| 46-3 | 70 mg/kg TL1 | 22 | 5.9 | 40.4 | 1.9 |
| 46-8 | 250 mg/kg TL1 | 12 | 8.5 | 50.3 | 3.0 |
| 46-7 | 400 mg/kg TL1 | 40 | 19.2 | 69.1 | 5.1 |

Example 6

Sensory Analysis of TL1 and ALCALASE® Hydrolysates

A proprietary sensory screening method, the Solae Qualitative Screening (SQS) method, was used to assess the flavor characteristics of the TL1 and ALCALASE® hydrolysates prepared in Example 5. This method is based upon a direct comparison between a test sample and a control sample, and it provides both qualitative and directional quantitative differences. A panel of seven trained assessors was provided with aliquots of each sample (diluted to a 5% slurry) and a control sample that was a 5% slurry of unhydrolyzed isolated soy protein. The pH of each solution was adjusted to 7.0 with food grade phosphoric acid.

The evaluation protocol comprised swirling a cup three times, while keeping the bottom of the cup on the table. After the sample sat for 2 seconds, each assessor sipped about 10 mL (2 tsp), swished it about her/his mouth for 10 seconds, and then expectorated. The assessor then rated the differences between the test sample and the control sample according to the scale presented in Table 6.

TABLE 6

SQS Scoring System

| SQS Score | Scale | Definition |
|---|---|---|
| 5 | Match | The test sample has virtually identical sensory characteristics to the control sample by appearance, aroma, flavor, and texture. |
| 4 | Slight difference | The test sample has one or multiple 'slight' differences from the control sample. These differences might not be noticed if not in a side-by-side comparison with the control. |
| 3 | Moderate difference | The test sample has one or multiple 'moderate' differences from the control sample. These differences would be noticeable in a side-by-side comparison of the two samples after one tasting of each. |
| 2 | Extreme difference | The test sample has one or multiple 'extreme' differences from the control sample. These differences would be noticed even if not in a side-by-side comparison. |
| 1 | Reject | The test sample has obvious defects that make it different from the control sample. |

Table 7 presents the mean SQS scores for each sample. The TL1 hydrolysates were generally rated as moderately different from the control sample (which was untreated isolated soy protein). The ALCALASE® (ALC) hydrolysates were rated as having from slight to extreme differences from the control.

TABLE 7

SQS Scores for TL1 and ALCALASE ® Hydrolysates

| % DH TL1 | SQS Score | % DH ALCALASE ® | SQS Score |
|---|---|---|---|
| 0 | 4.7 | 0 | 4.7 |
| 1.0 | 3.6 | 1.3 | 3.9 |
| 1.9 | 3.1 | 2.5 | 3.6 |
| 3.0 | 3.1 | 3.2 | 3.9 |
| 5.1 | 3.3 | 5.9 | 2.3 |

If a test sample was rated as different from the control sample (i.e., had an SQS score of 2, 3, or 4), then the test sample was further evaluated to provide diagnostic information on how the test sample differed from the control sample. Thus, if the test sample had slightly more, moderately more, or extremely more of an attribute (see Table 8) than the control sample, then scores of +1, +2, +3, respectively, were assigned. Likewise, if the test sample had slightly less, moderately less, or extremely less of the attribute than the control sample, then scores of −1, −2, −3, respectively, were assigned. This analysis provided an assessment of the directional quantitative differences between the test sample and the control sample.

TABLE 8

SQS Lexicon

| Attribute | Definition | References |
|---|---|---|
| Green | The general category of aromatics associated with green vegetation including stems, grass, leaves and green herbs. | Fresh cut grass, green beans, tomato vines |

TABLE 8-continued

SQS Lexicon

| Attribute | Definition | References |
|---|---|---|
| Grain | The aromatics associated with the total grain impact, which may include all types of grain and different stages of heating. May include wheat, whole wheat, oat, rice, graham flour, etc. | All-purpose wheat flour in a water paste, cream of wheat, whole wheat pasta |
| Soy/Legume | The aromatics associated with legumes/soybeans; may include all types and different stages of heating. | Unsweetened SILK ™ soymilk, canned soybeans, tofu |
| Cardboard/Woody | The aromatics associated with dried wood and the aromatics associated with slightly oxidized fats and oils, reminiscent of a cardboard box. | Toothpicks, water from cardboard soaked for 1 hour |
| Sweet | The taste on the tongue stimulated by sucrose and other sugars, such as fructose, glucose, etc., and by other sweet substances, such as saccharin, Aspartame, and Acesulfame-K. | Sucrose solutions: 2%, 5%, 10% |
| Sour | The taste on the tongue stimulated by acid, such as citric, malic, phosphoric, etc. | Citric acid solutions: 0.05%, 0.08%, 0.15% |
| Salt | The taste on the tongue associated with sodium salts. | Sodium chloride solutions: 0.2%, 0.35%, 0.5% |
| Bitter | The taste on the tongue associated with caffeine and other bitter substances, such as quinine and hop bitters. | Caffeine solutions: 0.05%, 0.08%, 0.15% |
| Astringent | The shrinking or puckering of the tongue surface caused by substances such as tannins or alum. | Alum solutions: 0.005%, 0.007%, 0.01% |

Figure 2:
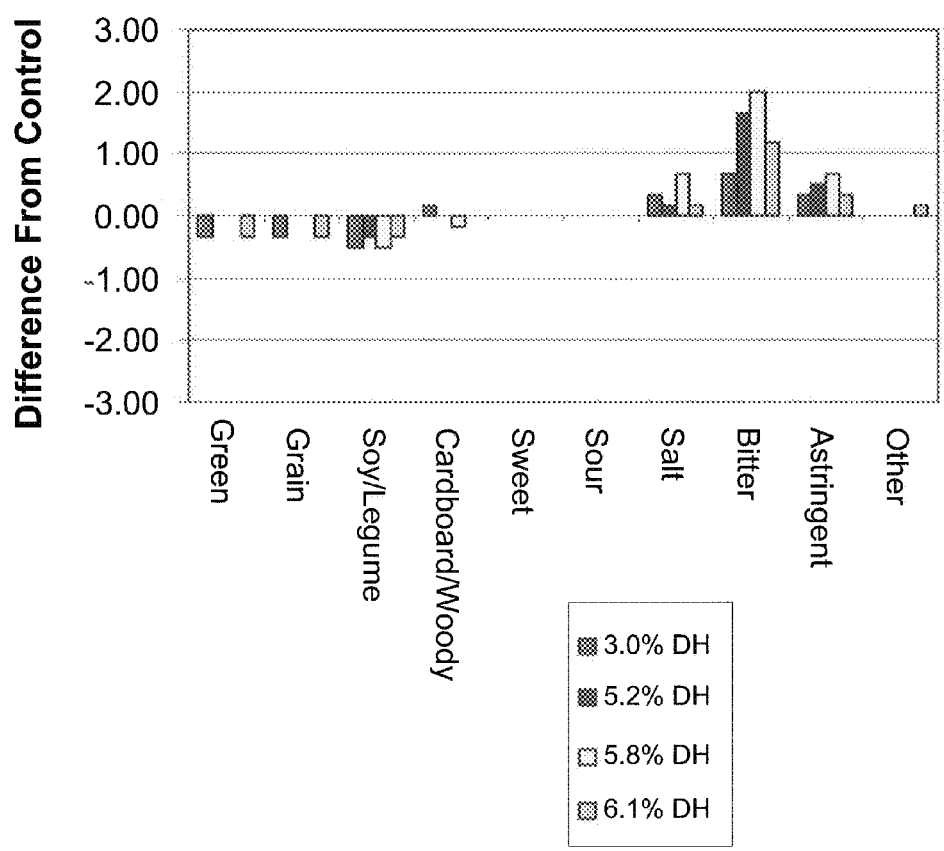
FIG. 2 presents the diagnostic scores of TL1 hydrolysates and ALCALASE® hydrolysates at 5.0% solids as evaluated by trained assessors. The identity and degree of hydrolysis (% DH) of each hydrolysate are presented below each plot. Positive scores indicate the hydrolysate had more of the sensory attribute than the control sample, and negative scores indicate the hydrolysate has less of the sensory attribute than the control sample. The control sample was non-hydrolyzed isolated soy protein. (A) Presents the scores for TL1 and ALCALASE® (ALC) hydrolysates with degrees of hydrolysis less than about 2.5% DH. (B) Presents the scores for TL1 and ALCALASE® (ALC) hydrolysates with degrees of hydrolysis greater than 3% DH.
Figure 2A:
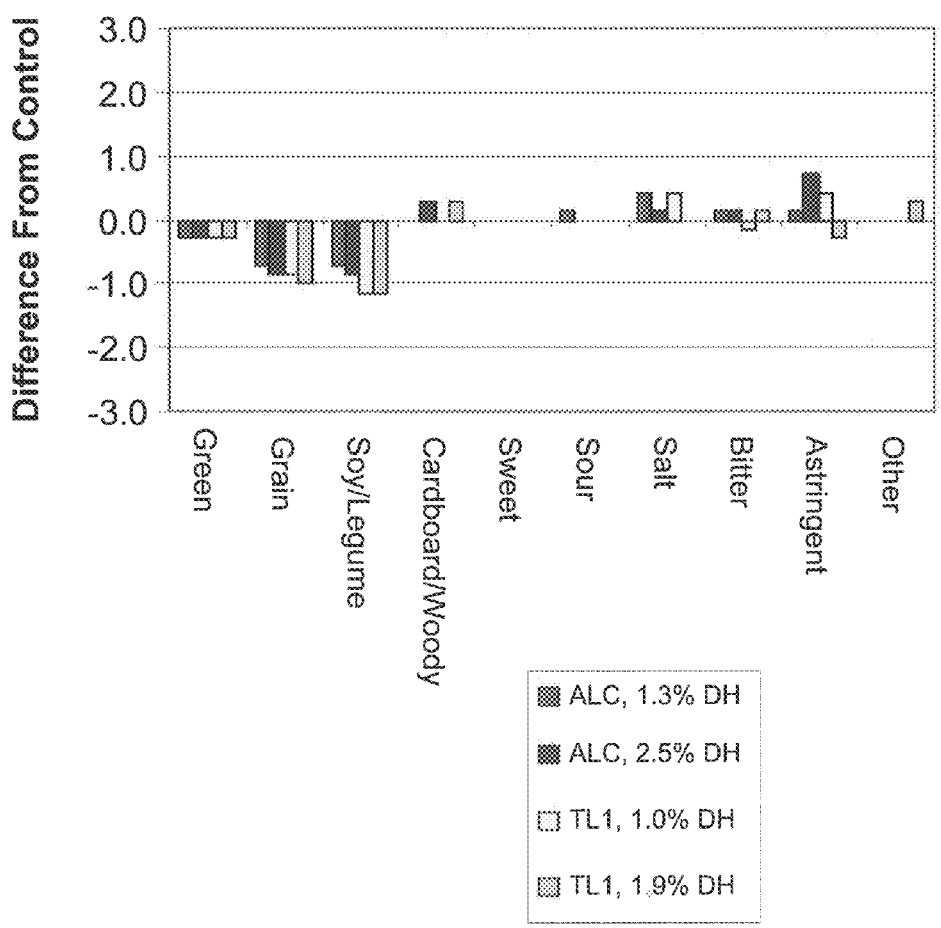
Figure 2B:
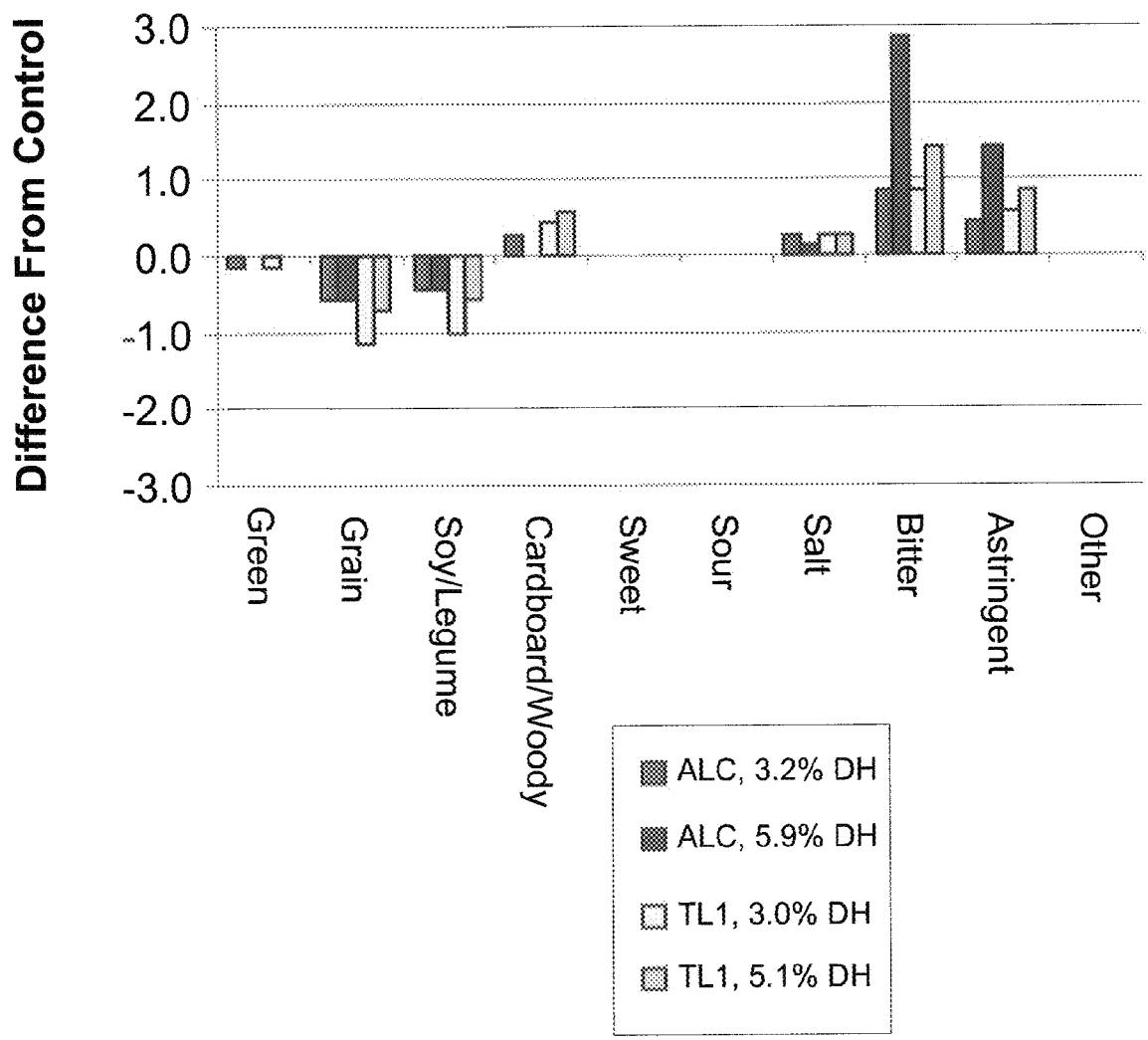

The directional differences of nine flavor attributes are presented in FIGS. 2A and 2B for hydrolysates with similar % DH levels. At all % DH levels, the TL1 hydrolysates had larger decreases in grain and soy/legume attributes and smaller increases in astringency and bitterness than did the ALC hydrolysates. The highest % DH ALC hydrolysates had particularly large increases in bitterness relative to the control.

Example 7

Solubility of TL1 and ALCALASE® Hydrolysates

Figure 3A:
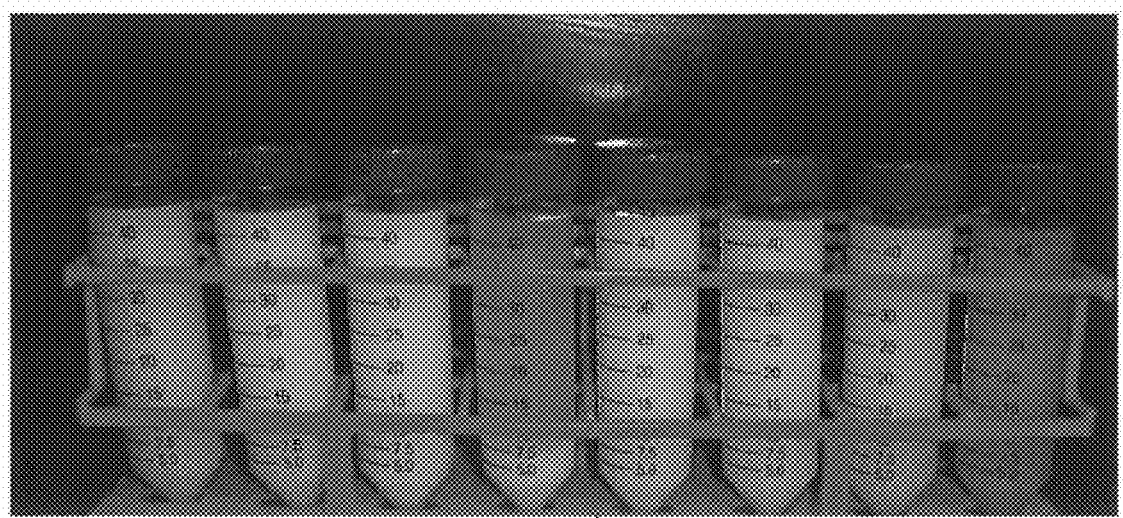
FIG. 3 compares the solubility of ALCALASE® and TL1 hydrolysates. The enzyme and degree of hydrolysis (% DH) of each is presented below each tube. (A) Presents tubes of ALCALASE® (ALC) and TL1 hydrolysates (at 2.5% solids) stored at pH 7.0 for two weeks at 4° C. (B) Presents TL1 and ALCALASE® (ALC) hydrolysates (at 2.5% solids) stored at pH 8.2 for three weeks at 4° C.
Figure 3B:
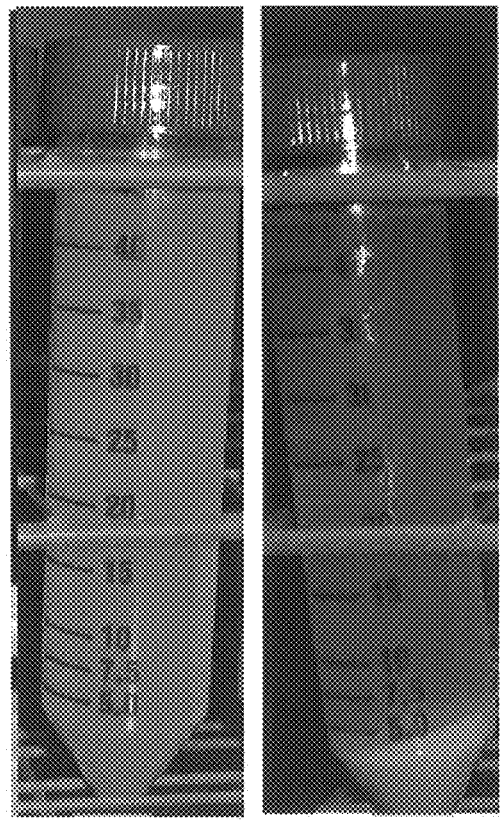

The solubility of each of the TL1 and ALCALASE® hydrolysates prepared in Example 5 was estimated by diluting the hydrolysates to 2.5% solids and storing them at 4° C. at pH 7.0 for one week. The samples were evaluated visually; a photographic image is presented in FIG. 3A. All of the TL1 hydrolysates had little sediment, but the 5.1% DH TL1 hydrolysate also had increased transparency relative to those with lower % DH. In contrast, the ALC hydrolysate with the highest % DH had a significant amount of sediment. FIG. 3B presents images of tubes of a 6.1% DH TL1 hydrolysate and a 13.8% DH ALC hydrolysate diluted to 2.5% solids that were stored at pH 8.2 at 4° C. for three weeks. The TL1 hydrolysate had no sediment, indicating that it was stable for an extended period of time at pH 8.2 at 4° C., whereas the ALC hydrolysate had sediment.

Figure 4A:
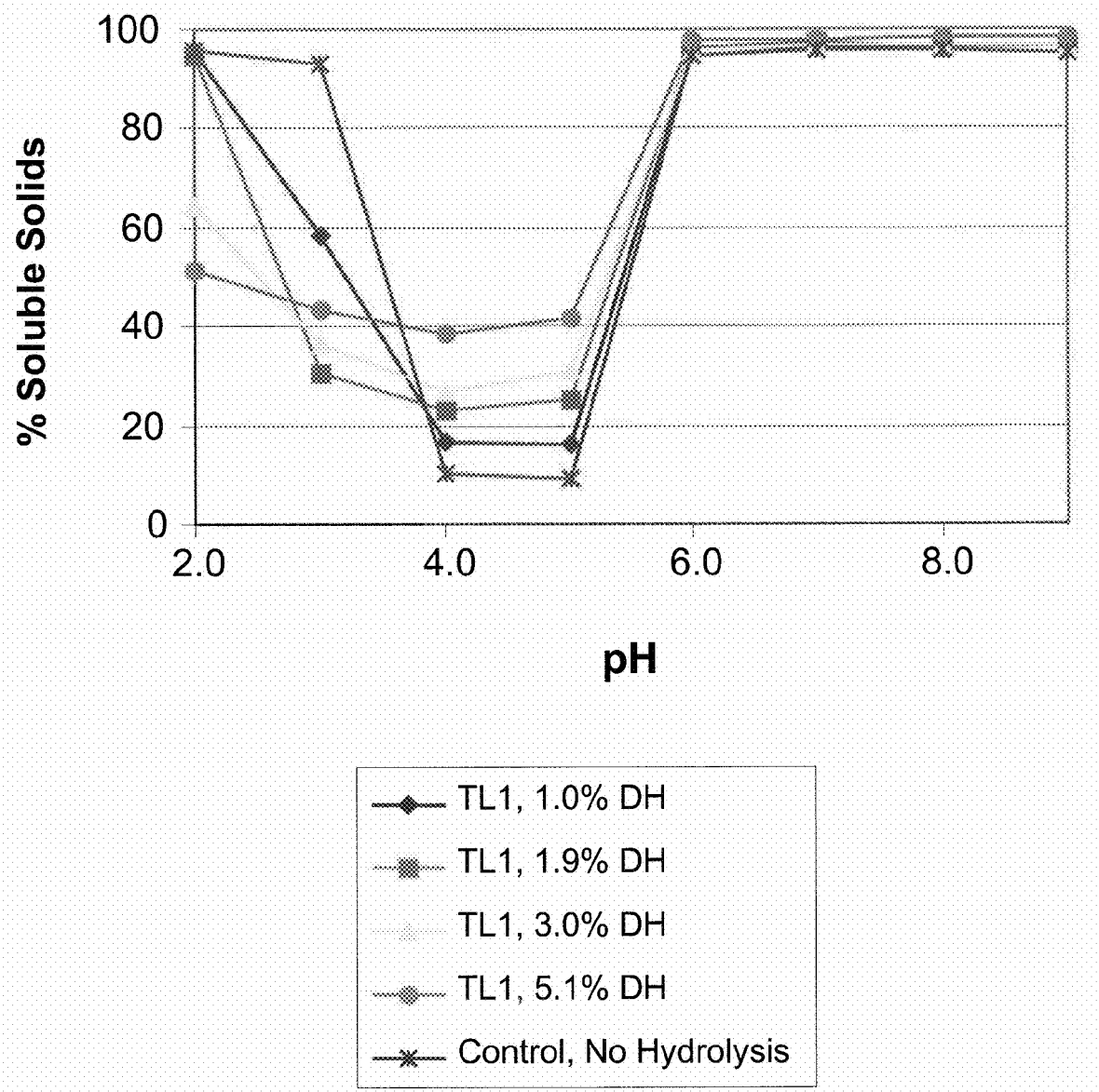
FIG. 4 presents solubility plots of TL1 and ALCALASE® hydrolysates. The percent of soluble solids (i.e., soluble solids index) of each hydrolysate (at 2.5% solids) is plotted as a function of pH. The identity and degree of hydrolysis (% DH) of each hydrolysate is presented below each plot. (A) Presents solubility curves for TL1 hydrolysates. (B) Presents solubility curves for ALCALASE® (ALC) hydrolysates. (C) Presents a direct comparison of the solubility of selected TL1 and ALCALASE® (ALC) hydrolysates.
Figure 4B:
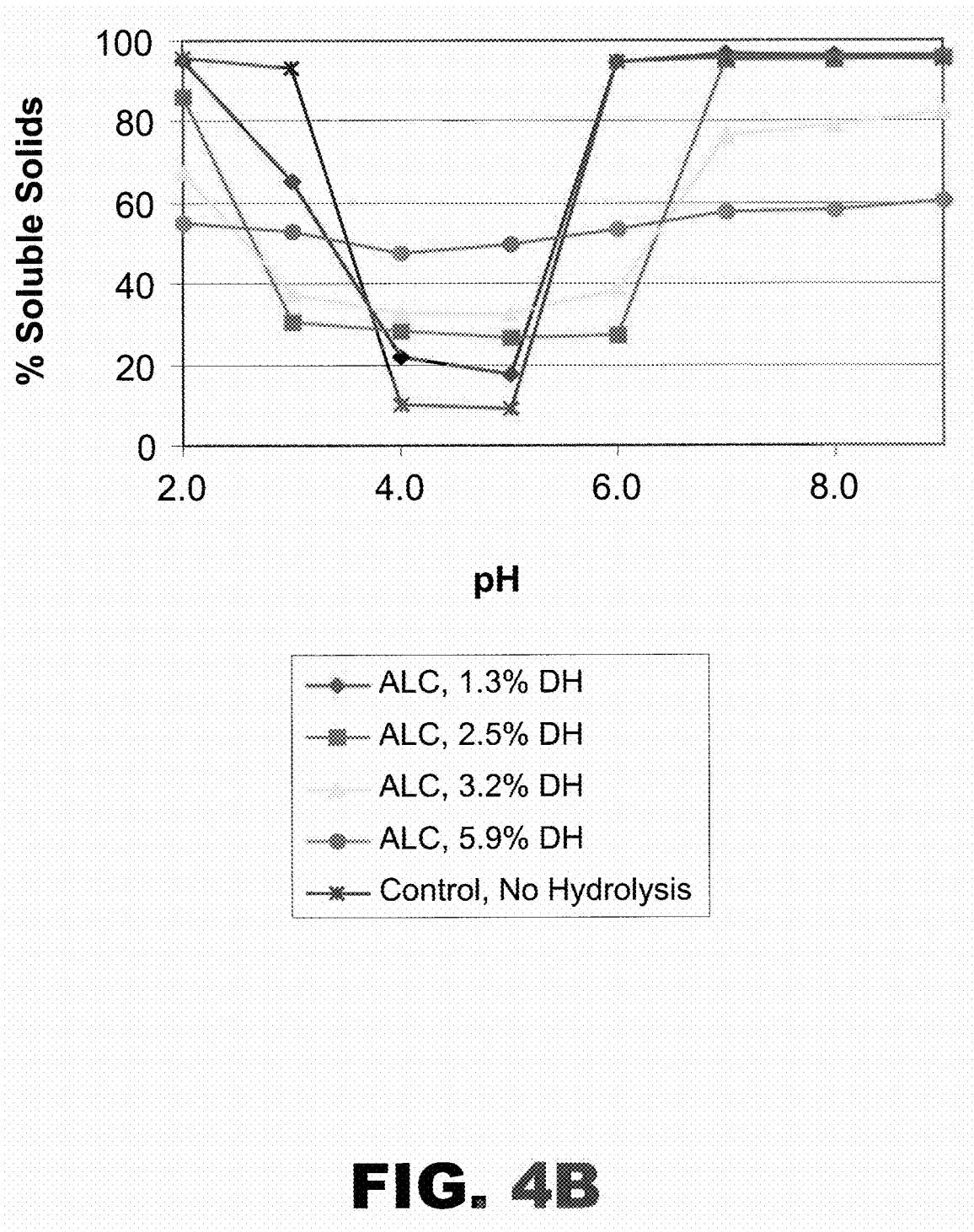
Figure 4C:
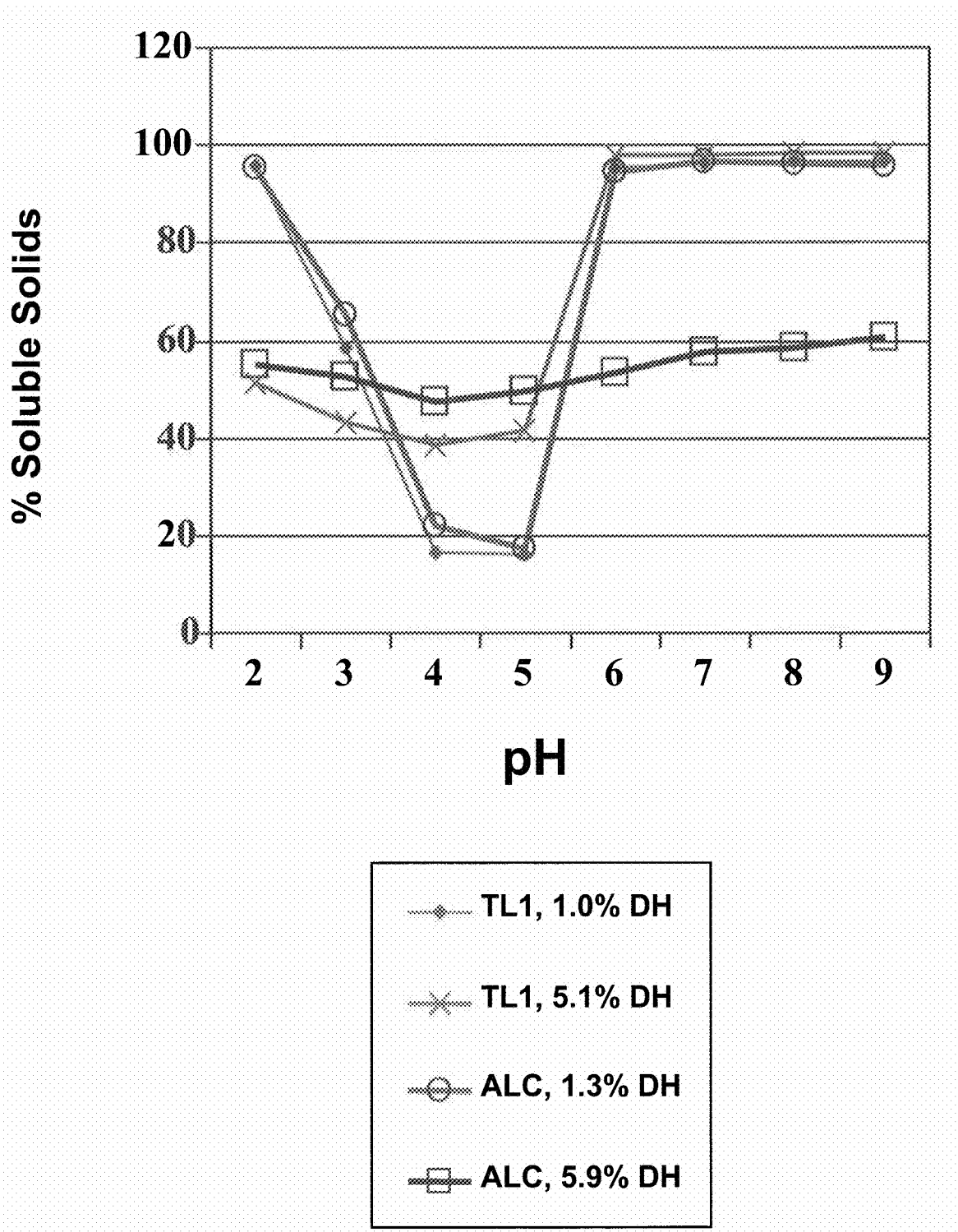

The effect of pH on solubility was tested in each of the TL1 and ALC hydrolysates prepared in Example 5. Aliquots of each were adjusted to pH 2, pH 3, pH 4, pH 5, pH 6, pH 7, pH 8, or pH 9, and the samples were centrifuged at 500×g for 10 min. The amount of solid matter in the solution before centrifuging was compared to the amount of solid matter in solution after centrifuging to give the soluble solids index (SSI). The % soluble solids of the TL1 and ALC hydrolysates are presented as a function of pH in FIGS. 4A and 4B, respectively. All of the solutions had reduced solubility at pH levels of about pH 4 to pH 5 (i.e., the isoelectric point of soy protein), and somewhat increased solubility at lower pH values. At higher pH values, however, all of the TL1 hydrolysates had excellent solubility at levels above pH 6.0 (FIG. 4A), but some of the ALC hydrolysates had reduced solubility at the higher pH levels (FIG. 4B). FIG. 4C presents a direct comparison of the solubility of TL1 and ALC hydrolysates at low and high % DH as a function of pH.

Example 8

Transmittance of TL1 Hydrolysates

The transmittance of some of the TL1 hydrolysates prepared in Example 5 was measured. For this, the 1% DH and 5.1% DH TL1 hydrolysates were prepared with different percentages of solids (i.e., 0.5%, 1.0%, 1.5%. 2.0%, and 2.5%).

An aliquot of each protein slurry was placed in a TURBISCAN® Lab Expert unit (Formulaction, I'Union, France) and the transmittance was recorded every second for a total of 60 seconds. Table 9 presents the average percent transmittance for each sample. The 5.1% DH TL1 hydrolysate had 37.4% transmittance at 0.5% solids as compared to 1.3% transmittance for the 1.0% DH hydrolysate at 0.5% solids. These data confirm what was observed visually (see FIG. 3A).

TABLE 9

Transmittance of TL1 Hydrolysates

| | % Transmittance | | | | |
|---|---|---|---|---|---|
| % DH | 2.5% solids | 2.0% solids | 1.5% solids | 1.0% solids | 0.5% solids |
| 1.0 | 0.0 | 0.0 | 0.1 | 0.2 | 1.3 |
| 5.1 | 2.1 | 4.2 | 8.0 | 16.6 | 37.4 |

Example 9

Bitterness Analysis of Soy Hydrolysates Prepared with TL1 or Other Endopeptidases Isolated soy proteins were hydrolyzed with TL1, ALCALASE® (ALC), or lysyl endopeptidase from *Achromobacter lyticus* (SP3; SEQ ID NO:4) essentially as described in Examples 1 and 5. The enzyme concentrations and reactions conditions were selected to give % DH values of about 5-6% DH, as determined by the TNBS method as described in Example 1. The hydrolysates were presented to a panel of five assessors for evaluation, focusing on bitterness, using the SQS method described in Example 6.

The mean SQS scores and diagnostic bitterness scores are presented in Table 10. The TL1 and SP3 hydrolysates were rated as having slight differences from the control sample (non-hydrolyzed isolated soy protein). Likewise the TL1 and SP3 hydrolysates were rated just slightly less bitter than the control sample. In contrast, the ALC hydrolysate was rated as extremely different and extremely more bitter than the control sample.

TABLE 10

SQS Analysis of Hydrolysates.

| Sample | SQS score (mean) | Bitterness score (mean) |
|---|---|---|
| No enzyme | 4.5 | −0.2 |
| TL1 | 3.8 | −0.7 |
| SP3 | 4.3 | −0.2 |
| ALC | 2.2 | +2.8 |

Example 10

Physical Properties of Pilot Plant TL1 Hydrolysates

The production of TL1 hydrolysates of isolated soy protein was scaled up from bench scale to a larger pilot plant scale, and the sensory and functional characteristics of the hydrolysates were analyzed. For this, the starting material was soy protein curd. To produce the soy protein curd material, soy flakes, soy flour, or soy grit was serially extracted with aqueous solutions from about pH 6.5 to about pH 10 to separate the protein in the flakes/flour/grit from insoluble materials such as fiber. A low level of sulfite was added to the extraction media at 0.05-0.15% based on the flake weight. The flakes, flour, or grit was extracted with an aqueous sodium hydroxide solution of about pH 6.5-7.0 for the first extraction and then extracted with a solution of about pH 8.5-10 for the second extraction. The weight ratio of the water to the soy flake/flour/grit material was from about 8:1 to about 16:1.

After extraction, the extract was separated from the insoluble materials by filtration or by centrifugation. The pH of the separated extract was then adjusted with a suitable acid to about the isoelectric point of soy protein (about pH 4-5, or preferably pH 4.4-4.6) to precipitate a soy protein curd so that the soy protein could be separated from soy solubles, including flatulence inducing oligosaccharides and other water soluble carbohydrates. Suitable edible acids include hydrochloric acid, sulfuric acid, nitric acid, or acetic acid. The precipitated protein material (curd) was separated from the extract (whey) by centrifugation to produce the soy protein curd material. The separated soy protein curd material was washed with water to remove residual solubles, at a weight ratio of water to protein material of about 5:1 to about 12:1.

The soy protein curd material was first neutralized to about pH 8.0 to about pH 9.0, preferably about pH 8.0-8.5, with an aqueous alkaline solution or an aqueous alkaline earth solution, such as a sodium hydroxide solution or a potassium hydroxide solution. The neutralized soy protein curd was heated and cooled, preferably by jet cooking and flash cooling. The soy protein material was then treated with TL1 enzyme at a temperature and for a time effective to hydrolyze the soy protein material so that the soy protein hydrolysate had a TNBS value of about 35-55. The enzyme was added to the soy protein material at a concentration of from 0.005% to 0.02% enzyme protein based on the protein curd weight basis. The enzyme was contacted with the soy protein curd material at a temperature of from 40° C. to 60° C., preferably at about 50° C. for a period of from 30 minutes to 120 minutes, preferably from 50 minutes to 70 minutes, to hydrolyze the protein. The hydrolysis was terminated by heating the hydrolyzed soy protein material to a temperature effective to inactivate the enzyme. Most preferably the hydrolyzed soy protein curd material was jet cooked to inactivate the enzyme, and flash cooled then spray-dried as described above.

Table 11 presents the reaction parameters for a typical set of hydrolysates. The degree of hydrolysis was determined using the TNBS method, essentially as described in Example 1. The TNBS value and % DH of each sample are also presented in Table 11. Control samples included non-hydrolyzed isolated soy protein (i.e., SUPRO® 500E) and essentially a commercially available isolated soy protein hydrolysate (i.e., SUPRO® XT 219 hydrolyzed with a mixture of enzymes to 2.8% DH).

TABLE 11

Pilot Plant TL1 Hydrolysates.

| Sample # | pH, Temperature | Time (min) | Dose (mg enzyme protein/kg solids) | TNBS Value (moles $NH_2$ per 100 kg protein) | % DH |
|---|---|---|---|---|---|
| 5-2 | Control (non-hydrolyzed protein) | | | 24.3 | 0 |
| 5-3 | Control (hydrolyzed protein) | | | 49.3 | 2.8 |
| 5-7 | 8.0, 50° C. | 30 | 10 | 26.7 | 0.3 |
| 5-8 | 8.0, 50° C. | 30 | 25 | 32.1 | 0.9 |
| 5-4 | 9.5, 50° C. | 30 | 50 | 35.8 | 1.3 |
| 5-9 | 8.0, 50° C. | 30 | 50 | 38.1 | 1.6 |
| 5-5 | 8.0, 50° C. | 120 | 50 | 42.1 | 2.0 |
| 5-1 | 8.0, 50° C. | 120 | 50 | 48.0 | 2.7 |
| 5-6 | 8.0, 50° C. | 120 | 100 | 58.2 | 3.8 |
| 5-10 | 8.0, 50° C. | 120 | 200 | 69.9 | 5.2 |

Figure 5:
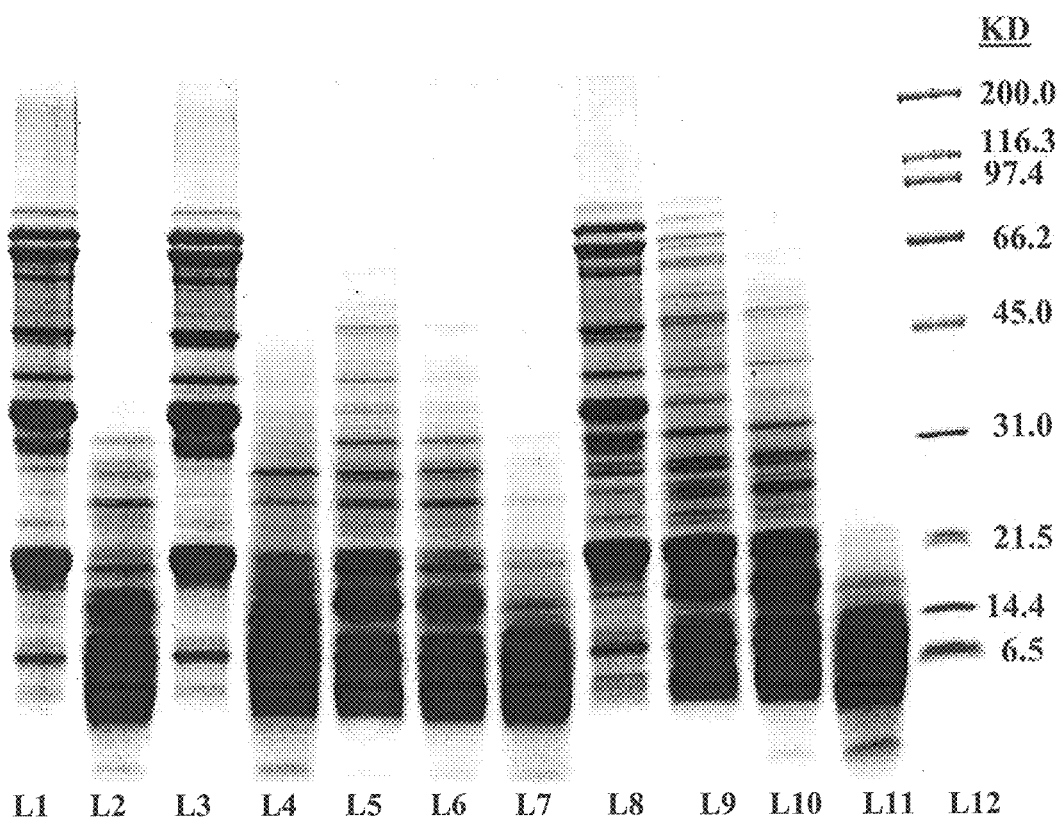
FIG. 5 illustrates the hydrolysis of soy protein material with TL1 at a pilot plant scale. Shown is an image of a Coomassie-stained SDS-polyacrylamide gel in which the TL1 hydrolysates and control samples were resolved. Lane 1 (L1) and lane 3 (L3) contain non-hydrolyzed soy protein; lane 2 (L2) contains a 2.7% DH TL1 hydrolysate; lane 4 (L4) contains a hydrolyzed control sample (SUPRO® XT 219 hydrolyzed to 2.8% DH with a mixture of enzymes); lanes 5-11 (L5-L11) contain TL1 hydrolysates with 1.3% DH, 2.0% DH, 3.8% DH, 0.3% DH, 0.9% DH, 1.6% DH, and 5.2% DH, respectively. Lane 12 (L12) contains a molecular weight standard, With the sizes in kiloDaltons (kDa) indicated to the right of the gel.

The TL1 hydrolysates and control samples were analyzed by SDS PAGE using standard procedures, and FIG. 5 presents an image of the gel. This analysis revealed that all of the major soybean storage protein subunits were cleaved by TL1.

Example 11

Solubility and Viscosity of Pilot Plant TL1 Hydrolysates

Figure 6:
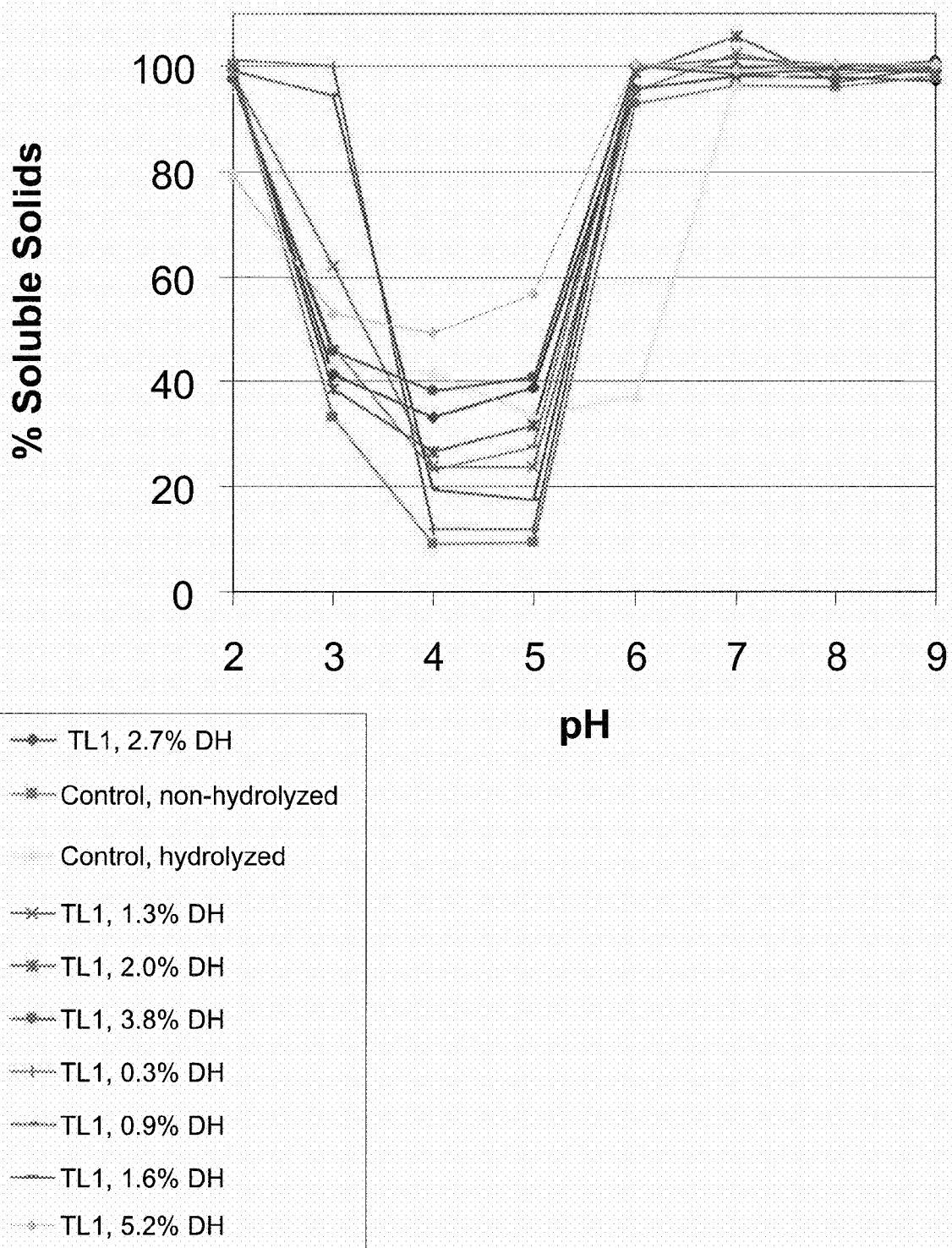
FIG. 6 presents solubility plots of the pilot plant TL1 hydrolysates and control samples. The degree of hydrolysis (% DH) for each hydrolysate is presented below the plot.

The solubility of the pilot plant TL1 hydrolysates and control samples prepared in Example 10 was also examined. Aliquots of each sample were adjusted to pH 2, pH 3, pH 4, pH 5, pH 6, pH 7, pH 8, and pH 9 and the soluble solids index (SSI) was determined, essentially as described in Example 7. As shown in FIG. 6, all of the TL1 hydrolysates samples were nearly 100% soluble at pH levels of pH 6 and above, while the hydrolyzed control sample was only approximately 40% soluble at pH 6. Furthermore, as the degree of hydrolysis increased, the solubility at the isoelectric point (i.e., around pH 4-5) increased.

Figure 7:
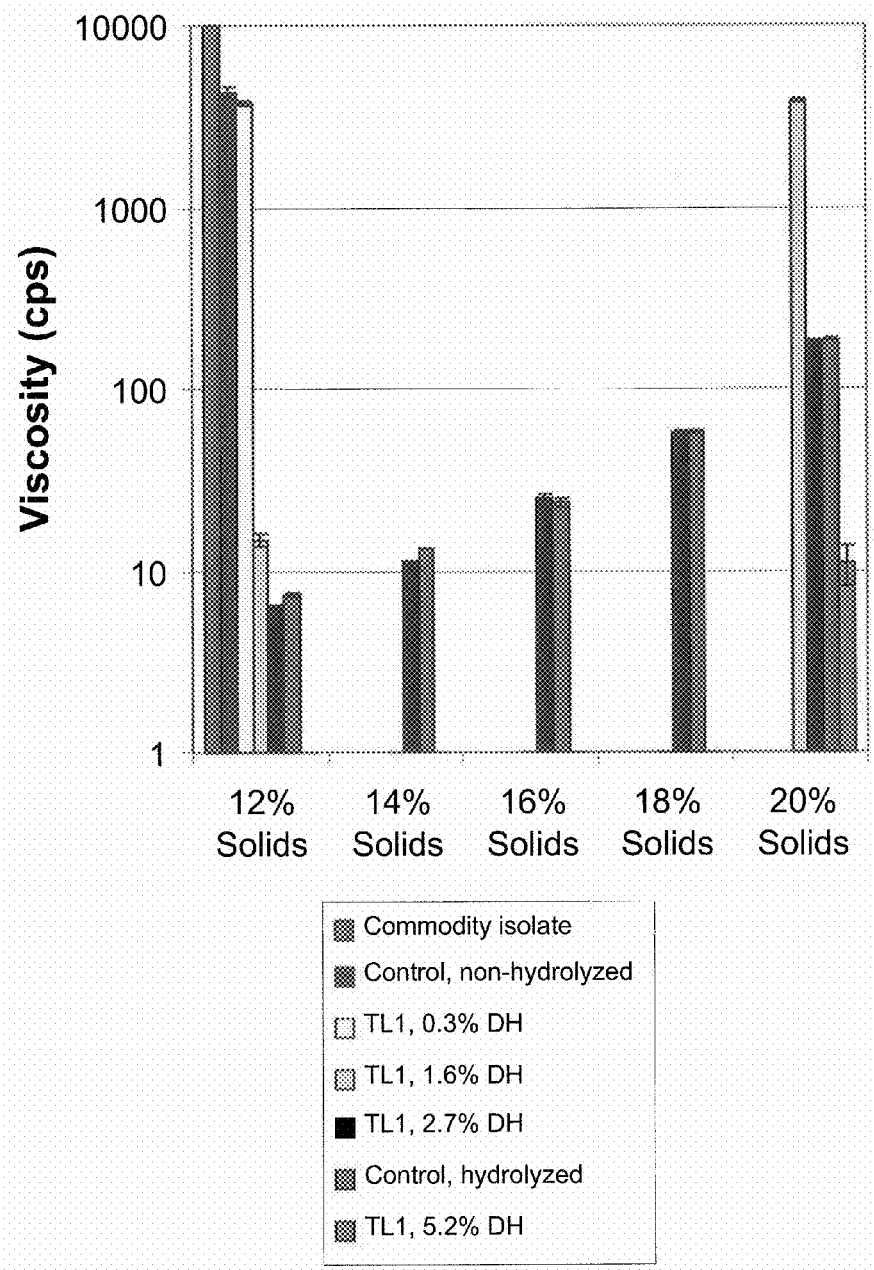
FIG. 7 presents a plot of the viscosity of the pilot plant TL1 hydrolysates and control samples. The degree of hydrolysis (% DH) of each hydrolysate is presented below the plot.
Figure 8:
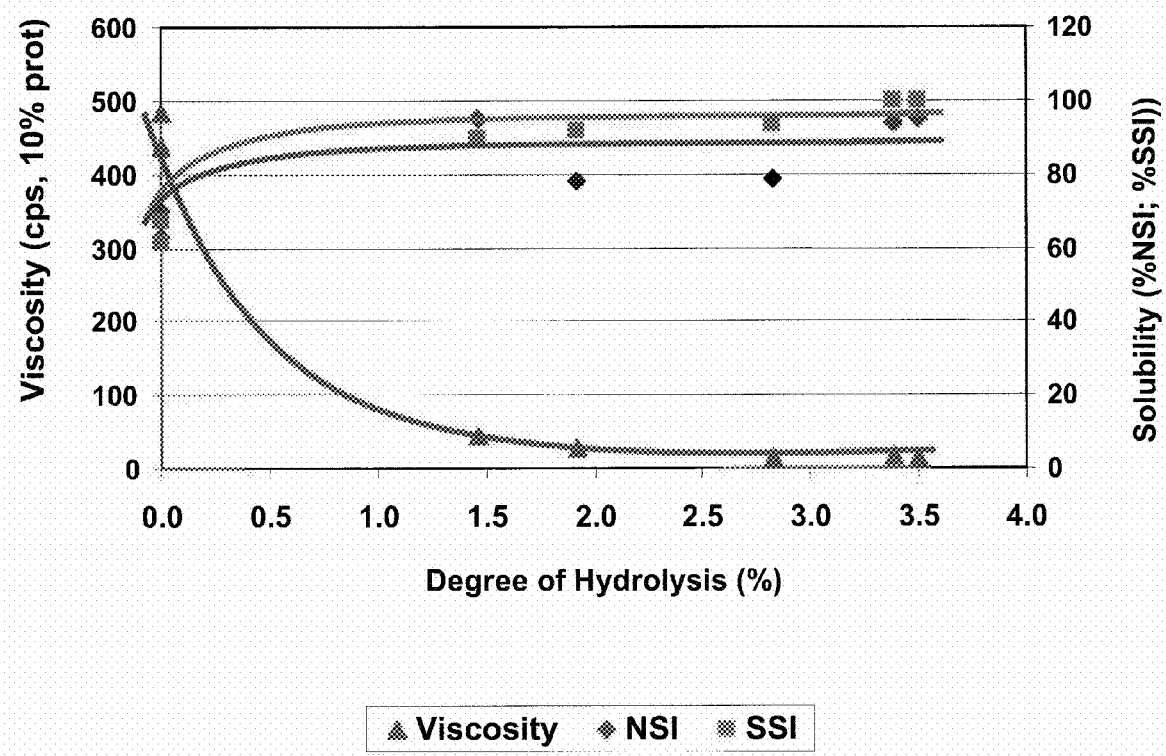
FIG. 8 presents a plot of the viscosity and solubility [i.e., soluble solids index (SSI) and nitrogen soluble index (NSI)] as a function of degree of hydrolysis of the pilot plant TL1 hydrolysates.
Figure 9:
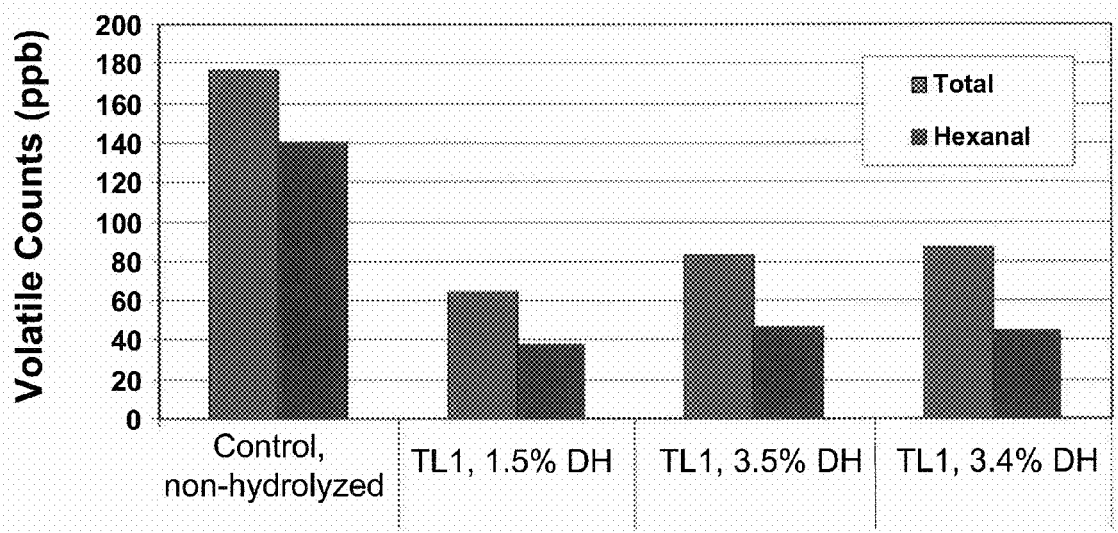
FIG. 9 illustrates that the levels of flavour volatiles are lower in the TL1 hydrolysate as compared to the control samples. (A) Presents the levels of the total active volatiles and hexanal in the control sample and TL1 hydrolysates with different degrees of hydrolysis (% DH). (B) Presents the levels of the indicated flavour volatiles in the control sample and TL1 hydrolysates with different degrees of hydrolysis (% DH).
Figure 9:
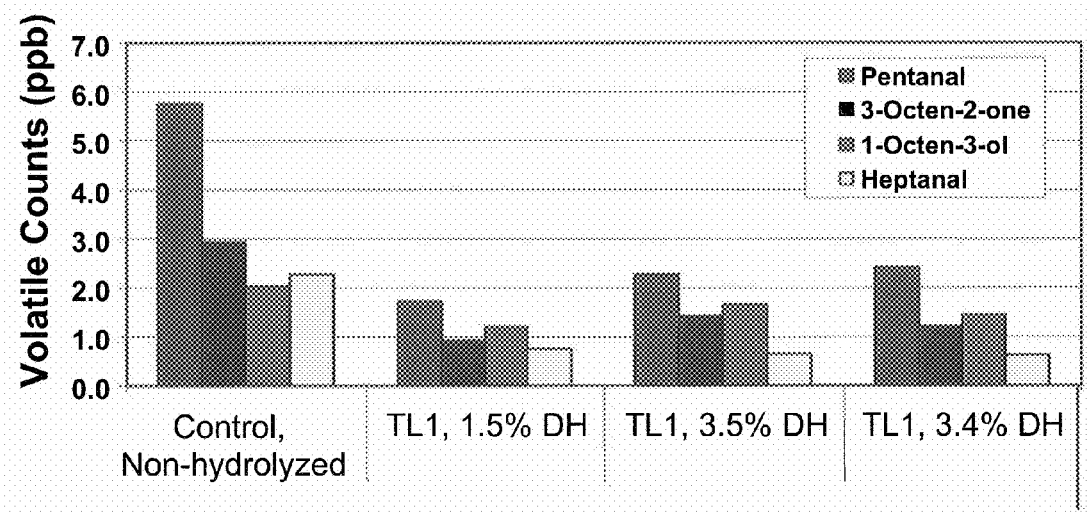
Figure 10A:
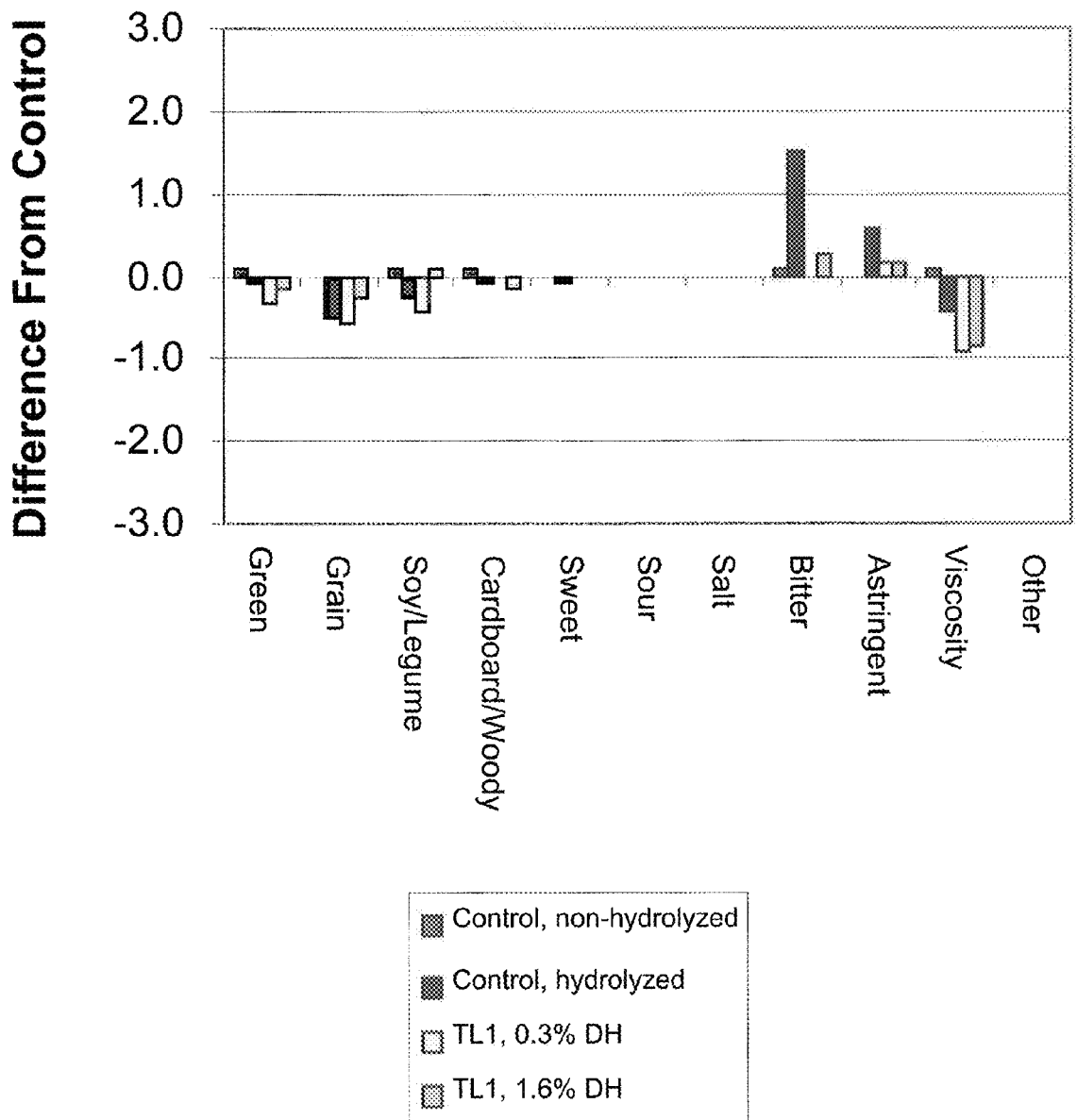
FIG. 10 presents plots of the diagnostic scores of the pilot plant TL1 hydrolysates and control samples. The control sample was non-hydrolyzed isolated soy protein. Positive scores indicate the hydrolysate had more of the sensory attribute than the control sample, and negative scores indicate the hydrolysate has less of the sensory attribute than the control sample. (A) Presents the scores for the control, 0.3% DH, and 1.6% DH samples. (B) Presents the scores for the control, 1.3% DH, and 5.2% DH samples. (C) Presents the scores for the control, 2.7% DH, and 0.9% DH samples. (D) Presents the scores for the control, 2.0% DH, and 3.8% DH samples.
Figure 10B:
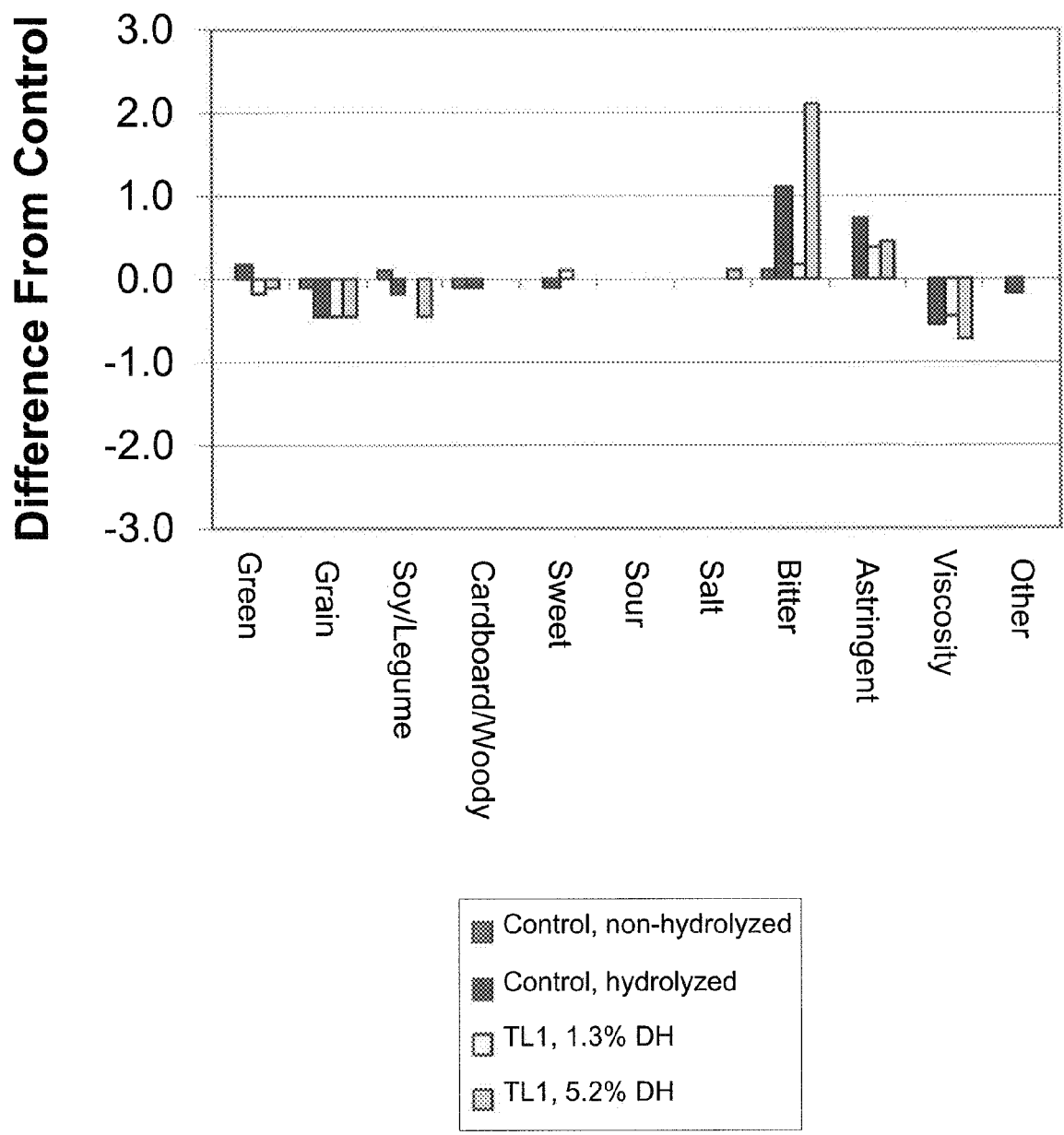
Figure 10C:
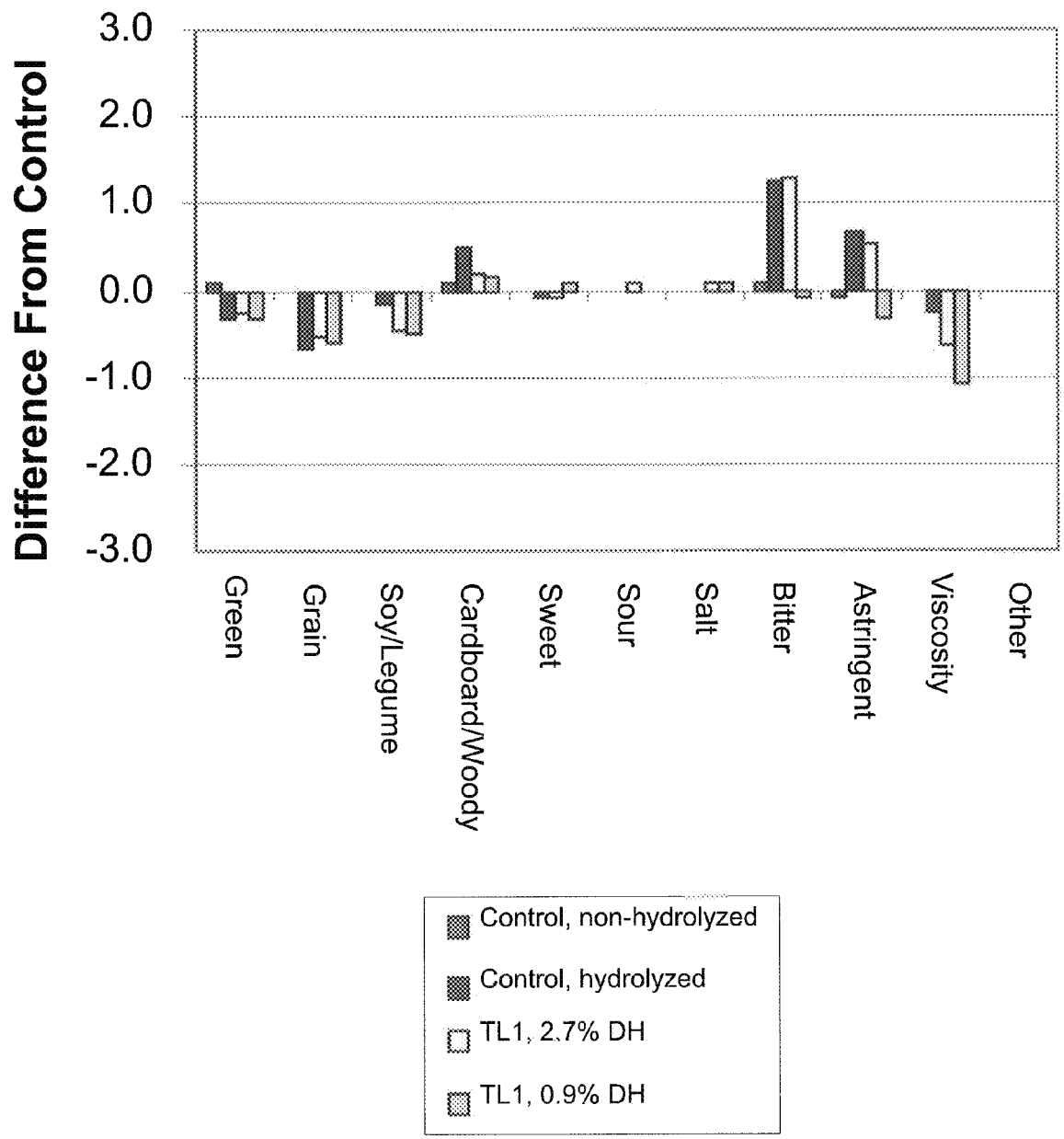
Figure 10D:
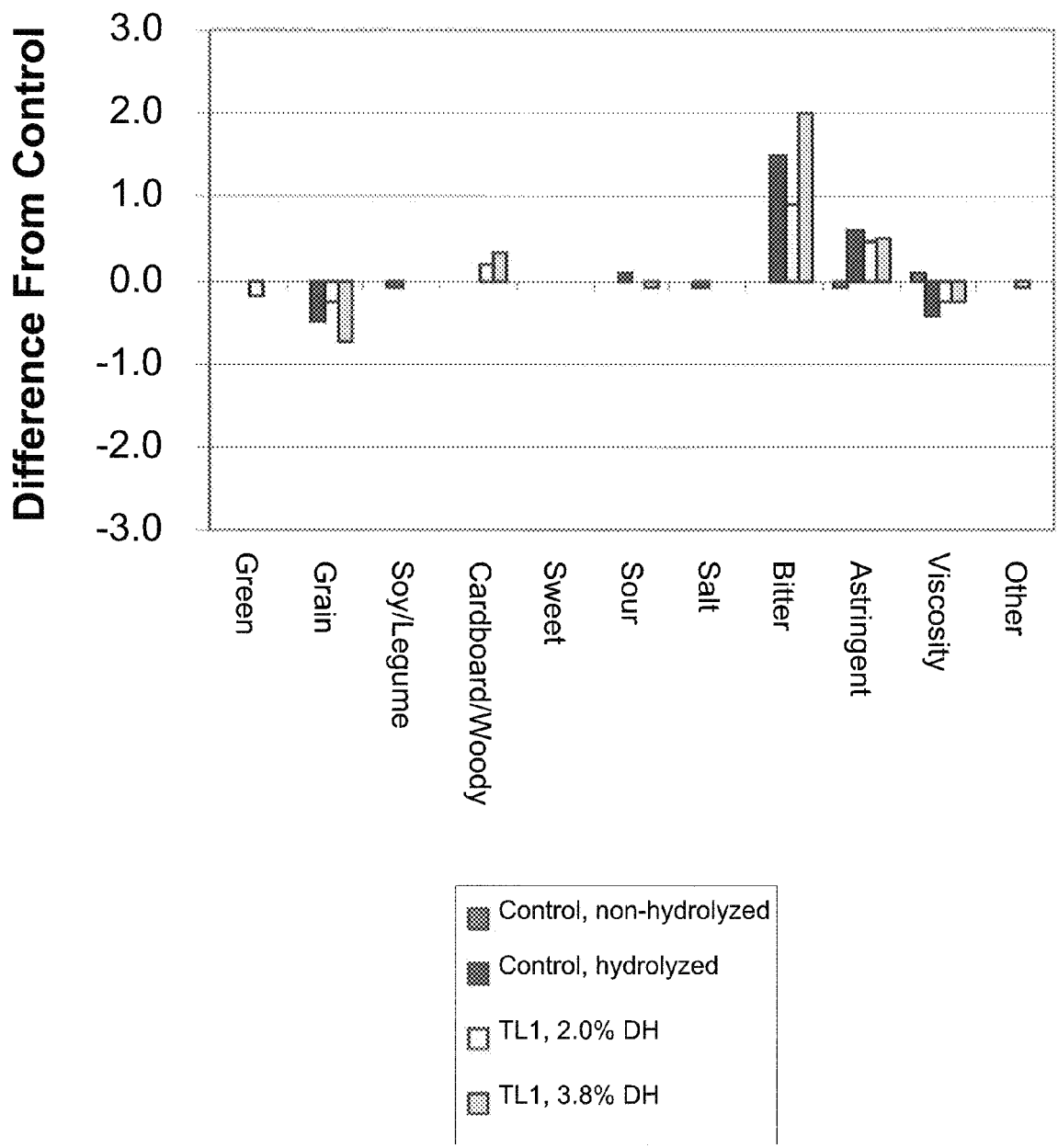

The viscosity of several of the TL1 hydrolysates and a control sample was determined at various percentages of solids (i.e., 12-20% solids). The samples were dispersed using a small Waring® (Waring Laboratory, Torrington Conn.) blender with a total slurry content of 70 grams. The samples were blended for a total of four minutes using minimal shear to decrease foam. The samples were then analyzed using a Brookfield viscometer with the small sample adapter and spindle 18 at room temperature. Each sample was prepared and analyzed in duplicate. FIG. 7 plots the viscosity measurements in centipoises (cps) for the different preparations. The commodity isolate was greater than 10,000 cps—which was too viscous for the Brookfield at 12% solids. This analysis revealed that as the degree of hydrolysis increased, the viscosity decreased, and that as the percent of solids increased, the viscosity increased. FIG. 8 summarizes the viscosity and solubility data. Solubility is expressed as soluble solids index (SSI) and nitrogen soluble index (NSI, which is the percent of water soluble nitrogen as a function of the total nitrogen). As shown in FIG. 8, viscosity decreased and solubility increased, as the degree of hydrolysis increased The amount of flavor volatiles present in several of the TL1 hydrolysates was compared to those present in the non-hydrolyzed isolated soy protein. The flavor volatiles were determined using standard GC techniques. The levels of hexanal, heptanal, pentanal, 3-octen-2-one, and 1-octen-3-ol were reduced in the TL1 hydrolysates as compared to non-hydrolyzed isolated soy protein (FIGS. 9A and 9B).

Example 12

Sensory Analysis of Pilot Plant TL1 Hydrolysates

The flavor profiles of the pilot plant TL1 hydrolysates prepared in Example 10 were analyzed using the SQS method essentially as described in Example 6. Panels of 11 or 12 trained assessors rated the hydrolysates, as compared to a control sample (i.e., non-hydrolyzed isolated soy protein). Table 12 presents the mean SQS scores and FIGS. 10A-D present plots of the diagnostic scores. In general, the TL1 hydrolysates had slightly less grain and soy/legume attributes and reduced viscosity relative to the control sample, but increased bitter attribute, especially at higher degrees of hydrolysis (% DH). The hydrolyzed control sample (i.e., sample 5-3) had slightly reduced grain attribute, but moderately increased bitter and astringent attributes. Thus, the TL1 hydrolysates were generally rated as less bitter than the hydrolyzed control sample.

TABLE 12

SQS Scores of Pilot Plant TL1 Hydrolysates.

| Sample # | Sample | SQS Score |
|---|---|---|
| 5-2 | Blind control (Non-hydrolyzed control) | 4.8 |
| 5-3 | Hydrolyzed control | 3.2 |
| 5-7 | TL1, 0.3% DH | 4.1 |
| 5-8 | TL1, 0.9% DH | 3.6 |
| 5-4 | TL1, 1.3% DH | 3.9 |
| 5-9 | TL1, 1.6% DH | 3.7 |
| 5-5 | TL1, 2.0% DH | 3.6 |
| 5-1 | TL1, 2.7% DH | 3.2 |
| 5-6 | TL1, 3.8% DH | 2.7 |
| 5-10 | TL1, 5.2% DH | 2.7 |

Figure 11:
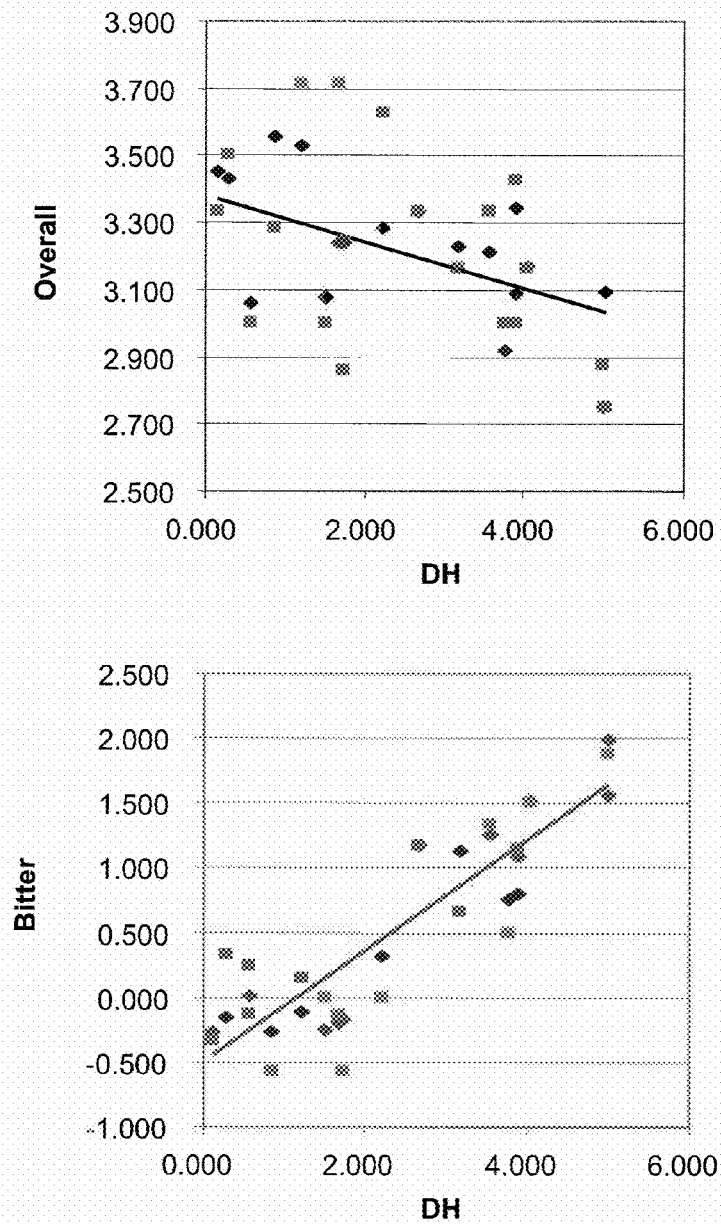
FIG. 11 presents summary plots of the sensory scores of TL1 hydrolysates as a function of degree of hydrolysis (DH). Overall liking scores are presented above and bitter scores are presented below. Diamonds represent predicted scores and squares represent real scores.

FIG. 11 presents a summary of the sensory analyses of the TL1 hydrolysates in which key sensory attributes are plotted as a function of the degree of hydrolysis. The overall sensory scores of the hydrolysate decreased as the degree of hydrolysis increased, whereas the bitter scores increased as the degree of hydrolysis increased. It appears that hydrolysates having less than about 2% DH had the best flavor with the least bitter taste.

Example 13

Analysis of Peptide Fragments in TL1 Hydrolysates of Soy

Peptides in TL1 hydrolysates of isolated soy protein having different degrees of hydrolysis were identified by LC-MS analyses using Q-STAR® XL MS (Applied Biosystems Inc. (ABI), Foster City, Calif.) and LCQ-Deca MS (ThermoFinnigan, Hertfordshire, Great Britain). Approximately (0.5-2.0 mg) of each sample was dissolved in 0.5 mL of 50 mM ammonium bicarbonate. Five µL was injected onto a 75 um i.d. column for LC-MS/MS analysis using data-dependent acquisition (LC flow rate was 180 mL/min). Nano-LC was performed with an LC Packings Ultimate nano-LC using a C18 PepMap100 column (Dionex, UK)/Eksigent 2D nano-LC using a C18 PepMap100 column (Dionex). The elution profile is presented in Table 13. Solvent A was 5% acetonitrile, 0.1% formic acid in MilliQ water, and Solvent B was 95% acetonitrile, 0.075% formic acid in MilliQ water).

TABLE 13

LC-Pump Gradient.

| Time (min) | % B |
|---|---|
| 0 | 5 |
| 3 | 5 |
| 8 | 25 |
| 40 | 60 |
| 45 | 95 |

Sample analysis proceeded with an ABI QSTAR® XL hybrid QTOF MS/MS mass spectrometer (Applied Biosystems, Foster City, Calif.) equipped with a nanoelectrospray source (Protana XYZ manipulator). Positive mode nanoelectrospray was generated from borosilicate nanoelectrospray needles at 2.5 kV. The m/z response of the instrument was calibrated daily with standards from the manufacturer. TOF mass spectra and product ion spectra were acquired using the information dependent data acquisition (IDA) feature in the Analyst QS software with the following parameters: Mass ranges for TOF MS and MS/MS were m/z 300-2000 and 70-2000, respectively. Every second, a TOF MS precursor ion spectrum was accumulated, followed by three product ion spectra, each for 3 sec. The switching from TOF MS to MS/MS was triggered by the mass range of peptides (m/z 300-2000), precursor charge state (2-4) and ion intensity (>50 counts). The DP, DP2, and FP settings were 60, 10, and 230, respectively, and rolling collision energy was used.

The peptide electrospray tandem mass spectra were processed using Analyst QS software (Applied Biosystems). Peptides were identified by searching a standard database such as NCBI or Swiss-Prot using MASCOT version 1.9 with the following constraints: no enzyme with up to one missed cleavage site; 0.8/2.0 and 0.8 Da mass tolerances for MS and MS/MS fragment ions, respectively. The charge states of precursor ions selected were 1-3.

For the LC-MS analysis using LCQ-Deca MS, samples were prepared by 1) mixing an aliquot containing 2 mg of each TL1 hydrolysate with 0.1% formic acid (1 mL) in a glass vial, vortexing for 1-2 min, and centrifuging the mixture at 13,000 rpm in a microcentrifuge for 5 min; or 2) mixing an aliquot containing 3 mg of each TL1 hydrolysate and 0.1% formic acid (300 uL) in a microcentrifuge tube and vortexing the mixture for 1-2 minutes. The entire mixture was then transferred to a precleaned C18 tip (Glygen Corp., Columbia, Md.) for peptide isolation. The C18 tip was cleaned by eluting with 0.1% formic acid in 60% acetonitrile (300 µL) and equilibrated with 0.1% formic acid (600 µL). Materials eluted with 0.1% formic acid fraction were discarded, and the peptides were eluted with 0.1% formic acid in 60% acetonitrile (600 µL). Total volume of peptide solution was reduced to 200 µL by evaporating the solvent mixture in on Genevac evaporator at 300° C. for 10 minutes. LC-MS analysis was performed essentially as described in Example 3.

Table 14 presents all of the peptides identified in the TL1 hydrolysates of soy protein.

TABLE 14

Peptides in TL1 Hydrolysates of Soy.

| SEQ ID NO: | Sequence | |
|---|---|---|
| 85 | GYLADK | 666.31 |
| 86 | FQTLFE | 783.42 |
| 24 | FETLFK | 784.39 |
| 87 | PPQESQK | 813.35 |
| 18 | PPKESQR | 841.47 |
| 51 | ADFYNPK | 854.35 |
| 88 | PQESQKR | 872.51 |
| 52 | MIIIAQGK | 873.44 |
| 89 | NQYGRIR | 906.85 |
| 7 | SPQLQNLR | 955.57 |
| 30 | PPQESQKR | 969.69 |
| 13 | LSAEFGSLR | 978.54 |
| 19 | LSAQFGSLR | 978.86 |
| 90 | PEKNPQLR | 981.95 |
| 59 | DAMDGWFR | 997.42 |
| 48 | PQNFVVAAR | 1001.67 |
| 91 | EVGQDIQSK | 1003.75 |
| 39 | FFEITPEK | 1010.52 |
| 92 | DYGSYAQGR | 1016.83 |
| 93 | PPRYEAGVK | 1017.19 |
| 31 | LNALKPDNR | 1040.48 |
| 94 | APSIYHSER | 1060.05 |
| 95 | FGVNMQIVR | 1063.52 |
| 8 | SRDPIYSNK | 1079.91 |
| 27 | LAGEKDNVVR | 1100.68 |
| 55 | YEAGVVPPGAR | 1115.81 |
| 96 | SSDFLTYGLK | 1130.55 |
| 97 | AFGVNMQIVR | 1134.48 |
| 32 | VFDGELQEGR | 1149.55 |
| 98 | NILEASYDTK | 1153.48 |
| 99 | NPIYSNNFGK | 1153.57 |
| 100 | GIGTIISSPYR | 1163.64 |
| 101 | ESYFVDAQPK | 1183.57 |
| 102 | HLSVVHPIYK | 1192.74 |
| 103 | LHENIARPSR | 1193.19 |
| 10 | SSEDEPFNLR | 1193.40 |
| 104 | NKPLVVQFQK | 1200.52 |
| 105 | AKDYGSYAQGR | 1215.94 |
| 57 | TKEVGQDIQSK | 1233.46 |
| 71 | EAFGVNMQIVR | 1263.63 |
| 106 | THHNAVTSYLK | 1270.46 |
| 107 | LAGNQEQEFLQ | 1276.11 |
| 49 | LAGNQEQEFLK | 1276.11 |
| 108 | NKNPFLFGSNR | 1293.66 |
| 67 | FLVPPQESQKR | 1328.82 |
| 34 | NFLAGEKDNVVR | 1361.77 |
| 109 | SRDPIYSNKLGK | 1378.25 |
| 36 | EQQEEQPLEVR | 1383.89 |
| 22 | PSEVLAHSYNLR | 1386.32 |
| 110 | SRNPIYSNNFGK | 1396.65 |
| 34 | ISTLNSLTLPALR | 1398.86 |
| 65 | TISSEDKPFNLR | 1406.73 |
| 68 | VLIVPQNFVVAAR | 1425.88 |
| 111 | YLAGNQEQEFLK | 1439.72 |
| 14 | SQSDNFEYVSFK | 1450.57 |
| 56 | HHLAEAAEYVGQK | 1453.52 |
| 15 | PEEVIQHTFNLK | 1454.98 |
| 112 | PEFLEHAFVVDR | 1459.51 |
| 113 | PPHSVQVHTTTHR | 1496.89 |
| 77 | NGLHLPSYSPYPR | 1500.78 |
| 114 | QIVTVEGGLSVISPK | 1526.94 |
| 25 | KTISSEDKPFNLR | 1534.93 |
| 29 | VREDENNPFYLR | 1551.92 |
| 115 | LPEEVIQHTFNLK | 1568.22 |
| 78 | AIPSEVLAHSYNLR | 1569.72 |
| 116 | FSREEGQQQGEQR | 1579.15 |
| 117 | NQRESYFVDAQPK | 1582.77 |
| 118 | LFEITPEKNPQLR | 1584.81 |
| 16 | FYLAGNQEQEFLK | 1586.53 |
| 20 | FYLAGNQEQEFLQ | 1587.53 |
| 61 | FFEITPEKNPQLR | 1618.87 |
| 35 | KQIVTVEGGLSVISPK | 1655.01 |
| 119 | QESVIVEISKEQIR | 1658.84 |
| 120 | HLAEAAEYVGQKTK | 1681.97 |
| 121 | AGRISTLNSLTLPALR | 1683.00 |

TABLE 14-continued

Peptides in TL1 Hydrolysates of Soy.

| SEQ ID NO: | Sequence | |
|---|---|---|
| 122 | FMPEKGSAEYEELR | 1685.88 |
| 123 | PFSFLVPPQESQRR | 1687.82 |
| 124 | LEASYDTKFEEINK | 1687.91 |
| 125 | LARPVLGGSSTFPYPR | 1717.87 |
| 62 | SSNSFQTLFENQNGR | 1728.71 |
| 17 | RFYLAGNQEQEFLK | 1742.88 |
| 126 | NELDKGIGTIISSPYR | 1762.75 |
| 37 | LQESVIVEISKEQIR | 1770.71 |
| 127 | THHNAVSSYIKDVFR | 1774.05 |
| 63 | QVQELAFPGSAQDVER | 1774.90 |
| 128 | THHNAVTSYLKDVFR | 1788.52 |
| 41 | LKVREDENNPFYLR | 1792.91 |
| 129 | NPFLFGSNRFETLFK | 1817.93 |
| 130 | HFLAQSFNTNEDIAEK | 1863.86 |
| 131 | NNNPFSFLVPPKESQR | 1873.99 |
| 132 | LFLLDHHDPIMPYLR | 1880.00 |
| 133 | SLSQIVQPAFESAFDLK | 1880.06 |
| 134 | DWVFTDQALPADLIKR | 1888.05 |
| 135 | NLQGENEGEDKGAIVTVK | 1900.99 |
| 136 | NILEASYDTKFEEINK | 1913.97 |
| 137 | NLQGENEEEDSGAIVTVK | 1931.88 |
| 138 | KESFFFPFELPREER | 1957.03 |
| 69 | RPSYTNGPQEIYIQQGK | 1980.03 |
| 139 | SSNSFQTLFENQNGRIR | 1997.89 |
| 140 | NNNPFSFLVPPQESQRR | 2029.84 |
| 141 | AIPSEVLSNSYNLGQSQVR | 2061.96 |
| 142 | HFLAQSFNTNEDTAEKLR | 2121.87 |
| 143 | QVQELAFPGSAQDVERLLK | 2129.03 |
| 144 | VPSGTTYYVVNPDNNENLR | 2152.00 |
| 145 | IPAGTTYYLVNPHDHQNLK | 2181.01 |
| 146 | QEEENEGSNILSGFAPEFLK | 2239.48 |
| 147 | KQGQHQQQEEEGGSVLSGFSK | 2288.13 |
| 148 | NLQGENEEEDSGAIVTVKGGLR | 2314.87 |
| 149 | SVSQNVLPLLQSAFDLNFTPR | 2346.32 |
| 150 | QVKNNNPFSFLVPPQESQRR | 2384.93 |
| 74 | VFDGELQEGGVLIVPQNFAVAAK | 2402.06 |
| 80 | KQGQHQQEEEEGGSVLSGFSK | 2418.85 |
| 151 | QVKNNNPFSFLVPPQESQRRA | 2457.12 |
| 152 | NAMFVPHYTLNANSIIYALNGR | 2480.21 |
| 153 | TPVVAVSIIDTNSLENQLDQMPR | 2541.23 |
| 75 | GKQQEEENEGSNILSGFAPEFLK | 2552.16 |
| 154 | VFDGELOEGRVLIVPQNFVVAAR | 2557.16 |
| 155 | EPVVAISLLDTSNFNNQLDQTPR | 2572.90 |
| 156 | KNAMFVPHYTLNANSIIYALNGR | 2608.37 |
| 157 | DLDIFLSIVDMNEGALLLPHFNSK | 2701.56 |
| 158 | VFYLAGNPDIEHPETMQQQQQQK | 2730.40 |
| 159 | HFLAQSFNTNEDIAEKLQSPDDER | 2804.41 |
| 160 | LVFCPQQAEDDKCGDIGISIDHDDGTR | 2946.31 |
| 161 | SQQARQVKNNNPFSFLVPPQESQRR | 2956.36 |
| 162 | VLFGEEEEQRQQEGVIVELSKEQIR | 2973.47 |
| 163 | NLQGENEEEDSGAIVTVKGGLRVTAPAMR | 3041.33 |
| 79 | WQEQQDEDEDEDEDDEDEQIPSHPPR | 3211.13 |
| 164 | VFYLAGNPDIEYPETMQQQQQQKSHGGR | 3249.31 |
| 165 | DFVLDNEGNPLENGGTYYILSDITAFGGIR | 3261.53 |
| 166 | HQQEEENEGGSILSGFTLEFLEHAFSVDK | 3278.49 |
| 167 | RQQEEENEGGSILSGFAPEFLEHAFVVDR | 3291.54 |
| 168 | TNDTPMIGTLAGANSLLNALPEEVIQHTFNLK | 3423.41 |
| 169 | HNIGQTSSPDIYNPQAGSVTTATSLDFPALSWLR | 3646.60 |
| 170 | HQQEEENEGGSILSGFTLEFLEHAFSVDKQIAK | 3717.92 |
| 171 | NFLAGSQDNVISQIPSQVQELAFPGSAQAVEKLLK | 3728.18 |
| 172 | MITLAIPVNKPGRFESFFLSSTQAQQSYLQGFSK | 3822.18 |
| 173 | FREGDLIAVPTGVAWWMYNNEDTPVVAVSIIDTNSLENQLDQMPR | 5105.43 |
| 270 | LSAEFGSLRK | 1107.69 |
| 271 | IGENKDAMDGWFR | 1538.75 |
| 40 | VLFSREEGQQQGEQR | 1791.01 |
| 177 | NAMFVPHYNLNANSIIYALNGR | 2493.17 |
| 272 | KNAMFVPHYNLNANSIIYALNGR | 2621.46 |
| 273 | TNDRPSIGNLAGANSLLNALPEEVIQHTFNLK | 3446.52 |
| 274 | TNDRPSIGNLAGANSLLNALPEEVIQQTFNLR | 3466.74 |

Example 14

Hydrolysis of Soy Protein with Other Endopeptidases

Isolated soy protein was treated with different endopeptidases (e.g., SP3, trypsin-like protease from *Fusarium* solani (TL5; SEQ ID NO:2), trypsin-like protease from *Fusarium* cf. solani (TL6; SEQ ID NO:3), porcine trypsin, or bovine trypsin) to determine whether trypsin or a trypsin-like protease from another source could be used to hydrolyze soy protein.

An 8% slurry of isolated soy protein (i.e., SUPRO® 500E) was prepared, adjusted to pH 8, and mixed with one of the endopeptidases for a final concentration of 100 mg protease/kg soy protein. A non-protease containing control samples was included. The slurries were incubated in a water bath at 50° C. for 2 hours with mixing, and then the proteases were heat-inactivated (80° C. for 30 min). Deionized water was added to each sample for a final concentration of 5% soy protein.

Figure 12:
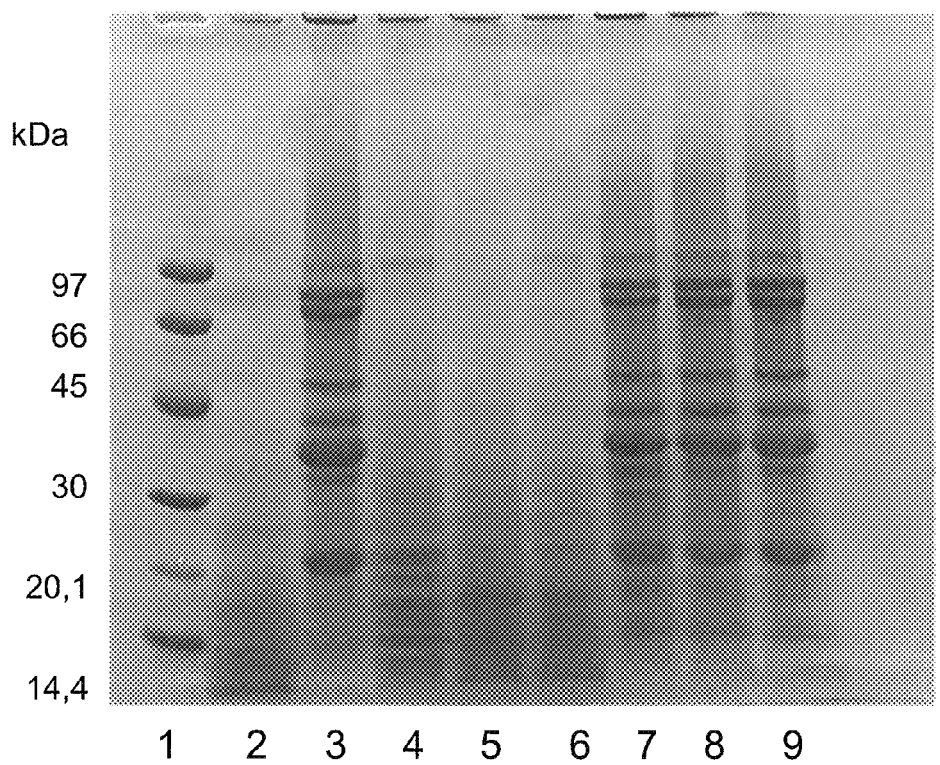
FIG. 12 illustrates the hydrolysis of isolated soy protein with several different trypsin-like proteases. Presented is an image of a Coomassie-stained SDS polyacrylamide gel in which non-hydrolyzed soy protein and enzyme-treated soy protein samples were resolved. Lane 1 contains molecular weight markers with the sizes indicated to the left of the gel. Lanes 3 and 9 contain untreated isolated soy protein. Lane 2 and lanes 4-8 contain soy treated with TL1, SP3, TL5, TL6, porcine trypsin, and bovine trypsin, respectively.

To estimate the degree of hydrolysis, an aliquot of each sample was resolved by SDS-PAGE on a 4-20% Tris-Glycine gel (Novex Inc., Wadsworth, Ohio). As shown in FIG. 12, TL1, SP3, TL5, and TL6 hydrolyzed the soy protein into smaller polypeptide fragments, whereas there was little or no hydrolysis of the soy protein after treatment with either porcine trypsin or bovine trypsin (see lanes 7 and 8). The inability of porcine and bovine trypsins to cleave soy proteins was observed at both 37° C. and 50° C. (at pH 8).

Example 15

Inhibition of Trypsin-Like Proteases with Bowman-Birk Inhibitor

It is possible that the porcine and bovine trypsins were unable to hydrolyze the soy protein material because soy contains active protease inhibitors that survived heat treatment during the production of the soy material. To test this hypothesis, the proteases were incubated with various concentrations of a commercial preparation of the Bowman-Birk inhibitor and residual enzyme activity was measured.

The proteases were diluted to 0.001 mg/ml with assay buffer (0.1 M Tris, 0.02% Brij 35, pH 8.0) and mixed with various concentration of Bowman-Birk inhibitor (Cat # T-9777, Sigma-Aldrich) in wells of a microtiter plate. The plate was incubated 1 hour at room temperature with agitation. Residual activity was measured by adding 0.6 mg/ml of substrate, Boc-Val-Leu-Gly-Arg-p-nitroanilide (L-1205; Bachem Biosciences, Prussia, Pa.). Absorbance was measured at 405 nm every 10 seconds for 3 min at room temperature. Activity was calculated from the initial slope of the measured absorbance at 405 nm. Residual activity was calculated as the activity in a well with the inhibitor relative to the activity in a well without the inhibitor.

As shown in Table 15, porcine and bovine trypsins were inhibited by lower concentrations of Bowman-Birk inhibitor than the microbial proteases. Thus, it appears that soy materials contain compounds that inhibit the activity of animal-derived trypsins.

TABLE 15

Inhibition of Animal-Derived Proteases

| Bowman-Birk inhibitor (mg/ml) | Protease (% residual activity) | | | | |
|---|---|---|---|---|---|
| | TL1 | TL5 | TL6 | Porcine trypsin | Bovine trypsin |
| 0.5 | 0.8 | 0.5 | 1.3 | 0.1 | 0.0 |
| 0.25 | 2.2 | 1.2 | 2.9 | 0.1 | 0.0 |
| 0.125 | 5.8 | 3.1 | 9.5 | 0.2 | 0.0 |
| 0.0625 | 13 | 7.2 | 26 | 0.4 | 0.0 |
| 0.0313 | 32 | 19 | 55 | 1.0 | 0.1 |

TABLE 15-continued

Inhibition of Animal-Derived Proteases

| Bowman-Birk inhibitor (mg/ml) | Protease (% residual activity) | | | | |
|---|---|---|---|---|---|
| | TL1 | TL5 | TL6 | Porcine trypsin | Bovine trypsin |
| 0.0156 | 61 | 29 | 66 | 2.2 | −1.5 |
| 0.0078 | 82 | 43 | 84 | 3.2 | 0.0 |
| 0.0039 | 109 | 55 | 97 | 6.2 | −0.4 |
| 0.00195 | 103 | 57 | 94 | 8.3 | 0.1 |
| 0.00097 | 111 | 71 | 107 | 9.4 | 5.3 |
| 0.00048 | 117 | 78 | 104 | 11 | 0.9 |
| 0 | 100 | 100 | 100 | 100 | 100.0 |

Example 16

Trypsin Ratio and Identification of Trypsin-Like Proteases

An assay was developed for identifying enzymes having trypsin-like activity. For this, trypsin-like activity was measured using chromogenic substrates with the general formula Suc-Ala-Ala-Pro-Xxx-pNA (Bachem Biosciences, King of Prussia, Pa.), where Xxx is the three letter abbreviation for one of the twenty natural amino acid residues and pNA is para-nitroanilide. If the endopeptidase cleaved the peptide bond on the carboxyl terminal side of Xxx, then para-nitroaniline was released and a yellow color was generated and measured essentially as described in Example 15. Ten pNA substrates were used, wherein Xxx was Ala, Arg, Asp, Glu, 11e, Leu, Lys, Met, Phe or Val.

The following endopeptidases were tested: ALCALASE®, SP3, TL1, and porcine trypsin. All enzymes were purified by chromatography to a high purity, i.e., only one band was seen for each peptidase on Coomassie stained SDS-polyacrylamide gels. The activity of each enzyme was measured at a pH value where the activity was at least half of that of the pH optimum with the Suc-Ala-Ala-Pro-Xxx-pNA substrates. The pH optimum of ALC was pH 9, and the pH optimum of the other three peptidases was pH 10 with respect to these substrates. The assay buffer was 100 mM succinic acid, 100 mM HEPES, 100 mM CHES, 100 mM CABS, 1 mM $CaCl_2$, 150 mM KCl, and 0.01% Triton X-100, pH 9.0. Twenty µL of each peptidase dilution (diluted in 0.01% Triton X-100) was placed in ten wells of a microtiter plate. The assay was started by adding 200 µL of one of the ten pNA substrates to each well (50 mg dissolved in 1.0 ml DMSO and further diluted 90× with the assay buffer). The initial increase in $OD_{405}$ was monitored as a measure of the peptidase activity. If a linear plot was not achieved in the 4 minutes measuring time, the peptidase was diluted further and the assay was repeated.

The Trypsin ratio was calculated as the maximal activity with either substrate containing Arg or Lys, divided by the maximal activity with any of the eight other substrates. A trypsin-like endopeptidase was defined as an endopeptidase having a Trypsin ratio of more than 100.

The activity levels are presented in Table 16 as activities relative to the activity for the Suc-Ala-Ala-Pro-Xxx-pNA substrate with the highest activity, as well as the Trypsin ratios. Although the assay was performed at pH 9 and three of the tested peptidases have pH optimums greater than pH 9, the activity of these three peptidases at pH 9 was more than half of the activity at the pH optimum. Thus, this analysis revealed the *Achromobacter lyticus* protease (SP3), the *Fusarium* trypsin-like protease (TL1) and porcine trypsin are trypsin-like endopeptidases, whereas ALCALASE® (ALC) is not a trypsin-like endopeptidase.

TABLE 16

Activities and Trypsin Ratios of Various Peptidases.

| Substrate (Xxx) | ALC | SP3 | TL1 | Porcine Trypsin |
|---|---|---|---|---|
| Ala | 0.02497 | 0.00001 | 0.00000 | 0.00001 |
| Arg | 0.01182 | 0.00001 | 1.00000 | 1.00000 |
| Asp | 0.00053 | 0.00000 | 0.00000 | 0.00000 |
| Ile | 0.00026 | 0.00000 | 0.00000 | 0.00000 |
| Met | 0.37582 | 0.00023 | 0.00002 | 0.00031 |
| Val | 0.00033 | 0.00000 | 0.00000 | 0.00000 |
| Leu | 0.86502 | 0.00001 | 0.00000 | 0.00002 |
| Glu | 0.00289 | 0.00000 | 0.00000 | 0.00000 |
| Lys | 0.01900 | 1.00000 | 0.53071 | 0.51396 |
| Phe | 1.00000 | 0.00001 | 0.00003 | 0.00057 |
| Max of Arg or Lys | 0.01900 | 1.00000 | 1.00000 | 1.00000 |
| Max of non-Arg/Lys | 1.00000 | 0.00023 | 0.00003 | 0.00057 |
| Trypsin ratio | 0.019 | 4300 | 33000 | 1750 |

Example 17

TL1 Hydrolysates Derived From a Combination of Soy and Dairy Proteins

A combination of isolated soy protein and isolated dairy protein was hydrolyzed with TL1 to different degrees of hydrolysis, so that the functional properties and sensory attributes of the combination could be assessed.

A 5% slurry of soy and dairy proteins was made by dispersing a 50/50 mix of isolated soy protein (SUPRO® 500E) and sodium caseinate (Alanate® 180, NZMP Inc., Wellington, New Zealand) in water with moderate mixing. The mixture was heated to 80° C. and held for five minutes, cooled to 50° C., and the pH was adjusted to 8.0 using 1 M NaOH. Aliquots of the slurry were heated to 50° C. with medium mixing, and varying amounts of TL1 (~17-600 mg of enzyme protein per kg of intact protein) were added to achieve targeted % DH values of 0, 2% DH, 4% DH, and 6% DH. After incubating at 50° C. for a period of time (about 60 min) to generate the desired degree of hydrolysis, the samples were heated to 90° C. for 3 min to inactivate the enzymes. The samples were chilled on ice and stored at 4° C. The degree of hydrolysis (% DH) was determined using the TNBS method (as described in Example 1).

Figure 13:
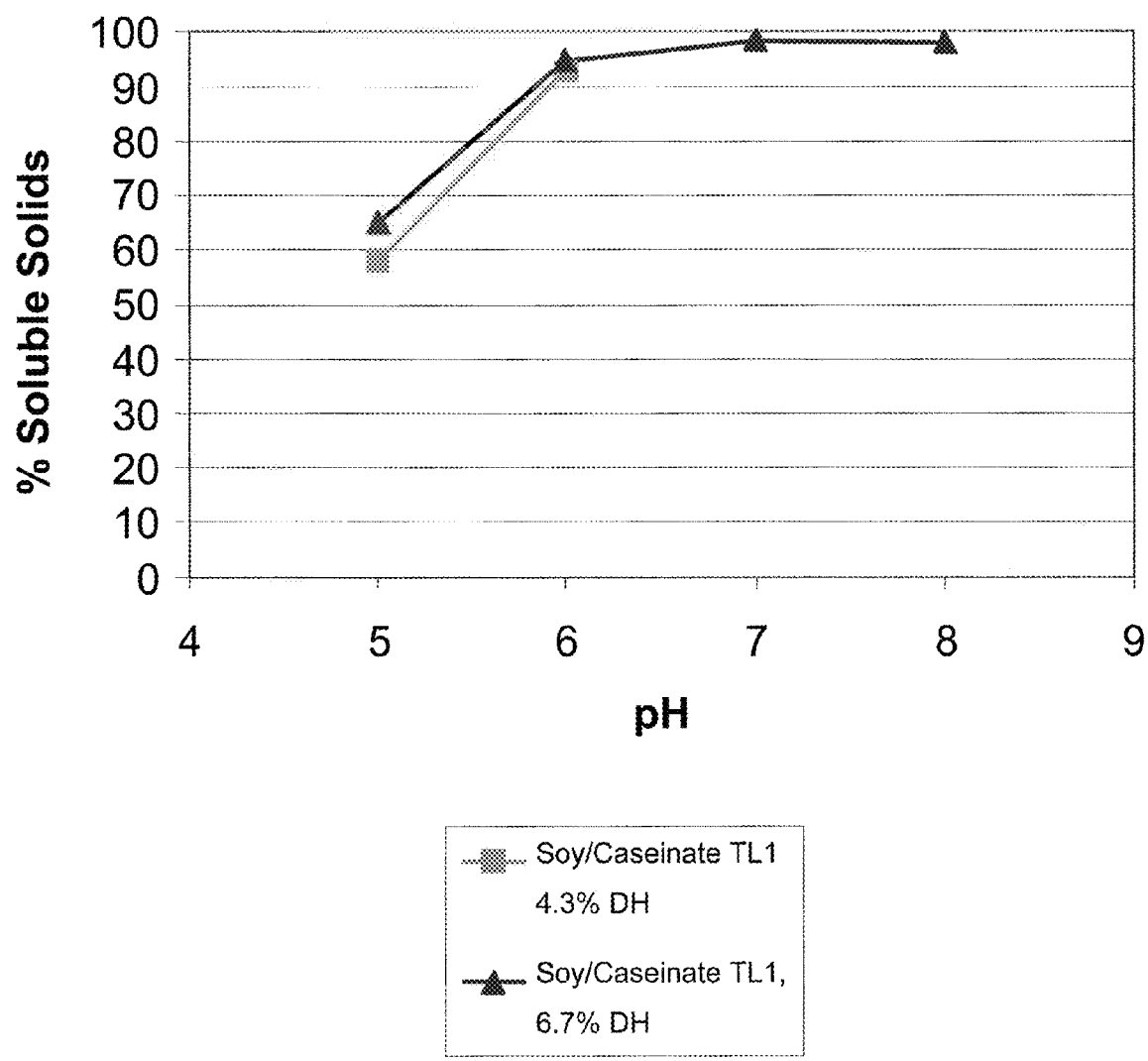
FIG. 13 illustrates the solubility of TL1 hydrolysates of a combination of soy and dairy proteins as a function of pH.

The effect of pH on solubility was tested in two of the soy/dairy TL1 hydrolysates (i.e., 4.3% DH and 6.7% DH). Aliquots of each were adjusted to pH 5, pH 6, pH 7, or pH 8, and the samples were centrifuged at 500×g for 10 minutes. The amount of solid matter in solution before centrifuging was compared to the amount of solid matter in solution after centrifuging to give the soluble solids index (SSI), and a plot of the % soluble solids as a function of pH is presented in FIG. 13. Both solutions had reduced solubility at pH levels of about pH 5 (i.e., around the isoelectric point of soy protein). Both of the soy/dairy TL1 hydrolysates, however, had excellent solubility at levels of about pH 6.0 and above.

Example 18

Analysis of Peptide Fragments in TL1 Hydrolysates of Soy/Dairy

Peptide fragments in the soy/dairy TL1 hydrolysates prepared in Example 17 were identified by liquid chromatography mass spectrometry (LC-MS), using methods detailed above (see Examples 3, 4, and 13). The sequences of the peptide fragments identified in this study are listed in Table 17. Four new soy derived peptides were identified (i.e., SEQ ID NOs:174, 175, 176, and 177). The dairy derived sequences are SEQ ID NOs:178-197.

TABLE 17

Peptide Fragments* in TL1 Hydrolysates of Soy/Dairy.

| SEQ ID NO: | Sequence | MH+ |
|---|---|---|
| 13 | LSAEFGSLR | 979.45 |
| 96 | SSDFLTYGLK | 1130.50 |
| 174 | EAFGVNMQIVR | 1263.55 |
| 34 | ISTLNSLTLPALR | 1398.83 |
| 175 | ISPLPVLKEIFR | 1411.76 |
| 68 | VLIVPQNFVVAAR | 1425.67 |
| 14 | SQSDNFEYVSFK | 1450.50 |
| 56 | HHLAEAAEYVGQK | 1452.65 |
| 78 | AIPSEVLAHSYNLR | 1569.65 |
| 16 | FYLAGNQEQEFLK | 1586.65 |
| 61 | FFEITPEKNPQLR | 1618.66 |
| 121 | AGRISTLNSLTLPALR | 1682.88 |
| 176 | YEAGVVPPARFEAPR | 1658.76 |
| 37 | LQESVIVEISKEQIR | 1770.84 |
| 72 | NNNPFSFLVPPQESQR | 1873.80 |
| 69 | RPSYTNGPQEIYIQQGK | 1978.84 |
| 140 | NNNPFSFLVPPQESQRR | 2029.93 |
| 149 | SVSQNVLPLLQSAFDLNFTPR | 2346.00 |
| 152 | NAMFVPHYTLNANSIIYALNGR | 2479.02 |
| 177 | NAMFVPHYNLNANSIIYALNGR | 2492.02 |
| 156 | KNAMFVPHYTLNANSIIYALNGR | 2607.38 |
| 178 | YIPIQYVLSR | 1251.58 |
| 179 | YLGYLEQLLR | 1268.39 |
| 180 | HIQKEDVPSER | 1337.60 |
| 181 | FFVAPFPEVFGK | 1384.76 |
| 182 | FVAPFPEVFGKEK | 1494.68 |
| 183 | HPHLSFMAIPPKK | 1502.71 |
| 184 | YLGYLEQLLRLK | 1509.39 |
| 185 | IAKYIPIQYVLSR | 1563.77 |
| 186 | HPHPHLSFMAIPPK | 1608.72 |
| 187 | FFVAPFPEVFGKEK | 1642.29 |
| 188 | HPHPHLSFMAIPPKK | 1736.78 |
| 189 | HQGLPQEVLNENLLR | 1759.80 |

TABLE 17-continued

Peptide Fragments* in TL1 Hydrolysates of Soy/Dairy.

| SEQ ID NO: | Sequence | MH+ |
|---|---|---|
| 190 | SPAQILQWQVLSNTVPAK | 1979.96 |
| 191 | HPHPHLSFMAIPPKKNQDK | 2222.18 |
| 192 | HPIKHQGLPQEVLNENLLR | 2235.07 |
| 193 | RPKHPIKHQGLPQEVLNENLLR | 2616.33 |
| 194 | YYQQKPVALINNQFLPYPYYAKPAAVR | 3216.39 |
| 195 | LHSMKEGIHAQQKEPMIGVNQELAYFYPELFR | 3804.52 |
| 196 | LITLAIPVNKPGRFESFFLSSTEAQQSYLQGFSR | 3832.67 |
| 197 | YPSYGLNYYQQKPVALINNQFLPYPYYAKPAAVR | 4010.66 |

*Dairy-derived peptide fragments = SEQ ID NOs: 178-197; Soy-derived peptide fragments = all other SEQ ID NOs.

Example 19

TL1 Hydrolysates Derived From Other Protein Materials

A variety of other plant-derived protein materials were treated with TL1 to generate additional hydrolysates. These hydrolysates were produced at a small scale (i.e., bench top). For this, 5% slurries of either canola protein isolate, wheat gluten, or corn germ proteins were denatured at a temperature above 80° C. for five minutes. The protein slurries were neutralized to about pH 8.0-8.5 with an aqueous alkaline solution or an aqueous alkaline earth solution, such as a sodium hydroxide solution or a potassium hydroxide solution. Each of the protein slurries was then treated with TL1 enzyme at a temperature and for a time sufficient to hydrolyze the protein material. The TL1 enzyme was added to the protein slurries at a concentration of from 0.01% to 0.08% enzyme protein based on the protein curd weight basis. The enzyme was contacted with the protein curd material at a temperature of about 50° C. for a period of from 50 minutes to 70 minutes, to hydrolyze the protein. The hydrolysis reaction was terminated by heating the hydrolyzed soy protein material to a temperature that effectively inactivated the enzyme.

Table 18 presents the reaction parameters for a typical set of hydrolysates. The activity of TL1 enzyme was measured based on % DH which is measured by determining moles $NH_2$ present per 100 kg protein. The increased TNBS values demonstrate the enzyme activity. Enzyme activity appeared to be affected by the suspension or solubility of the protein material, although the activities are not optimized for each protein.

TABLE 18

| Reaction Parameters. | | | | |
|---|---|---|---|---|
| Sample | pH, Temperature | Time (min) | Dose (mg enzyme protein/kg solids) | TNBS Value (moles $NH_2$ per 100 kg protein)* |
| Canola D | 8.0, 50° C. | 60 | 400 | 38.8 |
| Canola E | 8.0, 50° C. | 60 | 800 | 46.1 |
| Corn Germ B | 8.0, 50° C. | 60 | 100 | 41.0 |
| Corn Germ D | 8.0, 50° C. | 60 | 400 | 48.9 |
| Corn Germ E | 8.0, 50° C. | 60 | 800 | 57.2 |
| Wheat E | 8.0, 50° C. | 60 | 800 | 20.8 |

*TNBS value = TNBS value of test sample − TNBS value of control sample (i.e., non-hydrolyzed protein)

Figure 14:
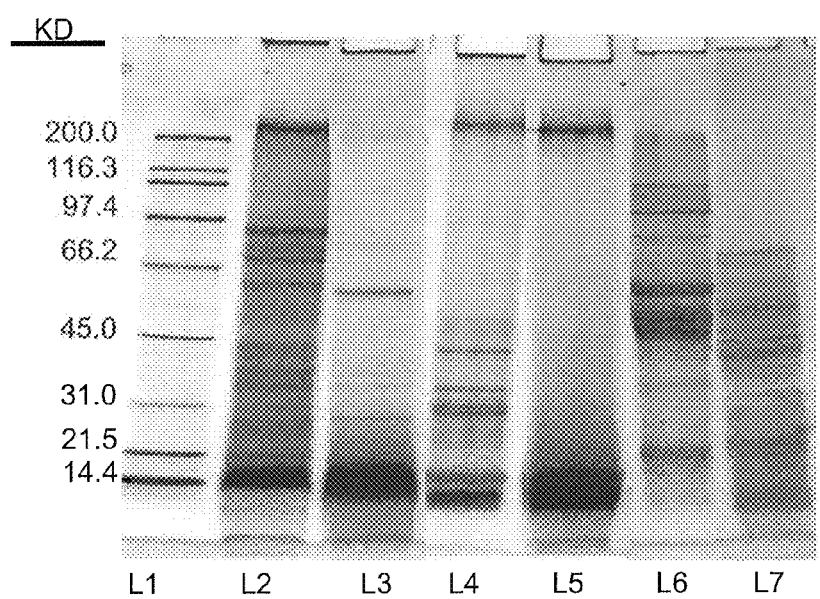
FIG. 14 illustrates the hydrolysis of other plant protein materials by TL1. Presented is an image of a Coomassie-stained SDS-polyacrylamide gel in which untreated and treated protein samples were resolved. Lane 1 (L1) contains molecular weight markers (as indicated in kDa to the left of the gel). Lane 2 (L2), lane 4 (L4), and lane 6 (L6) contain samples of unhydrolyzed corn germ, canola and wheat germ, respectively. Lane 3 (L3), lane 5 (L5), and lane 7 (L7) contain TL1 hydrolysates of corn germ, canola, and wheat germ, respectively.

The TL1 canola, corn, or wheat hydrolysates and non-hydrolyzed control samples were analyzed by SDS PAGE using standard procedures. FIG. 14 presents an image of the gel. This analysis revealed that all of the major protein subunits of each protein material were cleaved by TL1.

The representative peptides in the canola, corn, or wheat TL1 hydrolysates were identified using procedures detailed above. Table 19, 20, and 21 present representative peptides identified in the TL1 hydrolysates of canola, corn, and wheat, respectively.

TABLE 19

Peptides in TL1 Hydrolysates of Canola Protein Isolate.

| SEQ ID NO: | Peptide | MH+ |
|---|---|---|
| 198 | QTATHLPR | 923.43 |
| 199 | LQNQQVNR | 999.47 |
| 200 | YQTATHLPR | 1086.48 |
| 201 | GPFQVVRPPL | 1109.57 |
| 202 | MADAVGYAGQK | 1110.45 |
| 203 | EFQQAQHLR | 1156.51 |
| 204 | NNFEWISFK | 1184.51 |
| 205 | GASKAVKQQIR | 1185.56 |
| 206 | VQGQFGVIRPP | 1197.60 |
| 207 | IYQTATHLPR | 1199.50 |
| 208 | MADAVGYAGQKGK | 1295.50 |
| 209 | VQGPFSVIRPPL | 1309.70 |
| 210 | VQGQFGVIRPPL | 1310.68 |
| 211 | GLYLPSFFSTAK | 1330.64 |
| 212 | TNANAQINTLAGR | 1343.61 |
| 213 | ISYVVQGMGISGR | 1366.63 |
| 214 | NILNGFTPEVLAK | 1415.71 |
| 215 | TAQQLQNQQDNR | 1443.61 |
| 216 | RMADAVGYAGQKGK | 1451.62 |
| 217 | ATSQQFQWIEFK | 1512.63 |
| 218 | AGNNPQGQQWLQGR | 1553.66 |
| 219 | GQLLVVPQGFAVVKR | 1610.88 |

TABLE 19-continued

Peptides in TL1 Hydrolysates of Canola Protein Isolate.

| SEQ ID NO: | Peptide | MH+ |
|---|---|---|
| 220 | TLLFGEKPVTVFGIR | 1676.86 |
| 221 | LLAGNNPQGQQWLQGR | 1779.82 |
| 222 | VTSVNSYTLPILQYIR | 1866.93 |
| 223 | MNQFFHGWYMEPLTK | 1928.79 |
| 224 | TAQQLQNQQDNRGNIVR | 1982.91 |
| 225 | PFLLAGNNPQGQQWLQGR | 2023.94 |
| 226 | FGIVEGLMTTVHSITATQK | 2032.96 |
| 227 | GLPLEVISNGYQISPQEAR | 2070.99 |
| 228 | WFLPFDESDPASIEAAER | 2079.83 |
| 229 | GLPLEVISNGYQISLEEAR | 2088.00 |
| 230 | ALPLEVITNAFQISLEEAR | 2114.49 |
| 231 | QQGQQQGQQGQQLQHEISR | 2205.89 |
| 232 | NFGKDFIFGVASSAYQIEGGR | 2262.97 |
| 233 | ALPLEVITNAFQISLEEARR | 2270.49 |
| 234 | THENIDDPARADVYKPNLGR | 2281.00 |
| 235 | FNTIETTLTHSSGPASYGRPR | 2291.97 |
| 236 | NLRPFLLAGNNPQGQQWLQGR | 2406.69 |
| 237 | VFDQEISKGQLLVVPQGFAVVKR | 2557.27 |

TABLE 20

Peptides in TL1 Hydrolysates of Corn (Maize).

| SEQ ID NO: | Peptide | MH+ |
|---|---|---|
| 238 | VAVLEANPR | 968.60 |
| 239 | RPYVFDRR | 1108.69 |
| 240 | HGQDKGIIVR | 1122.74 |
| 241 | AIGFDGLGDPGR | 1174.69 |
| 242 | VLRPFDEVSR | 1217.76 |
| 243 | NPESFLSSFSK | 1242.68 |
| 244 | VFLAGADNVLQK | 1274.80 |
| 245 | DIGFNGLADPNR | 1288.75 |
| 246 | NALENYAYNMR | 1358.73 |
| 247 | VPTVDVSVVDLTVR | 1498.34 |
| 248 | QISWNYNYGPAGR | 1525.83 |
| 249 | ARFEELNMDLFR | 1540.98 |
| 250 | REQLGQQGYSEMGK | 1610.84 |
| 251 | TLLFGDKPVTVFGIR | 1663.11 |
| 252 | REQLGQQGYSEMGKK | 1739.04 |
| 253 | GPLQISWNYNYGPAGR | 1793.05 |
| 254 | ALSFASKAEEVDEVLGSR | 1908.10 |
| 255 | AVGKVLPDLNGKLTGMSFR | 2003.30 |
| 256 | ALSFASKAEEVDEVLGSRR | 2064.30 |
| 257 | LSPGTAFVVPAGHPFVAVASR | 2080.53 |
| 258 | DQRPSIANQHGQLYEADAR | 2169.30 |
| 259 | ARLSPGTAFVVPAGHPFVAVASR | 2307.41 |
| 260 | RHASEGGHGPHWPLPPFGESR | 2308.34 |
| 261 | YYGRGPLQISWNYNYGPAGR | 2332.25 |

TABLE 21

Peptides in TL1 Hydrolysates of Wheat.

| SEQ ID NO: | Peptide | MH+ |
|---|---|---|
| 262 | WSTGLQMR | 978.53 |
| 263 | QVVDQQLAGR | 1113.62 |
| 264 | QYEQTVVPPK | 1188.70 |
| 265 | QGQQGYYPTSPQHTGQR | 1933.07 |
| 266 | QVVDQQLAGRLPWSTGLQMR | 2283.30 |
| 267 | QGYDSPYHVSAEQQAASPMVAK | 2364.25 |
| 268 | SLQQPGQGQQIGQGQQGYYPTSPQHTGQR | 3154.78 |
| 269 | QGYYPTSLQQPGQGQQIGQGQQGYYPTSPQHTGQR | 3864.02 |

Example 20

Sensory Analysis of Combinations of Soy Hydrolysates and Intact Dairy Protein

TL1 hydrolysates of soy were combined with intact dairy proteins (i.e., caseinate or whey). The sensory profiles of these combinations of soy hydrolysates and intact dairy protein were compared to combinations of non-hydrolyzed (intact) soy and intact dairy proteins using the SQS method, which was detailed above in Example 6. A TL1 soy hydrolysate having a degree of hydrolysis of about 2.1% DH was diluted to a 5% slurry. Non-hydrolyzed soy protein was also diluted to a 5% slurry. For one trial, the TL1 hydrolysate was mixed with sodium caseinate (1:1) and assessed against a control sample, which was the non-hydrolyzed soy protein mixed with sodium caseinate (1:1). In a second trial, the TL1 hydrolysate was mixed with sweet dairy whey (4:1) and assessed against the control sample, which was non-hydrolyzed soy protein mixed with sweet dairy whey (4:1).

Table 22 presents the mean SQS scores for each sample and the diagnostic ratings. The combinations comprising the TL1 hydrolysate were generally rated as slightly different from the control sample. The diagnostic scores showed that combinations of TL1 hydrolysate and intact dairy protein have improved sensory characteristics relative to control samples (i.e., combinations of non-hydrolyzed soy and intact dairy proteins).

TABLE 22

SQS Analysis.

| Sample | SQS Score | Diagnostic Rating* |
|---|---|---|
| TL1 Hydrolysate + Casein | 3.7 | ↓ grain |
| TL1 Hydrolysate + Dairy Whey | 3.6 | ↓ soy/legume |

*↓ = slightly less than the control sample

Example 21

Analysis of Beverages Comprising a Protein Hydrolysate

Several prototypic ready-to-drink (RTD) neutral beverages and a dry-blended beverage mix were prepared using TL1 isolated soy protein hydrolysates with different degrees of hydrolysis. The beverages included a Soymilk Model beverage (i.e., unflavored low fat soymilk beverage containing 4% soy protein isolate, having 8.5 g protein/8 oz serving), a Combination Model beverage (i.e., unflavored beverage containing 8 g protein/8 oz serving, wherein half of the total protein is from soy and the other half of the protein is from skim milk), and a Dry-Blended Model beverage. The physical and sensory properties of the RTD beverages were compared to those of beverages prepared with different sources of non-hydrolyzed soy protein and/or dairy proteins.

Table 23 presents the formulation of the Soymilk Model beverages. To prepare the Soymilk Model beverages, the citrate was dissolved in water, and the soy protein was added, and the rate of mixing was increased to disperse the protein in the water. After the protein was thoroughly dispersed, the slurry temperature was increased to 77° C. (170° F.), the rate of mixing was reduced, and the slurry was mixed for 10 minutes. The maltodextrin, sugar and stabilizers were preblended together and added to the protein slurry. The slurry was mixed at low speed for 5 minutes. The sunflower oil was added to the slurry and mixing was continued at slow speed until the mixture was homogenous (approximately 3 minutes). The pH of the slurry was adjusted to about 7.0-7.2 using 45% potassium hydroxide. The slurry was homogenized at 500 psi (second stage) and 2500 psi (first stage). The slurry was pasteurized by ultra-high temperature (UHT) processing at 141° C. (286° F.) for 6 seconds. The mixture was cooled to 31° C. (88° F.) and packaged in sterilized bottles. The product was stored at refrigerated temperatures.

TABLE 23

Soymilk Model Beverage Formulation.

| Ingredients | Concentration (%) |
|---|---|
| Distilled Water | 89.4 |
| Maltodextrin | 4.2 |

TABLE 23-continued

Soymilk Model Beverage Formulation.

| Ingredients | Concentration (%) |
|---|---|
| Isolated Soy Protein (Non-hydrolyzed or TL1 Hydrolysate) (The amount of hydrolysate used was adjusted according to the protein content as is.) | 4.0 |
| Sugar | 1.4 |
| High Oleic Sunflower Oil | 0.7 |
| Potassium citrate | 0.3 |
| Stabilizers | 0.03 |

Table 24 presents the formulation of the Combination Model beverage. To prepare the Combination Model beverages, the citrate was dissolved in water with moderate mixing. The soy protein was added, and the rate of mixing was increased to disperse the protein in the water. After the protein was thoroughly dispersed, the slurry temperature was increased to 77° C. (170° F.), the rate of mixing was reduced, and the slurry was mixed for 10 minutes. The maltodextrin, sugar, vitamin/mineral premix, magnesium phosphate, cellulose, and stabilizers were preblended together and added to the protein slurry. The slurry was mixed at low speed for 5 minutes. The sunflower oil was added to the slurry and mixing was continued at slow speed until the mixture was homogenous (approximately 3 minutes). The pH of the slurry was adjusted to about 6.9-7.1 using 45% potassium hydroxide or 50% citric acid. The skim milk was slowly heated to 72° C. (162° F.), the soy protein slurry was added to the heated skim milk, and the mixture was slowly mixed for 3 minutes. The mixture was homogenized at 500 psi (second stage) and 2500 psi (first stage). The mixture was pasteurized by ultra-high temperature (UHT) processing at 141° C. (286° F.) for 6 seconds. The mixture was cooled to 31° C. (88° F.) and packaged in sterilized bottles. The product was stored at refrigerated temperatures.

TABLE 24

Combination Model Beverage Formulation.

| Ingredients | Concentration (%) |
|---|---|
| Skim milk | 50.0 |
| Distilled Water | 44.0 |
| Maltodextrin | 2.0 |
| Isolated Soy Protein (Non-hydrolyzed or TL1 Hydrolysate) (The amount of hydrolysate used was adjusted according to the protein content as is.) | 1.8 |
| Sugar | 1.0 |
| High Oleic Sunflower Oil | 0.8 |
| Cellulose gel | 0.3 |
| Sodium citrate, dehydrate | 0.05 |
| Magnesium phosphate, dibasic | 0.04 |
| Stabilizer | 0.02 |
| Vitamin/mineral premix | 0.006 |

The formulation of the Dry-Blended Model beverage is presented in Table 25. To make the beverage mix, the soy protein and cocoa powder were sieved and mixed with all of the other ingredients for 15 minutes at medium speed. The dry powder was stored in sanitized containers.

TABLE 25

Dry-Blended Model Beverage Formulation.

| Ingredients | Concentration (%) |
|---|---|
| Isolated Soy Protein (Non-hydrolyzed or TL1 Hydrolysate) (The amount of hydrolysate used was adjusted according to the protein content as is.) | 17.0 |
| Whey Protein Isolate | 16.0 |
| Sugar | 3.3 |
| Fructose | 3.3 |
| Cocoa | 3.0 |
| Fat Powder | 1.4 |
| Stabilizer | 0.4 |
| Sweetness Enhancer | 0.30 |
| Chocolate flavor | 0.70 |
| Cream | 0.20 |
| Vitamin Premix | 0.06 |
| Sucralose | 0.04 |
| Total | 45.5 |

To measure the viscosity of the beverages, the Soymilk Model and Combination Model beverages were shaken to achieve a uniform dispersion, and a serving size of Dry-Blended Model beverage dry powder was completely dispersed in the specified amount of water using a blender at low speed for 30-40 seconds or until fully dispersed. Each sample was immediately poured into a 180 ml beaker (no. 14070, Kimax®, USA), which was filled until the bottom of the curved portion of the beaker was reached. Any visible foam was removed before measuring. After the fixed time period had elapsed, the viscosity was measured in centipoises (cP) using a Brookfield viscometer (model DV-II+) (Brookfield Engineering Laboratories, Inc., Middleboro, Mass.) with spindle #1 and RPM60 for 1 minute (at 25-30° C.).

To assess the stability of the Soymilk Model beverages, the samples were collected in 250-ml sterile square media bottles after UHT treatment. The bottles were stored (undisturbed) at room temperature (25° C.) for 4 weeks. The bottles were then placed on a flat surface and the level of sediment was measured using a ruler (minimum 100 mm in 1 mm increments). Percent sedimentation was obtained using the following formula: (sedimentation (mm)/total liquid volume (mm))×100. If the sediment layer was in the bottom of the bottle and below the end of the ruler when placed against the side of the sample bottle, this was recorded as trace sediment.

Tables 26 and 27 present the viscosity and stability of the Soymilk Model and Combination Model beverages, respectively. The viscosity measurements of the Soymilk Model beverages were in parity with the non-hydrolyzed soy control samples. The viscosity measurements of the Combination Model beverages were within the range of the control sample containing soy and slightly less than the milk control sample. All of the Soymilk Model and Combination Model beverages had good stability. These data reveal that the functional properties of the model beverages were not negatively affected by using TL1 isolated soy protein hydrolysates with different degrees of hydrolysis.

TABLE 26

Properties of Soymilk Model Beverages.

| Sample Description | Viscosity (cP) | Stability (% Suspension) |
|---|---|---|
| Control 1 (Non-hydrolyzed Soy) | 5.8-6.7 | 93.2-93.7% |
| Control 2 (Non-hydrolyzed Soy) | 5.6 | 98.9% |
| TL1, 1.2% DH | 5.8 | 98.9% |
| TL1, 1.4% DH | 5.5 | 98.9% |
| TL1, 1.5% DH | 5.3 | 98.9% |
| TL1, 2.2% DH | 5.6 | 98.9% |
| TL1, 3.2% DH | 5.1 | 96.1% |

TABLE 27

Properties of Combination Model Beverages.

| Sample Description | Viscosity (cP) |
|---|---|
| Control 1 (100% Skim Milk) | 13.1 |
| Control 2 (50% Non-hydrolyzed Soy and 50% Skim Milk) | 9.7-12.6 |
| TL1, 1.2% DH | 12.7 |
| TL1, 1.4% DH | 10.1 |
| TL1, 1.4% DH | 10.6 |
| TL1, 1.5% DH | 12.2 |
| TL1, 2.2% DH | 11.3 |
| TL1, 2.3% DH | 9.4 |
| TL1, 3.2% DH | 10.7 |

Figure 15:
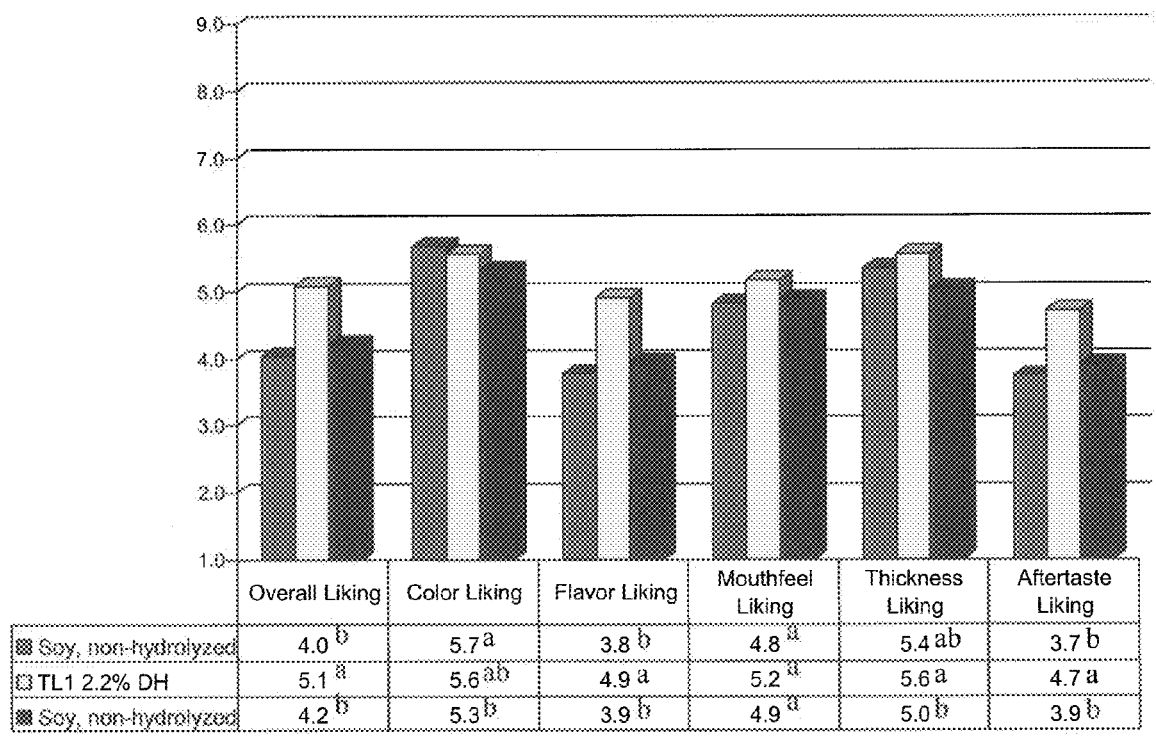
FIG. 15 presents the mean Hedonic scores for the Soymilk Model beverages. The scale was: 1=dislike extremely; 5=neutral; 9=like extremely. Means in the same column followed by a different letter are significantly different at 95% confidence.
Figure 16:
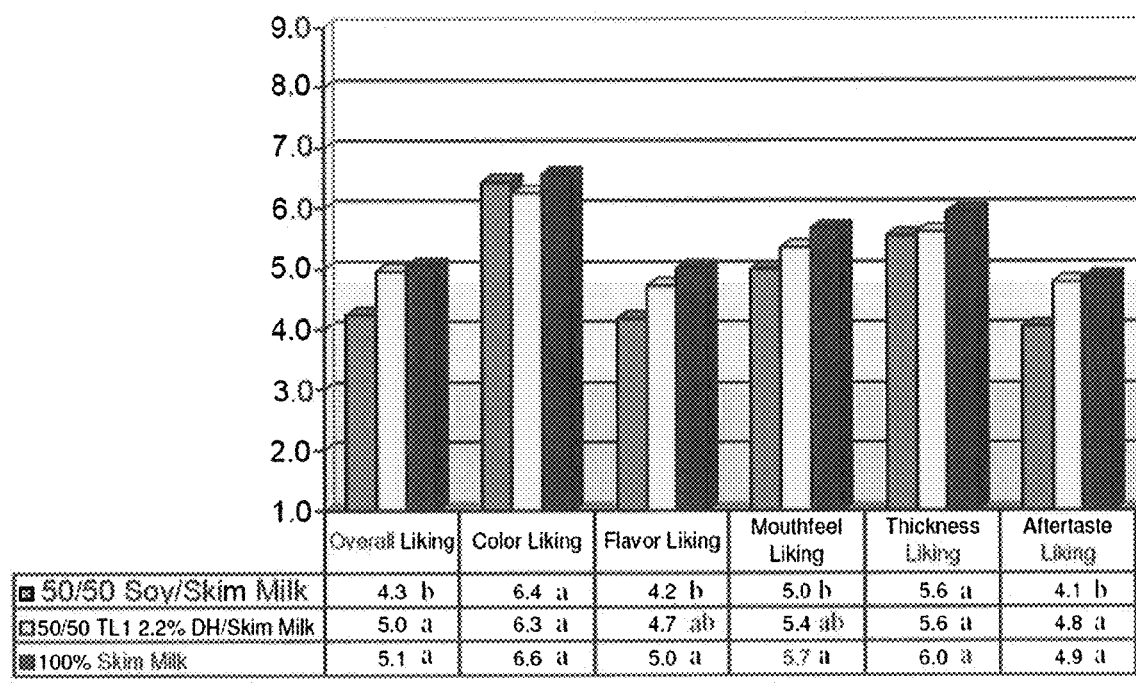
FIG. 16 presents the mean Hedonic scores for the Combination Model beverages. The scale was: 1=dislike extremely; 5=neutral; 9=like extremely. Means in the same column followed by a different letter are significantly different at 95% confidence.

Consumer testing of the sensory and flavor attributes of the various model beverages was assessed using the nine-point Hedonic Scale. The beverages were ranked on a scale of 1 for dislike extremely to 9 for like extremely, with 5 indicating neither like nor dislike. FIG. 15 presents the forced rankings of the Soymilk Model beverages, i.e., the two control samples and the TL1 2.2% DH sample. The TL1 hydrolysate sample was rated significantly higher than the two control samples with respect to "overall liking," "flavor liking," and "aftertaste liking." In addition, when asked to force rank, the consumers ranked the TL1 2.2% DH sample as the preferred sample of the set. FIG. 16 presents the forced rankings of the Combination Model beverages, i.e., 100% skim milk control, 50% non-hydrolyzed soy/50% skim milk, and 50% TL1 2.2% DH soy hydrolysate/50% skim milk. The TL1 hydrolysate-containing sample was rated significantly higher than the non-hydrolyzed soy containing sample in nearly all liking attributes and scored at parity with the 100% skim milk control sample with respect to all liking attributes (i.e., overall liking, color liking, flavor liking, mouthfeel liking, thickness liking, and aftertaste liking).

The Soymilk Model and Combination Model beverages and their corresponding protein slurries were also analyzed using the SQS method (as detailed in Example 6). Table 28 presents the SQS scores and the diagnostic ratings. Each test sample was compared to a control sample, as indicated in the table. In general, the samples containing TL1 hydrolysates had reduced soy/legume, grain, and cardboard/woody sensory attributes relative to the control samples.

TABLE 28

SQS Scores and Diagnostics* of Model Beverages.

| Sample Description | Protein Slurry | Soymilk Model | Combination Model | Dry-Blended Model |
|---|---|---|---|---|
| Control | Non-hydrolyzed soy | Beverage with non-hydrolyzed soy | Beverage with non-hydrolyzed soy | Beverage with non-hydrolyzed soy |
| TL1 1.2% DH | SQS = 3.5<br>↓ Grain<br>↓ Soy/Legume<br>↑ Bitter | SQS = 3.6<br>↓ Soy/Legume<br>↓ Cardboard/Woody | SQS = 4.0<br>No difference | SQS = 4.0<br>↓ Cardboard/Woody |
| TL1 1.4% DH | SQS = 3.8<br>↓ Grain<br>↓ Soy/Legume<br>↓ Cardboard/Woody<br>↓ Viscosity | SQS = 3.7<br>↓ Grain<br>↓ Soy/Legume<br>↓ Cardboard/Woody | | SQS = 3.4<br>↓ Cardboard/Woody |
| TL1 1.5% DH | SQS = 3.9<br>↓ Soy/Legume | SQS = 3.7<br>↓ Soy/Legume<br>↓ Cardboard/Woody | | |
| TL1 2.2% DH | SQS = 3.4<br>↓ Grain<br>↓ Soy/Legume<br>↑ Bitter | SQS = 3.5<br>↓ Soy/Legume | SQS = 3.8<br>↓ Soy/Legume | SQS = 3.4<br>↓ Viscosity<br>↓ Particle Amount |
| TL1 3.2% DH | SQS = 3.4<br>↓ Grain<br>↑ Bitter | SQS = 3.5<br>↓ Soy/Legume | SQS = 3.9<br>↓ Soy/Legume | SQS = 3.6<br>↓ Viscosity<br>↓ Particle Amount |

*↑↑↑ extremely more, ↑↑ moderately more, ↑ slightly more than the control sample. ↓↓↓ extremely less, ↓↓ moderately less, ↓ slightly less than the control sample.

---

What is claimed is:

1. A protein hydrolysate composition, the composition comprising a mixture of polypeptide fragments having primarily either an arginine residue or a lysine residue at each carboxyl terminus, the composition having a degree of hydrolysis of at least about 0.2% DH to about 8% DH and a soluble solids index of at least about 80% at a pH of greater than about 6.0.

2. The protein hydrolysate composition of claim 1, wherein the composition is derived from a protein selected from the group consisting of soy, barley, canola, lupin, maize, oat, pea, potato, rice, wheat, animal, egg, and combinations thereof.

3. The protein hydrolysate composition of claim 1, wherein the composition is derived from soy in combination with at least one protein selected from the group consisting of barley, canola, lupin, maize, oat, pea, potato, rice, wheat, animal, dairy, and egg.

4. The protein hydrolysate composition of claim 2, wherein the protein is soy.

5. The protein hydrolysate composition of claim 4, wherein the degree of hydrolysis of the composition is from about 2% DH to about 8% DH.

6. The protein hydrolysate composition of claim 1, wherein the composition is substantially stable at about pH 7.0 to about pH 8.0 when the degree of hydrolysis of the composition is from about 1% DH to about 6% DH.

7. The protein hydrolysate composition of claim 1, wherein the composition is substantially more translucent when the degree of hydrolysis is about 6% DH compared to when the degree of hydrolysis is about 1% DH.

8. The protein composition of claim 1, wherein the composition has substantially less grain and soy/legume sensory attributes when the degree of hydrolysis is from about 1% DH to about 6% DH compared to when the degree of hydrolysis is about 0.2% DH.

9. The protein hydrolysate composition of claim 1, wherein the composition has substantially less bitter sensory attributes when the degree of hydrolysis is less than about 2% DH.

10. The protein hydrolysate composition of claim 4, wherein the composition comprises at least two polypeptide fragments selected from the group consisting of SEQ ID NO:5-177 and 270-274.

11. The protein hydrolysate composition of claim 3, wherein the composition is derived from soy and dairy proteins, and comprises at least two polypeptide fragments selected from the group consisting of SEQ ID NO:5-197 and 270-274.

12. The protein hydrolysate composition of claim 2, wherein the composition is derived from canola protein, and comprises at least two polypeptide fragments selected from the group consisting of SEQ ID NO:198-237.

13. The protein hydrolysate composition of claim 2, wherein the composition is derived from maize protein, and comprises at least two polypeptide fragments selected from the group consisting of SEQ ID NO:238-261.

14. The protein hydrolysate composition of claim 2, wherein the composition is derived from wheat protein, and comprises at least two polypeptide fragments selected from the group consisting of SEQ ID NO:262-269.

15. The protein hydrolysate composition of claim 1, wherein the composition further comprises a non-hydrolyzed protein selected from the group consisting of barley, canola, lupin, maize, oat, pea, potato, rice, soy, wheat, animal, dairy, egg, and combinations thereof.

16. A process for preparing a protein hydrolysate composition, the process comprising contacting a protein material with an endopeptidase that specifically cleaves peptide bonds of the protein material on the carboxyl terminal side of an arginine residue or a lysine residue to produce a protein hydrolysate composition having a degree of hydrolysis of at least about 0.2% DH to about 8% DH and a soluble solids index of at least about 80% at a pH of greater than about 6.0.

17. The process of claim 16, wherein the endopeptidase is a food grade microbial enzyme.

18. The process of claim 17, wherein the endopeptidase is a trypsin-like protease.

19. The process of claim 18, wherein the endopeptidase is a selected from the group consisting of trypsin-like protease from *Fusarium oxysporum*, trypsin-like protease from *Fusarium solani*, trypsin-like protease from *Fusarium* cf. *solani*, and lysyl endopeptidase from *Achromobacter lyticus*.

20. The process of claim 19, wherein the endopeptidase is trypsin-like protease from *Fusarium oxysporum*.

21. The process of claim 17, wherein the endopeptidase comprises an amino acid sequence that is at least 80% identical to a sequence selected from the group consisting of SEQ ID NO:1, 2, 3, and 4.

22. The process of claim 21, wherein the endopeptidase comprises an amino acid sequence that is at least 90% identical to a sequence selected from the group consisting of SEQ ID NO:1, 2, 3, and 4.

23. The process of claim 22, wherein the endopeptidase comprises an amino acid sequence that is at least 95% identical to a sequence selected from the group consisting of SEQ ID NO:1, 2, 3, and 4.

24. The process of claim 23, wherein the endopeptidase comprises an amino acid sequence that is at least 99% identical to a sequence selected from the group consisting of SEQ ID NO:1, 2, 3, and 4.

25. The process of claim 16, wherein the endopeptidase has optimal proteolytic activity at a pH from about 7.0 to about 9.0 and at a temperature from about 45° C. to about 60° C.

26. The process of claim 16, wherein about 10 mg to about 1000 mg of the endopeptidase is contacted with each kilogram of protein material.

27. The process of claim 16, wherein the protein material is selected from the group consisting of soy, barley, canola, lupin, maize, oat, pea, potato, rice, wheat, animal, egg, and combinations thereof.

28. The process of claim 16, wherein the protein material is soy in combination with at least one protein selected from the group consisting of barley, canola, lupin, maize, oat, pea, potato, rice, wheat, animal, dairy, and egg.

29. The process of claim 16, wherein the protein material is soy.

30. The process of claim 29, wherein the soy protein material is selected from the group consisting of soy extract, soymilk, soymilk powder, soy curd, defatted soy flour, partially defatted soy flour, full fat soy flour, isolated soy protein, soy protein concentrate, and combinations thereof.

31. The process of claim 29, wherein the wherein the degree of hydrolysis of the composition is from about 2% DH to about 8% DH.

32. The process of claim 29, wherein the protein hydrolysate composition comprises at least two polypeptide fragments selected from the group consisting of SEQ ID NO:5-177 and 270-274.

33. The process of claim 28, wherein the protein material is a combination of soy and dairy, and the protein hydrolysate composition comprises at least two polypeptide fragments selected from the group consisting of SEQ ID NO:5-197 and 270-274.

34. The process of claim 27, wherein the protein material is canola, and the protein hydrolysate composition comprises at least two polypeptide fragments selected from the group consisting of SEQ ID NO:198-237.

35. The process of claim 27, wherein the protein material is maize, and the protein hydrolysate composition comprises at least two polypeptide fragments selected from the group consisting of SEQ ID NO:238-261.

36. The process of claim 27, wherein the protein material is wheat, and the protein hydrolysate composition comprises at least two polypeptide fragments selected from the group consisting of SEQ ID NO:261-269.

37. A food product, the food product comprising:
  (a) an edible material; and
  (b) a protein hydrolysate composition comprising a mixture of polypeptide fragments having primarily either an arginine residue or a lysine residue at each carboxyl terminus, the composition having a degree of hydrolysis of at least about 0.2% DH to about 8% DH and a soluble solids index of at least about 80% at a pH of greater than about 6.0.

38. The food product of claim 37, wherein the protein hydrolysate composition is derived from a protein selected from the group consisting of soy, barley, canola, lupin, maize, oat, pea, potato, rice, wheat, animal, egg, and combinations thereof.

39. The food product of claim 37, wherein the protein hydrolysate composition is derived from soy in combination with at least one protein selected from the group consisting of barley, canola, lupin, maize, oat, pea, potato, rice, wheat, animal, dairy, and egg.

40. The food product of claim 37, wherein the protein hydrolysate composition is derived from soy, and the degree of hydrolysis is from about 2% DH to about 8% DH.

41. The food product of claim 37, wherein the food product is a beverage.

42. The food product of claim 41, wherein the beverage is selected from the group consisting of a ready-to-drink beverage, a milk or milk analog beverage, a weight management beverage, a protein shake, and a meal replacement drink.

43. The food product of claim 41, wherein the beverage has a pH of about 6.5 to about 7.5.

44. The food product of claim 41, wherein the edible material is selected from the group consisting of skim milk, whole milk, cream, dried milk powder, non-fat dry milk powder, caseinate, soy protein concentrate, soy protein isolate, whey protein concentrate, whey protein isolate, chocolate, cocoa powder, coffee, and combinations thereof.

45. The food product of claim 37, wherein the food product further comprises an ingredient selected from the group consisting of a sweetening agent, an emulsifying agent, a thickening agent, a stabilizer, a lipid material, a preservative, an antioxidant, a flavoring agent, a coloring agent, a vitamin, a mineral, and combinations thereof.

46. The food product of claim 37, wherein the food product is selected from the group consisting of a food bar, a nutritional supplement, a cereal-based product, a meat or meat analog product, and a dairy or dairy analog product.

47. The protein hydrolysate composition of claim 4, wherein the composition comprises at least two polypeptide fragments consisting of a sequence selected from the group consisting of SEQ ID NO:5-177 and 270-274.

48. The protein hydrolysate composition of claim 3, wherein the composition is derived from soy and dairy proteins, and comprises at least two polypeptide fragments consisting of a sequence selected from the group consisting of SEQ ID NO:5-197 and 270-274.

* * * * *